US011352397B2

(12) United States Patent
Joshi et al.

(10) Patent No.: US 11,352,397 B2
(45) Date of Patent: Jun. 7, 2022

(54) GENETIC REPROGRAMMING OF BACTERIAL BIOFILMS

(71) Applicant: President and Fellows of Harvard College, Cambridge, MA (US)

(72) Inventors: Neel Satish Joshi, Somerville, MA (US); Peter Q. Nguyen, Malden, MA (US); Zsofia Magarian, Durham, NC (US)

(*) Notice: Subject to any disclaimer, the term of this patent is extended or adjusted under 35 U.S.C. 154(b) by 0 days.

(21) Appl. No.: 16/713,368

(22) Filed: Dec. 13, 2019

(65) Prior Publication Data

US 2020/0255480 A1   Aug. 13, 2020

Related U.S. Application Data

(63) Continuation of application No. 15/808,237, filed on Nov. 9, 2017, now Pat. No. 10,550,160, which is a continuation of application No. 14/786,304, filed as application No. PCT/US2014/035095 on Apr. 23, 2014, now Pat. No. 9,815,871.

(60) Provisional application No. 61/814,908, filed on Apr. 23, 2013.

(51) Int. Cl.
  *C07K 14/245* (2006.01)
  *C07K 14/21* (2006.01)

(52) U.S. Cl.
  CPC .......... *C07K 14/245* (2013.01); *C07K 14/21* (2013.01); *C07K 2319/20* (2013.01); *C07K 2319/735* (2013.01)

(58) Field of Classification Search
  None
  See application file for complete search history.

(56) References Cited

U.S. PATENT DOCUMENTS

| | | | |
|---|---|---|---|
| 5,762,620 A | 6/1998 | Cartmell et al. |
| 6,864,365 B1 | 3/2005 | White et al. |
| 8,741,417 B2 | 6/2014 | Lee et al. |
| 9,095,558 B2 | 8/2015 | Mayes et al. |
| 9,815,871 B2 | 11/2017 | Joshi et al. |
| 10,550,160 B2 | 2/2020 | Joshi et al. |
| 11,098,133 B2 | 8/2021 | Duraj-Thatte et al. |
| 2004/0220296 A1 | 11/2004 | Lowman et al. |
| 2010/0016549 A1 | 1/2010 | O'Mahony et al. |
| 2011/0033389 A1 | 2/2011 | Chen et al. |
| 2011/0108199 A1 | 5/2011 | Miller |
| 2012/0190566 A1 | 7/2012 | Lindquist et al. |
| 2013/0040889 A1 | 2/2013 | Bolt et al. |
| 2013/0136697 A1 | 5/2013 | Kannan et al. |
| 2014/0105861 A1 | 4/2014 | March et al. |
| 2014/0302043 A1 | 10/2014 | Whittle |
| 2014/0370013 A1 | 12/2014 | Desjarlais et al. |
| 2015/0342893 A1 | 12/2015 | Coulter et al. |
| 2018/0258435 A1 | 9/2018 | Joshi et al. |
| 2020/0248190 A1 | 8/2020 | Joshi et al. |
| 2020/0255480 A1 | 8/2020 | Joshi et al. |

FOREIGN PATENT DOCUMENTS

| | | |
|---|---|---|
| JP | 2006/503545 A | 2/2006 |
| JP | 2008/531059 A | 8/2008 |
| JP | 2009/73766 A | 4/2009 |
| JP | 2010/515445 A | 5/2010 |
| JP | 2014/156428 A | 8/2014 |
| JP | 2014/527405 A | 10/2014 |
| KR | 2012/0060442 A | 6/2012 |
| WO | WO-2003/068934 A2 | 8/2003 |
| WO | WO-2006/096515 A2 | 9/2006 |
| WO | WO-2008/084115 A2 | 7/2008 |
| WO | WO-2011/126174 A1 | 10/2011 |
| WO | WO-2012/138570 A2 | 10/2012 |
| WO | WO-2012/166906 A1 | 12/2012 |
| WO | WO-2013/009545 A1 | 1/2013 |
| WO | WO-2013/020074 A2 | 2/2013 |
| WO | WO-2013/188529 A1 | 12/2013 |
| WO | WO-2014/018572 A2 | 1/2014 |
| WO | WO-2014/078489 A1 | 5/2014 |
| WO | WO-2014/139468 A1 | 9/2014 |
| WO | WO-2014/176311 A1 | 10/2014 |
| WO | WO-2015/080671 A1 | 6/2015 |
| WO | WO-2015/097289 A1 | 7/2015 |
| WO | WO-2016/164422 A2 | 10/2016 |

OTHER PUBLICATIONS

Skolnick et al. Trends in Biotechnology, 18: 34-39, 2000.*
Rudinger J. In: Peptide Hormones. (Ed) JA Parsons, University Park Press, pp. 1-7, 1976.*
Greenspan et al. Nature Biotechnology 17: 936-937, 1999.*
Chen et al., "Fusion Protein Linkers: Property, Design, and Functionality," Adv Drug Deliv Rev, 65(10): 1357-1369 (32 pages)(2013).
Chen et al., "Synthesis and patterning of tunable multiscale materials with engineered cells," Nature Materials, 13 (5): 515-23 and Supplementary Information (20 pages)(2014).
Courchesne et al., "Scalable Production of Genetically Engineered Nanofibrous Macoscopic Material via Filtration," ACS Biomater. Sci. Eng., 3: 733-741 and supporting information (2017).
Hancock et al., "Probiotic *Escherichia coli* strain Nissle 1917 outcompetes intestinal pathogens during biofilm formation," Journal of Medical Microbiology, 59(4): 392-399 (2010).
International Preliminary Report on Patentability for Application No. PCT/US2017/033579 dated Nov. 29, 2018 (20 pages).
International Search Report and Written Opinion for Application No. PCT/US2017/033579 dated Oct. 2, 2017 (22 pages).
International Search Report and Written Opinion for International Application No. PCT/US2016/026161 dated Dec. 19, 2016.
International Search Report for Application No. PCT/US2014/035095, dated Sep. 30, 2014, 5 pages.

(Continued)

*Primary Examiner* — Sarvamangala Devi
(74) *Attorney, Agent, or Firm* — Foley Hoag LLP; Dana M. Gordon; Jack Rosa

(57) ABSTRACT

Described herein are methods and compositions relating to engineered curli fibers, e.g. CsgA polypeptide. In some embodiments, the methods and compositions described herein relate to functionalized biofilms.

8 Claims, 35 Drawing Sheets

Specification includes a Sequence Listing.

(56) References Cited

OTHER PUBLICATIONS

Klein et al., "Structure-Function Analysis of the Curli Accessory Protein CsgE Defines Surfaces Essential for Coordinating Amyloid Fiber Formation," mBio, 9(4): e01349-18 (15 pages)(2018).
Lieleg et al., "Biological hydrogels as selective diffusion barriers," Trends in Cell Biology, 21(9): 543-551 (2011).
Men et al., "An auto-biotinylated bifunctional protein nanowire for ultra-sensitive molecular biosensing," Biosens Bioelectron, 26(4): 1137-41 (2010).
Nash., "Engineering a Functionalized Biofilm-Based Material for Modulating *Escherichia coli*'s Effects in the Mammalian Gastrointestinal Tract," Bachelor's Thesis, Harvard College: 90 pages (2015).
Nguyen et al., "Programmable biofilm-based materials from engineered curli nanofibres," Nature Communications, 5(17): 4945 (10 pages)(2014).
Nussbaumer et al., "Bootstrapped Biocatalysis: Biofilm-Derived Materials as Reversibly Functionalizable Multienzyme Surfaces," ChemCatChem Communications, 9: 4328-4333 and supporting information (2017).
Tukel et al., "CsgA is a pathogen-associated molecular pattern of *Salmonella enterica* serotype Typhimurium that is recognized by Toll-like receptor 2," Mol Microbiol., 58(1): 289-304. (2005).
Van Gerven et al., "Secretion and functional display of fusion proteins through the curli biogenesis pathway," Mol Microbiol., 91(5): 1022-35 (2014).
Veggiani et al., "Superglue from bacteria: unbreakable bridges for protein nanotechnology," Trends Biotechnol., 32(10): 506-12 (2014).
Wang et al., "The molecular basis of functional bacterial amyloid polymerization and nucleation," J Biol Chem., 283(31): 21530-9 (2008).
Zakeri et al., "Peptide tag forming a rapid covalent bond to a protein, through engineering a bacterial adhesin," PNAS,109: E690-E697 (2012).
Zhang et al., "Panning and Identification of a Colon Tumor Binding Peptide from a Phage Display Peptide Library," Journal of Biomolecular Screening, 12(3): 429-435 (2007).
Hoffman et al., "Trefoil Factor Family (TFF) peptides and Chemokine Receptors: A Promising Relationship," J Med Chem, 52: 6505-6510 (2009).
Silacci et al., "Linker Length Matters, Fynomer-Fc Fusion with an Optimized Linker Displaying Picomolar IL-17A Inhibition Potency," J Biol Chem, 298(20): 14392-14398 (2014).

\* cited by examiner

| PEPTIDE | SEQUENCE | LENGTH (aa) | FUNCTION | REFERENCE |
|---|---|---|---|---|
| GBP | EPLQLKM | 7 | GRAPHENE EDGE BINDING. | JACS 2011, 133: p.14480. |
| CBP | HSSYWYAFNNKT | 12 | CARBON NANOTUBE BINDING. | NANO LETT. 2006, 6: p.40. |
| A3 | AYSSGAPPMPPF | 12 | GOLD BINDING. | SMALL 2005, 1(11): p.1048 |
| SpyTag | AHIVMVDAYKPTK | 13 | GENERAL COVALENT CAPTURE/DISPLAY OF PROTEINS. | PNAS 2012, IN PRESS. |
| MBD | KCTSDQDEQFIPKGCSK | 17 | BINDING TO STAINLESS STEEL SURFACES. | Mol MICROB. 2006 FEB;59(4): p.1083. |
| CT43 | CGPAGDSSGVDSRSVGPC | 18 | ZnS QUANTUM DOT TEMPLATING. | JACS 2010, 132: p.4731. |
| Mms6 | GGTIWTGKGLGLGLGLGLGAWGPI ILGVVGAGAVYAYMKSRDIESAQS DEEVELRDALA | 59 | MAGNETITE NP TEMPLATING. | JBC 2003, 278(10): p.8745 |

FIG. 1C

LINKER REGION = GS or GSGGSG
METAL BINDING DOMAIN = KCTSDQDEQFIPKGCSK

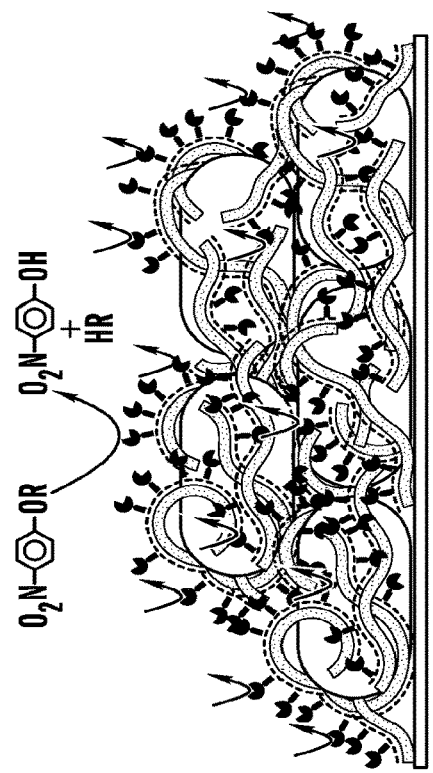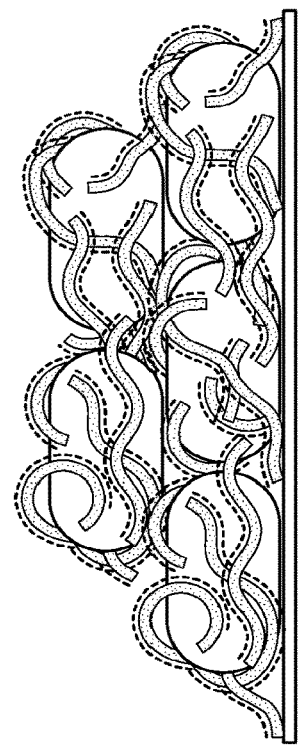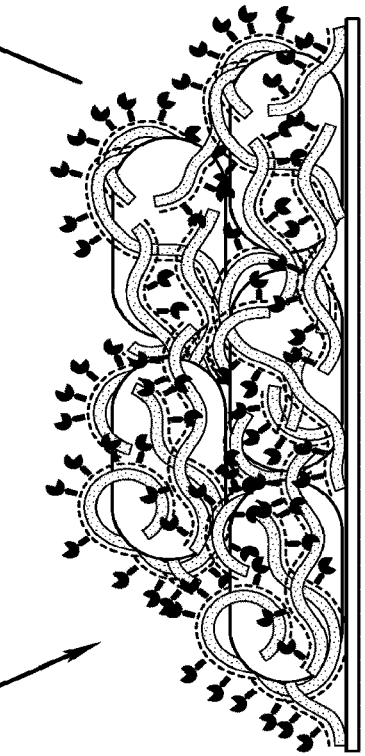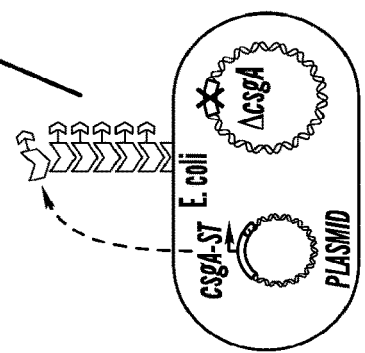
FIG. 8D
FIG. 8C
FIG. 8B
FIG. 8A

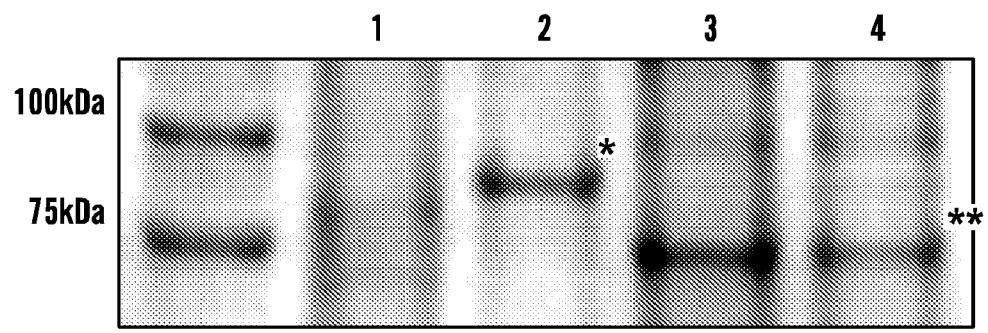
FIG. 9
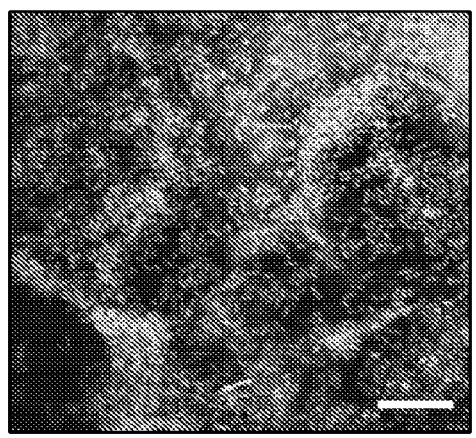 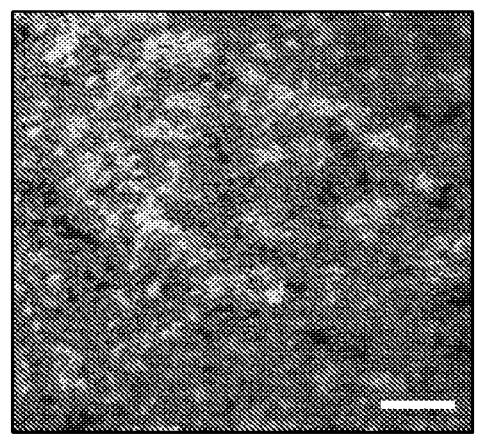
FIG. 10A      FIG. 10B

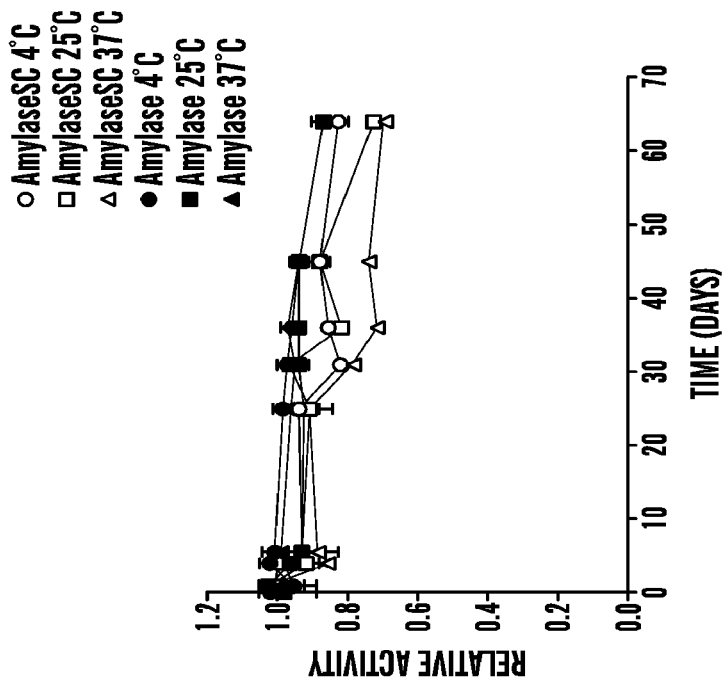
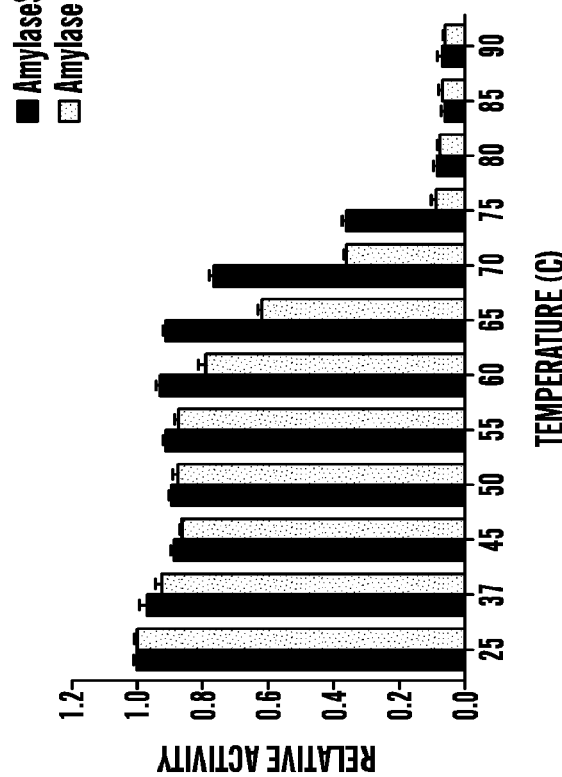
FIG. 14A
FIG. 14B

|  | Amylase | Amylase::SpyCatcher |
|---|---|---|
| Km (mM) | 1.31E-01 | 1.72E-01 |
| Vmax (mM/s) | 1.07E-05 | 1.26E-05 |
| Kcat (s-1) | 2.10E-02 | 2.47E-02 |
| Kcat/Km (mM-1s-1) | 1.60E-01 | 1.44E-01 |

GENETIC REPROGRAMMING OF BACTERIAL BIOFILMS

CROSS-REFERENCE TO RELATED APPLICATIONS

This application is a continuation application of U.S. application Ser. No. 15/808,237, filed Nov. 9, 2017, which issued as U.S. Pat. No. 10,550,160 on Feb. 4, 2020, which, in turn, is a continuation application of U.S. application Ser. No. 14/786,304, filed Oct. 22, 2015, which issued as U.S. Pat. No. 9,815,871 on Nov. 14, 2017, which, in turn, is a national stage entry of PCT/US2014/035095, filed on Apr. 23, 2014, which claims benefit under 35 U.S.C. § 119(e) of U.S. Provisional Application No. 61/814,908, filed on Apr. 23, 2013. The entire contents of each of the foregoing applications are incorporated herein by reference in their entirety.

TECHNICAL FIELD

The technology described herein relates to engineered polypeptides, bacteria comprising such polypeptides, and biofilms comprising said bacterial cells.

BACKGROUND

In nature, most bacteria exist as biofilm communities, residing in a self-generated protective nanoscale scaffold of proteins, sugars, lipids, and extracellular DNA that defends against environmental rigors. Biofilm formation is essential for bacterial adhesion and colonization of both natural and man-made surfaces. These highly evolved extracellular matrices hold untapped potential as a beneficial nanobiotechnology engineering platform. There is a significant body of work that investigates the use of biofilms for beneficial purposes such as wastewater treatment and biotransformations, but these efforts focus on the use of naturally occurring organisms that happen to have evolved various desired qualities. Efforts to rationally engineer the structure of biofilms at the molecular level have been absent. To date, there exists no robust and broad technology for the facile engineering of biofilm components.

SUMMARY

Described herein is a technology which permits the programming of an *E. coli* biofilm's functional properties by genetically appending functional peptide domains to the CsgA protein. After the new CsgA-peptide is secreted and assembled, the amyloid nanofiber network displays the peptide in very high density on its surface. The biofilm's function is then augmented according to the sequence of the displayed peptides. It is demonstrated herein that functional peptide domains of various lengths and secondary structures can be appended to CsgA without precluding the formation of curli fibers. Lastly, it is demonstrated that the peptide domains maintain their function in the context of the biofilm after secretion and assembly.

In one aspect, described herein is an engineered CsgA polypeptide, comprising a CsgA polypeptide with a C-terminal display tag flanking the CsgA polypeptide; wherein the display tag comprises an activity polypeptide and a linker sequence; wherein the linker sequence is located N-terminal to the display polypeptide; and wherein the linker sequence comprises at least 6 amino acids. In some embodiments, the linker sequence consists of glycine and serine residues. In some embodiments, the display tag and/or the activity polypeptide comprises a polypeptide selected from the group consisting of metal binding domain (MBD); SpyTag; graphene binding (GBP); carbon nanotube binding (CBP); gold binding (A3); CT43; FLAG; Z8; E14; QBP1; CLP12; and AFP8.

In one aspect, described herein is a nucleic acid sequence encoding the engineered CsgA polypeptide. In one aspect, described herein is a vector comprising the nucleic acid sequence encoding the engineered CsgA polypeptide. In one aspect, described herein is an engineered microbial cell comprising the vector, nucleic acid sequence, or engineered CsgA polypeptide. In one aspect, described herein is a biofilm comprising a cell described herein. In one aspect, described herein is a a biofilm produced by culturing the cells described herein under conditions suitable for the production of a biofilm.

In one aspect, described herein is a composition comprising an engineered CsgA polypeptide. In some embodiments, the composition comprises filaments comprising the engineered CsgA polypeptide. In some embodiments, the composition comprises a proteinaceous network. In some embodiments, the composition further comprises additional proteinaceous biofilm components. In some embodiments, the composition further comprises a cell as described herein.

In one aspect, described herein is the use of a cell, composition, or biofilm as described herein, to display a polypeptide within the biofilm, with the composition, or on the cell surface. In one aspect, described herein is the use of a cell, composition, or biofilm as described herein, in an application selected from the group consisting of biocatalysis; industrial biocatalysis; immobilized biocatalysis; chemical production; filtration; isolation of molecules from an aqueous solution; water filtration; bioremediation; nanoparticle synthesis; nanowire synthesis; display of optically active materials; biosensors; surface coating; therapeutic biomaterial; biological scaffold; structural reinforcement of an object; and as a delivery system for therapeutic agents.

BRIEF DESCRIPTION OF THE DRAWINGS

FIGS. 1A-1F depict a demonstration of the engineered biofilms described herein. FIG. 1A depicts a diagram of the molecular engineering of bacterial biofilms. FIG. 1B depicts, on the left, a schematic of the insertion library of CsgA-MBD fusions (Nor C-terminus, with various flexible linkers: N1,C1: no linker; N2,C2: GS; N3,C3: GSGGSG (SEQ ID NO: 13)). The amino acid sequence of Metal binding domain (MBD) is KCTSDQDEQFIPKGCSK (SEQ ID NO: 10). On the right is an image of Congo Red plate assay of insertion library. FIG. 1C depicts a table of different peptide/polypeptide insertions into the C3 site. The amino acid sequence of graphene binding protein(GBP) is EPLQLKM (SEQ ID NO: 6), the amino acid sequence of carbon nanotube binding protein (CBP) is HSSYWY-AFNNKT (SEQ ID NO: 7), the amino acid sequence of gold binding protein A3 is AYSSGAPPMPPF (SEQ ID NO: 8), the amino acid sequence of SpyTag is AHIVMVDAYKPTK (SEQ ID NO: 9), the amino acid sequence of metal binding domain (MBD) is KCTSDQDEQFIPKGCSK (SEQ ID NO: 10), the amino acid sequence of CT43 is CGPAGDSSGVDSRSVGPC (SEQ ID NO: 11), and the amino acid sequence of Mms6 is GGTIWTGKGLGLGLGLGLGAWGPIILGVVGAGA-VYAYMKSRDIESAQSDEEVELRDALA (SEQ ID NO: 12). FIG. 1D depicts streaks of the various CsgA fusions onto Congo Red plates. Red coloration is indicative of curli formation. FIG. 1E depicts TEM of: wildtype curli nanofibers (+CsgA), top; Curli-MBD fusion, middle; and Curli-SpyTag fusion, bottom. Arrows indicate curli fibers. FIG. 1F depicts FE-SEM images of wildtype curli nanofibers (+CsgA), top; and Curli-SpyTag fusion, bottom. Arrows indicate curli fibers.

FIG. 2A depicts a schematic of the attachment of proteins to the peptide-displaying curli biofilms, including two components: 1) secreted CsgA monomers that self-assemble to form the curli nanofibers and 2) a peptide that can interact specifically and strongly with an interacting protein domain (shown as a gray circle) to form a complex. By fusing the CsgA to the peptide at the C3 insertion site and coexpressing a fusion protein consisting of a variable protein (purple hexagon) fused to the interacting domain, the target protein can be displayed on engineered curli nanofibers. FIG. 2B depicts fluorescence microscopy images of curli biofilms after the addition of purified Venus-SC protein. Row 1: wild-type curli biofilms do not bind to the Venus-SC protein fusion. Row 2: Curli biofilms displaying the ST peptide tag when exposed to a Venus-SC(E77Q) mutant that cannot form the covalent isopepetide bond. Row 3: Only curli biofilms engineered to display the ST peptide tag shows specific interaction with the Venus-SC. All images are fluorescence microscopy images, with the red channel showing bacterial DNA (SYTO-61) and the GFP channel indicating the presence of the Venus-SC fluorescent protein reporter. FIG. 2C depicts the results of experiments with cell lysate containing fusion proteins. Overlay images of SYTO-61 and GFP channels indicates no binding of unpurified Venus-SC to wild-type curli (i), no binding of unpurified Venus-SC (E77Q) mutant to curli-ST biofilms, and to curli-ST (ii), and successful binding of unpurified Venus-SC mutant to curli-ST biofilms (iii).

FIG. 5A depicts a photographic image depicting cells expressing no curli (left), wildtype CsgA (middle), and MBD displayed curli (right) spotted onto a 304L steel coupon, allowed to dry, and then washed vigorously in water. Each of the spots on the surface was imaged using SEM. Cells expressing no curli proteins (5B) or wild-type CsgA (5C) did not adhere to the steel surface, whereas those expressing the CsgA-MBD fusion (5D) remained.

FIG. 6F depicts biofilms grown on PLL-modified glass substrates and then visualized with a nucleic-acid stain (SYTO61) to determine the presence of cells followed by treatment with SpyCatcher-Venus (GFP). Fluorescence microscopy of the biofilms reveals that only the proper combination of CsgA-SpyTag and SpyCatcher-Venus results in significant protein immobilization. Biofilms expressing wt-CsgA or those treated with the SpyCatcher(EQ) mutant that is unable to form covalent bonds with SpyTag are not capable of immobilizing the fluorescent protein. All images are scaled identically (scale bar=5 µm) and are representative of the entire biofilm-coated substrate surfaces.

FIGS. 8A-8D depict a diagram of the creation of catalytic biofilms using BIND. FIG. 8A depicts E. coli expressing CsgA fused to the 14 amino acid SpyTag (CsgA-ST). FIG. 8B depicts CsgA-ST assembled into amyloid fibers on the surface of the bacterium. When the bacteria form biofilms, curli fibers expressing ST create a polymer matrix around the cells. FIG. 8C demonstrates that this polymer matrix is covalently modified with an enzyme fused to SpyCatcher. FIG. 8D demonstrates that substrates to product conversion occurs on the high surface-area catalytic surface.

FIG. 9 depicts a SDS-PAGE gel of conjugation reaction between AmylaseSC and sheared curli fibers in PBS. Single star denotes AmylaseSC+CsgA-ST conjugate and double star denotes AmylaseSC. Lane 1) CsgA+AmylaseSC precipitation fraction, 2) CsgA-ST+AmylaseSC precipitation fraction, 3) CsgA+AmylaseSC soluble fraction, 4) CsgA-ST+AmylaseSC soluble fraction.

FIGS. 10A-10B depict biofilms immobilized on 96-well filter plate. FIG. 10A depicts CsgA WT expressing cells and FIG. 10B depicts CsgA-ST expressing cells visualized with fluorescence microscopy DAPI stain. Confocal microscopy shows bacteria in mostly mono and bilayers. Difference in the quantity of bacteria is due to normalizing the cell seeding to curli rather than biomass. Scale bar for confocal images is 10 µm.

FIG. 11A depicts a graph of biofilms containing ~4×10$^7$ cells incubated with 20-1500 pmol AmylaseSC. Dotted line shows one-site saturation binding fit. FIG. 11B depicts a graph of biofilms with increasing cell count incubated with 750 pmol AmylaseSC. Activity is reported in mM product released for 100 uL reaction.

FIG. 12A depicts a graph of the activity of biofilms compared with AmylaseSC in solution. FIG. 12B depits a graph of the metabolic activity of cells shown relative to activity at pH 7.

FIG. 13A depicts a graph of the activity of AmylaseSC on the biofilms post incubation in a panel of solvents. FIG. 13B depicts a graph of the activity in FIG. 13A plotted agains the partition coefficient of the organic solvents. FIG. 13C depicts a graph of the activity of AmylaseSC on the biofilms in varying solvent fraction of miscible organic solvent. FIG. 13D depicts a graph of the metabolic activity of cells post incubation in the panel of solvents.

FIGS. 14A-14B demonstrate the stability of AmylaseSC versus wild-type α-Amylase in solution. FIG. 14A depicts a graph of the activity of the two enzymes after a 30 minute exposure to a range of temperatures. FIG. 14B depicts a graph of the activity after storage at 4° C., 25° C., 37° C. over 64 days.

FIG. 15A depicts a graph of the activity of AmylaseSC with different concentrations of colorimetric substrate 4-nitrophenyl-a-D-maltopentaoside (pNPMP). FIG. 15B depicts Michaelis-Menten analysis.

FIG. 16A depicts a diagram demonstrating that in the BIND platform, csgA cells heterologously express and secrete fusion proteins consisting of an amyloidogenic domain (CsgA) and a functional peptide domain. This fusion protein self-assembles into an extracellular network of amyloid nanofibers, resulting in a biofilm material with programmed non-natural functions. FIGS. 16C-16P depict FE-SEM images of the peptide fusion BIND library transformed into LSR10 (MC4100, csgA) cells with no CsgA (FIG. 16C), wt-CsgA (FIG. 16D), and the BIND peptide panel (see Table 1): HIS (FIG. 16E), GBP (FIG. 16F), FLAG (FIG. 16G), CNBP (FIG. 16H), A3 (FIG. 16I), CLP12 (FIG. 16J), QBP1 (FIG. 16K), SpyTag (FIG. 16L), MBD (FIG. 16M), CT43 (FIG. 16N), AFP8 (FIG. 16O), and Mms6 (FIG. 16P). Scale bars, 1 μm.

FIG. 19A depicts a schematic showing the protein BIND immobilization strategy which uses an isopeptide bond forming splitprotein S. pyogenes FbaB adhesin system (24) to covalently attach proteins fused to the SpyCatcher domain onto BIND biofilms displaying the 13-residue SpyTag. FIGS. 19B-19G depict TEM and FE-SEM images of PHL628 csgA strains expressing no curli (FIGS. 19B and 19E), wild-type CsgA (FIGS. 19C and 19F), and the SpyTag-BIND biofilms (FIGS. 19D and 19G). Scale bars, 1 μm.

FIG. 21A depicts LSR10 cells expressing FLAG-BIND and FIG. 21B depicts wildtype curli probed using an anti-FLAG primary antibody and a 15-nm gold nanoparticle-labeled secondary antibody. Samples were blocked with 0.1% BSA in PBS and washed with 0.01% BSA in PBS before staining with 1% uranyl formate and imaged by TEM. Scale bars, 500 nm.

DETAILED DESCRIPTION

Figure 1A:
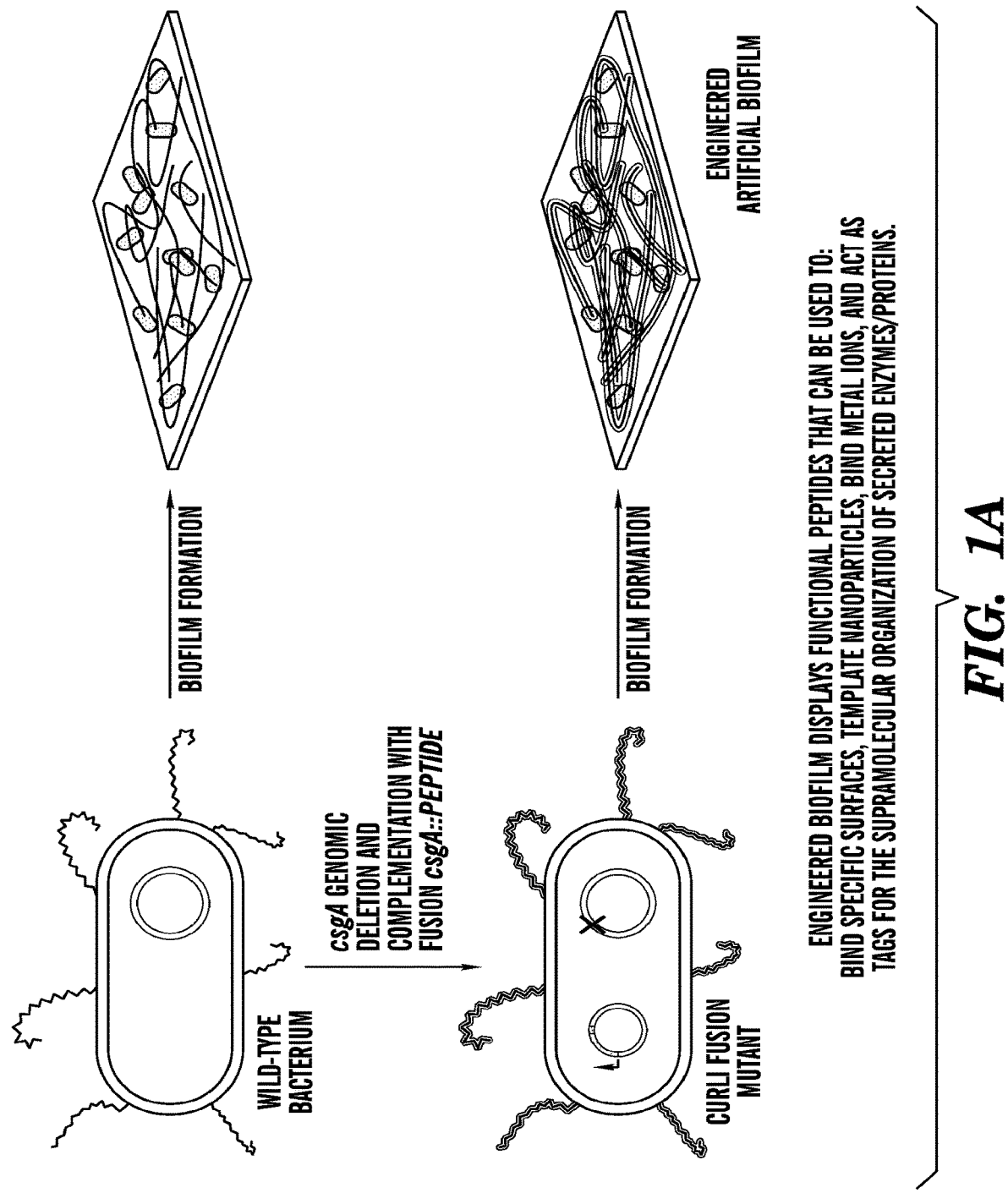

Embodiments of the technology described herein relate to the inventors' discovery of how to functionalize bacterial biofilms. More specifically, the inventors have discovered CsgA, the major component of E. coli biofilms, can be engineered to comprise polypeptides having a function or activity which provide the biofilm comprising the engineered CsgA with a new property or activity.

In one aspect, the technology described herein relates to an engineered CsgA polypeptide, comprising a CsgA polypeptide with a C-terminal display tag flanking the CsgA polypeptide. The display tag comprises an activity polypeptide and a linker sequence, wherein the linker sequence is located N-terminal to the display polypeptide and wherein the linker sequence comprises at least 6 amino acids. As used herein, "CsgA" (as distinguished from an engineered CsgA polypeptide) refers to the major structural subunit of curli. The sequences of CsgA and its homologs are known in a number of species, e.g. the sequence of E. coli CsgA is known (NCBI Gene ID NO: 949055; SEQ ID NO: 1 (polypeptide)). In some embodiments, "CsgA" refers to E. coli CsgA. In some embodiments, "CsgA" refers to a polypeptide having at least 80% homology to SEQ ID NO: 1 (e.g. 80% or greater homology, 90% or greater homology, or 95% or greater homology), e.g. naturally occurring mutations or variants of CsgA, homologs of CsgA, or engineered mutatations or variants of CsgA.

As used herein, an "engineered CsgA polypeptide" refers to a polypeptide comprising a C-terminal display tag flanking the CsgA polypeptide, e.g. a polypeptide display tag located on the c-terminus of a CsgA polypeptide. In some embodiments, the display tag is located on the C-terminus of a CsgA polypeptide of SEQ ID NO: 1. The display tag flanks the CsgA polypeptide, i.e., the entirety of the CsgA polypeptide is located on the N-terminus of the display tag, e.g. the display tag does not interrupt the sequence of the CsgA polypeptide.

As used herein a "display tag" is a polypeptide engineered to be located at the C-terminus of a polypeptide comprising a CsgA polypeptide. In some embodiments, a display tag comprises no more than 100 amino acids. In some embodiments, a display tag comprises no more than 50 amino acids. In some embodiments, a display tag comprises no more than 40 amino acids. In some embodiments, a display tag comprises no more than 30 amino acids.

A display tag as described herein comprises, from N-terminus to C-terminus, a linker sequence and an activity polypeptide. A linker sequence is a polypeptide sequence of at least 6 amino acids. In some embodiments, the linker sequence comprises from about 6 amino acids to about 50 amino acids. In some embodiments, the linker sequence comprises from about 6 amino acids to about 100 amino acids. In some embodiments, the linker sequence comprises from about 30 amino acids to about 100 amino acids. In some embodiments, the linker sequence comprises from about 40 amino acids to about 100 amino acids. In some embodiments, the linker sequence comprises from about 50 amino acids to about 100 amino acids. In some embodiments, the linker sequence comprises from about 6 amino acids to about 30 amino acids. In some embodiments, the linker sequence comprises from about 20 amino acids to about 50 amino acids. In some embodiments, the linker sequence comprises from about 30 amino acids to about 50 amino acids. In some embodiments, the linker sequence comprises from about 40 amino acids to about 50 amino acids. In some embodiments, the linker sequence comprises from about 6 amino acids to about 20 amino acids. In some embodiments, the linker sequence comprises from about 6 to about 10 amino acids. In some embodiments, the linker sequence comprises a flexible polypeptide, e.g a polypeptide not having a rigid secondary and/or tertiary structure. In some embodiments, the linker sequence comprises glycine and serine residues. In some embodiments at least 50% of the amino acids comprised by the linker sequence are glycine or serine residues, e.g. at least 50%, at least 60%, at least 70%, at least 80%, at least 90%, at least 95%, or more are glycine or serine residues. In some embodiments, the linker sequence consists of glycine and serine residues.

As referred to herein, an "activity polypeptide" refers to a polypeptide having an activity or function, such that when it is present in a biofilm, it confers upon the biofilm a property, function, or activity which it did not have in the absence of the activity of the polypeptide. Accordingly, an activity polypeptide can be, e.g. an enzyme, a polypeptide that binds another molecule, a binding domain, a peptide that is bound by another molecule (e.g. a ligand or epitope), or the like. Examples of polypeptides for use as activity polypeptides include, but are not limited to Metal binding domain (MBD); SpyTag; graphene binding (GBP); carbon nanotube binding (CBP); gold binding (A3); CT43; FLAG; Z8; E14; QBP1; CLP12; and AFP8. The sequences of these exemplary embodiments are provided herein, e.g. in FIG. 1C and Table 1.

In some embodiments, the activity polypeptide, when present as part of an engineered CsgA polypeptide, is functional. As used herein, a polypeptide is said to be "functional" or expressed as a "functional" polypeptide if the polypeptide retains at least about 50% of the activity (e.g. enzymatic activity or binding activity) that it has as an isolated polypeptide. One of skill in the art can readily detect increases in reaction products and/or detect decreases in reaction substrates, e.g. by mass spectroscopy (MS, including, e.g., MADLI/TOF, SELDI/TOF, LC-MS, GC-MS, HPLC-MS, etc., among others) or detect increases or decrease in binding to a binding partner, e.g. by immunoassays. In some embodiments, a functional activity polypeptide can retain at least 50% of the activity of the isolated polypeptide, e.g. 50% or more of the activity, 60% or more of the activity, 75% or more of the activity, or 90% or more of the activity of the isolated polypeptide.

In some embodiments, the activity polypeptide can be a conjugation domain. Such embodiments can permit immobilization of target proteins in the biofilm, e.g., when the target protein is too large to be expressed as a fusion with CsgA. The conjugation domain present on the engineered CsgA polypeptide can specifically bind to a partner conjugation domain present as part of the target protein, thereby incorporating the target protein into the biofilm. As used herein, "conjugation domain" refers to a polypeptide that can specifically bind to and/or be specifically bound by a partner conjugation domain, e.g. under conditions suitable for growth of a biofilm. A conjugation domain can be, e.g., about 100 amino acids or less in size, about 75 amino acids or less in size, about 50 amino acids or less in size, about 40 amino acids or less in size or smaller. A partner conjugation domain can be about the same size as the conjugation domain or larger, e.g., a partner conjugation domain can be about 4000 amino acids or less in size, about 3000 amino acids or less in size, about 2000 amino acids or less in size, about 1000 amino acids or less in size, about 500 amino acids or less in size, about 200 amino acids or less in size, about 100 amino acids or less in size, about 75 amino acids or less in size, about 50 amino acids or less in size, about 40 amino acids or less in size, or smaller. In some embodiments, the binding of the conjugation domain and partner conjugation domain is covalent. Examples of conjugation domains are known in the art and include, but are not limited to, SpyTag; biotin acceptor peptide (BAP); biotin carboxyl carrier protein (BCCP); and a peptide comprising a LPXTG (SEQ ID NO: 23) motif. Similarly, partner conjugation domains are known in the art and include but are not limited to, respectively, SpyCatcher, streptavidin; streptavidin; and peptides comprising aminoglycine. Further discussion of conjugation systems comprising a conjugation domain and a partner conjugation domain can be found, e.g., in Mao et al. J Am Chem Soc 2004 126:2670-1; Zakeri et al. PNAS 2012 109:E690-E697; and Maeda et al. Appl Environ Microbil 2008 74:5139-5145; each of which is incorporated by reference herein in its entirety. In some embodiments, an engineered CsgA polypeptide comprising conjugation domain has the sequence of SEQ ID NO: 3 or is encoded by a polynucleotide having the sequence of SEQ ID NO: 2.

Where the activity polypeptide is a conjugation domain, the target polypeptide comprising the partner conjugation domain can further comprise a "functionalizing polypeptide." As used herein, a "functionalizing polypeptide" refers to a polypeptide having an activity or function, such that when it is present in a biofilm, it confers upon the biofilm a property, function, or activity which it did not have in the absence of the polypeptide. A functionalizing polypeptide can be of any size and is not part of the engineered CsgA polypeptide. Exemplary functionalizing polypeptide can include, e.g. an enzyme, a polypeptide that binds another molecule, an antibody or the like. In some embodiments, a polypeptide comprising a functionalizing polypeptide and a conjugation domain can further comprise an extracellular localization tag, e.g. a sequence which will cause a cell expressing the polypeptide to secrete the polypeptide.

A functionalized engineered CsgA polypeptide or functionalized biofilm can be provided by contacting an engineered CsgA polypeptide comprising a conjugation domain (or a cell and/or biofilm comprising that polypeptide) with a polypeptide comprising the partner conjugation domain. In some embodiments, the engineered CsgA polypeptide and the polypeptide comprising the partner conjugation domain are maintained in contact for a period of time, i.e. the "binding step." In some embodiments, the binding step is followed by a washing step, e.g. to remove excess unbound polypeptide.

In some embodiments, an engineered CsgA polypeptide comprising a conjugation domain is bound to (or binds) the partner conjugation domain in the presence of albumin (i e the "binding step"). In some embodiments, the albumin is BSA. In some embodiments, the albumin is present at about 0.1% to about 10%. In some embodiments, the albumin is present at about 0.5% to about 5%. In some embodiments, the albumin is present at about 1% to about 2%. In some embodiments, the binding step is allowed to proceed for at least about 2 hours, e.g. about 2 hours or more, about 6 hours or more, about 12 hours or more, or about 24 hours or more. In some embodiments, the binding step is allowed to proceed in the presence of albumin.

In some embodiments, the washing step proceeds for about 10 minutes to about 6 hours. In some embodiments, the washing step proceeds for about 30 minutes to about 3 hours. In some embodiments, the washing step proceeds for about 90 minutes. In some embodiments, the polypeptides are agitated (e.g. shaken) during the washing step. In some embodiments, the washing step comprises washing the polypeptides in a solution of albumin. In some embodiments, the albumin is BSA. In some embodiments, the albumin is present at about 0.01% to about 3%. In some embodiments, the albumin is present at about 0.1% to about 1%. In some embodiments, the albumin is present at about 0.3%. In some embodiments, the washing step comprises 2 or more successive washes. In some embodiments, the washing step comprises 3 successive washes.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In one aspect, described herein is a nucleic acid sequence encoding an engineered CsgA polypeptide as described herein. In one aspect, described herein is a vector comprising a nucleic acid sequence encoding an engineered CsgA polypeptide as described herein. The term "vector", as used herein, refers to a nucleic acid construct designed for delivery to a host cell or transfer between different host cells. As used herein, a vector can be viral or non-viral. Many vectors useful for transferring genes into target cells are available, e.g. the vectors may be episomal, e.g., plasmids, virus derived vectors or may be integrated into the target cell genome, through homologous recombination or random integration. In some embodiments, a vector can be an expression vector. As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operatively linked to an expression control sequence when the expression control sequence controls and regulates the transcription and translation of that polynucleotide sequence.

In some embodiments, a nucleic acid encoding an engineered CsgA polypeptide can be present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/−(see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," Gene Expression Technology, vol. 185 (1990), which is hereby incorporated by reference in its entirety).

As used herein, the term "viral vector" refers to a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

In some embodiments, the nucleic acid encoding an engineered CsgA polypeptide can be constitutively expressed. In some embodiments, the nucleic acid encoding an engineered CsgA polypeptide can be operably linked to a constitutive promoter. In some embodiments, the nucleic acid encoding an engineered CsgA polypeptide can be inducibly expressed. In some embodiments, the nucleic acid encoding an engineered CsgA polypeptide can be operably linked to an inducible promoter. In some embodiments, the nucleic acid encoding an engineered CsgA polypeptide can be operably linked to a native CsgA promoter.

As described herein, an "inducible promoter" is one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1 992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the PLtetO-1 and Plac/are-1 promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including Cu2+ and Zn2+), galactose, tetracycline, IPTG (isopropyl-(3-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

In one aspect, described herein is an engineered microbial cell comprising an engineered CsgA polypeptide and/or comprising a vector or nucleic acid encoding such a polypeptide.

In some embodiments, the engineered CsgA polypeptide can comprise an activity polypeptide comprising a conjugation domain. In some embodiments, a cell encoding and/or comprising an engineered CsgA polypeptide can comprise an activity polypeptide comprising a conjugation domain can further encode and/or comprise a second engineered polypeptide comprising a partner conjugation domain and a functionalizing polypeptide. In some embodiments, described herein is a population of cells comprising two cell types, the first cell type encoding and/or comprising an engineered CsgA polypeptide comprising an activity polypeptide comprising a conjugation domain and the second cell type encoding and/or comprising a second engineered polypeptide comprising a partner conjugation domain and a functionalizing polypeptide. That is, it is contemplated herein that a single cell can comprise a CsgA polypeptide with a conjugation domain and also comprise the polypeptide which will bind to and/or be bound by that CsgA polypeptide or that a first cell can comprise a CsgA polypeptide with a conjugation domain and a second cell can comprise the polypeptide which will bind to and/or be bound by that CsgA polypeptide. It is further contemplated that an engineered CsgA polypeptide with a conjugation domain can be contacted with a second polypeptide comprising a partner conjugation domain and a functionalizing polypeptide, e.g. the second polypeptide can be produced (e.g. by a bacteria or eurkaryotic cell) and/or synthesized (and optionally isolated or purified) and then brought in contact with the engineered CsgA polypeptide, e.g. when the CsgA polypeptide is present on a cell surface and/or present in a biofilm.

A bacterial cell of the methods and compositions described herein can be any of any species. Preferably, the bacterial cells are of a species and/or strain which is amenable to culture and genetic manipulation. In some embodiments, the bacterial cell can be a gram-positive bacterial cell. In some embodiments, the bacterial cell can be a gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli*, *E. coli* BL21, *E. coli* Tuner, *E. coli* Rosetta™, *E. coli* JM101, and derivatives of any of the foregoing. Bacterial strains for protein expression are commercially available, e.g. EXPRESS™ Competent *E. coli* (Cat. No. C2523; New England Biosciences; Ipswich, Mass.). In some embodiments, the cell is an *E. coli* cell.

In some embodiments, the nucleic acid encoding an engineered CsgA polypeptide is comprised by a cell expressing wild-type CsgA. In some embodiments, the nucleic acid encoding an engineered CsgA polypeptide is comprised by a cell with a mutation and/or deletion of the wild-type CsgA gene, e.g. such that the cell does not express wild-type CsgA. In some embodiments, the nucleic acid encoding an engineered CsgA polypeptide is introduced into a cell by homolgous recombination, e.g. such that the nucleic acid encoding an engineered CsgA polypeptide replaces the wild-type CsgA gene in the cell.

In one aspect, described herein is a biofilm comprising an engineered microbial cell comprising one or more engineered CsgA polypeptide and/or comprising a vector or nucleic acid encoding such a polypeptides. As used herein, a "biofilm" refers to a mass of microorganisms which can adhere or is adhering to a surface. A biofilm comprises a matrix of extracellular polymeric substances, including, but not limited to extracellular DNA, proteins, glyopeptides, and polysaccharides. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony.

In some embodiments, the technology described herein relates to a biofilm that is produced by culturing an engineered microbial cell comprising an engineered CsgA polypeptide (and/or comprising a vector or nucleic acid encoding such a polypeptide) under conditions suitable for the production of a biofilm. Conditions suitable for the production of a biofilm can include, but are not limited to, conditions under which the microbial cell is capable of logarithmic growth and/or polypeptide synthesis. Conditions may vary depending upon the species and strain of microbial cell selected. Conditions for the culture of microbal cells are well known in the art. Biofilm production can also be induced and/or enhanced by methods well known in the art, e.g. contacting cells with subinhibitory concentrations of beta-lactam or aminoglycoside antibiotics, exposing cells to fluid flow, contacting cells with exogenous poly-N-acetylglucosamine (PNAG), or contacting cells with quorum sensing signal molecules. In some embodiments, conditions suitable for the production of a biofilm can also include conditions which increase the expression and secretion of CsgA, e.g. by exogenously expressing CsgD.

In some embodiments, the biofilm can comprise the cell which produced the biofilm.

In some embodiments, described herein is a composition comprising an engineered CsgA polypeptide as described herein.

When expressed by a cell capable of forming curli, e.g. a cell expressing CsgA, CsgB, CsgC, CsgD, CsgE, CsgF, and CsgG or some subset thereof, CsgA units will be assembled to form curli filaments, e.g. polymeric chains of CsgA. In some embodiments, filaments of the polypeptide can be present in the composition. In some embodiments, the filaments can be part of a proteinaceous network, e.g. multiple filaments which can be, e.g. interwoven, overlapping, and/or in contact with each other. In some embodiments, the proteinaceous network can comprise additional biofilm components, e.g. materials typically found in an *E. coli* biofilm. Non-limiting examples of biofilm components can include biofilm proteins (e.g. FimA, FimH, Ag43, AidA, and/or TibA) and/or non-proteinaceous biofilm components (e.g. cellulose, PGA and/or colonic acid). In some embodiments, the composition can further comprise an engineered microbial cell comprising an engineered CsgA polypeptide and/or comprising a vector or nucleic acid encoding such a polypeptide.

In one aspect, described herein is the use of a cell, composition, or biofilm comprising an engineered CsgA polypeptide (and/or comprising a vector or nucleic acid encoding such a polypeptide) to display a polypeptide, e.g. within the biofilm, within the composition, and/or on the cell surface. As used herein, "display" refers to expressing the polypeptide (e.g. as an activity polypeptide) in such a manner that it can come in contact with the extracellular environment. A displayed polypeptide can be capable of binding with a binding partner, catalyzing an enzymatic reaction, and/or performing any other activity which it would perform as an isolated polypeptide.

It is contemplated herein that a polypeptide displayed within a biofilm (e.g. an activity polypeptide and/or functionalizing polypeptide) will retain more activity than a soluble version of that polypeptide. It is contemplated herein that a polypeptide displayed within a biofilm (e.g. an activity polypeptide and/or functionalizing polypeptide) will retain more activity than a soluble version of that polypeptide when exposed to activity degrading conditions such as, e.g., high or low pH, organic solvents, dessication, high or low temperature, radiation, etc.

In one aspect, described herein is the use of a cell, composition, or biofilm comprising an engineered CsgA polypeptide (and/or comprising a vector or nucleic acid encoding such a polypeptide), in an application selected from the group consisting of biocatalysis; industrial biocatalysis; immobilized biocatalysis; chemical production; filtration; isolation of molecules from an aqueous solution; water filtration; bioremediation; nanoparticle synthesis; nanowire synthesis; display of optically active materials; biosensors; surface coating; therapeutic biomaterial; biological scaffold; structural reinforcement of an object; and as a delivery system for therapeutic agents. Exemplary, non-limiting embodiments of such applications and specific activity polypeptides for use therein are described in the Examples herein.

It is contemplated herein that a cell, composition and/or biofilm can comprise multiple different engineered CsgA polypeptides, each of which comprises a different activity polypeptide, e.g. an engineered CsgA polypeptide comprising an enzymatic activity polypeptide and an engineered CsgA polypeptide comprising a binding domain activity polypeptide. A cell, composition, and/or biofilm can comprise 1 or more engineered CsgA polypeptides, e.g. 1, 2, 3, 4, 5, 6, or more engineered CsgA polypeptides.

Exemplary, non-limiting embodiments of methods and compositions described herein follow:

BIND as a Biocatalytic Scaffold for the Display of Enzymes. Biofilms are attractive as catalysts for a variety of biochemical transformations due to the their ability to withstand harsh conditions, their propensity for surface attachment and their scalability.

In general, biotransformations are catalyzed either by enzymes inside living cells or by enzymes displayed on the cell surface. Both approaches have inherent limitations related to mass transfer and solubility of substrates, in the case of whole cells, or related to the limited surface area available on the cell membrane, in the case of surface display. Described herein is the development of technique called Biofilm Integrated Nanofiber Display (BIND) that enables the rational design of the biofilm extracellular matrix so that it can function as a substrate for site-specific covalent surface immobilization of enzymes. α-Amylase fused to an attachment domain, SpyCatcher, was immobilized onto *E. coli* biofilms displaying curli fibers with a capture domain, SpyTag. When compared to the free enzyme, the a-Amylase immobilized on the biofilm surface was protected from harsh pH conditions and exposure to water immiscible organic solvents. This work lays the foundation for a new method of using the extracellular polymeric matrix of *E. coli* for creating versatile and controllable biocatalytic surfaces.

BIND as a Living Coating for the Protection of Surfaces. Surfaces used in many applications require protective coatings to render them resistant to wear, chemical degradation (i.e. corrosion), and fouling from chemical and biological sources. The BIND platform provides a way to create living surface coating materials that can be programmed to exhibit a range of protective functions for surfaces on which the engineered biofilms are immobilized: 1) strong adhesion to the surface, 2) the ability to secrete soluble entities into the local environment that would prevent degradation or fouling, such as microbicides, reductants, etc., 3) the ability to secrete biopolymeric material to fill in cracks forming in the underlying substrate, or 4) the ability to template the growth of a mineral or other ordered material from a exogenously supplied building blocks.

Enzymatically-derived 13PDO can potentially be produced at a much lower cost than whole-cell fermentation processes, which require large amounts of media for every cycle and often produce metabolic side products, resulting in a complex mixture that must be processed to isolate the desired product. The BIND platform technology will reduce the cost barriers typically associated with immobilized enzyme biocatalysis, by eliminating the multi-step purification and immobilization with a single culturing step, and replacing costly synthetic scaffolds with an ultra-stable self-produced scaffold. The metabolic production of 13PDO by microorganisms from glycerol proceeds from 2 enzymatic step. The first step is the enzymatic dehydration of glycerol by Glycerol dehydratase (Gdh) to produce 3-hydroxypropionaldehyde (3HPA). The 3HPA is in turn reduced to 13PDO by an oxidoreductase, 1,3-propanediol dehydrogenase (Pdh). Both Gdh and Pdh have been studied extensively, with the best studied from *Klebsiella pneumonia*, a 1,3-PDO producing microbe. The DuPont process uses *K. pneumonia* genes cloned into *E. coli* for their industrial-scale fermentation process.

In some embodiments, a functionalizing polypeptide can comprise a glycerol dehydratase. In some embodiments, a functionalizing polypeptide can comprise a *K pneumonia* glycerol dehydratase. In some embodiments, a functionalizing polypeptide can comprise a propanediol dehydrogenase. In some embodiments, a functionalizing polypeptide can comprise a *K. pneumonia* propanediol dehydrogenase.

Biorecovery of Valuable Metals or Removal of Metal Pollutants using BIND. Metal removal and recovery are highly relevant for a number of industries, including mining, recycling, and water treatment. The BIND platform provides a method to display engineered binding proteins with high affinity and selectivity for specific metal ions and particles. The BIND platform represents a significant advancement over other biosorption techniques because it is able to display full-length proteins in high density and in a scalable manner. The use of recombinant proteins for these applications would be cost-prohibitive in most cases because of the production and purification protocols necessary to generate them. Contemplated herein are biofilm-based materials that can serve as a separations medium for metal ions and particles.

Engineering of probiotic *E. coli* to synthesize therapeutic biofilms. Contemplated herein are biofilm-based materials that are suitable for use inside the body. The BIND platform provides a means to program the adhesion of the biofilm-based material to biological tissues. Such materials would be able to control the residence time and localization of the biofilms inside the body. These materials would have the capability of establishing themselves at a specified location, altering the properties of the biological tissue through direct interaction of the curli nanofibers with the tissue, and secreting soluble biomolecules to alter local biological processes.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of a wildtype or native polypeptide, e.g. 110%, 125%, 150%, 175%, 200%, 500%, 1000% or more.

One method of identifying amino acid residues which can be substituted is to align, for example, CsgA from *E. coli* to a CsgA polypeptide from other species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. Such alignments are readily created by one of ordinary skill in the art, e.g. created using the default settings of the alignment tool of the BLASTP program, freely available on the world wide web at hypertext transfer protocol://blast-ncbi.nlm.nih.gov/. Furthermore, homologs of any given polypeptide or nucleic acid sequence can be found using BLAST programs, e.g. by searching freely available databases of sequence for homologous sequences, or by querying those databases for annotations indicating a homolog (e.g. search strings that comprise a gene name or describe the activity of a gene). Such databases can be found, e.g. on the world wide web at http hypertext transfer protocol://blast.ncbi.nlm.nih.gov/.

The variant amino acid or DNA sequence can be at least 90%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp, with default parameters set.

In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or note, has more than 100% of the activity of the wildtype enzyme, e.g. 110%, 125%, 150%, 175%, 200%, 500%, 1000% or more.

The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp, (available on the world wide web at hypertext transfer protocol://blast.ncbi.nlm.nih.gov) with default parameters set. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired apoptotic activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered CsgA polypeptide, comprising a CsgA polypeptide with a C-terminal display tag flanking the CsgA polypeptide;
   wherein the display tag comprises an activity polypeptide and a linker sequence;
   wherein the linker sequence is located N-terminal to the display polypeptide; and
   wherein the linker sequence comprises at least 6 amino acids.
2. The polypeptide of paragraph 1, wherein the linker sequence consists of glycine and serine residues.
3. The polypeptide of any of paragraphs 1-2, wherein the display tag and/or the activity polypeptide comprises a polypeptide selected from the group consisting of:
   Metal binding domain (MBD); SpyTag; graphene binding (GBP); carbon nanotube binding (CBP); gold binding (A3); CT43; FLAG; Z8; E14; QBP1; CLP12; and AFP8.
4. The polypeptide of any of paragraphs 1-2, wherein the activity polypeptide comprises a conjugation domain.
5. The polypeptide of paragraph 4, wherein the conjugation domain is selected from the group consisting of: SpyTag; biotin acceptor peptide (BAP); biotin carboxyl carrier protein (BCCP); and a peptide comprising a LPXTG motif.
6. A nucleic acid sequence encoding the polypeptide of any of paragraphs 1-5.
7. A vector comprising the nucleic acid sequence of paragraph 6.
8. An engineered microbial cell comprising the vector, nucleic acid sequence, or polypeptide of any of paragraphs 1-7.
9. The cell of paragraph 7, wherein the cell expresses an engineered CsgA polypeptide comprising an activity polypeptide comprising a conjugation domain.
10. The cell of paragraph 9, wherein the cell further comprises a nucleic acid sequence encoding a functionalizing polypeptide comprising a partner conjugation domain.
11. A population of cells comprising a first cell type and a second cell type, wherein the first cell type is a cell of paragraph 9 and the second cell type comprises a nucleic acid sequence encoding a functionalizing polypeptide comprising a partner conjugation domain.

12. A biofilm comprising the cell of any of paragraphs 8-11.
13. A biofilm produced by culturing the cells of any of paragraphs 8-11 under conditions suitable for the production of a biofilm.
14. The biofilm of paragraph 13, comprising the cells of any of paragraphs 8-11.
15. A composition comprising the polypeptide of any of paragraphs 1-6.
16. The composition of paragraph 15, wherein the composition comprises filaments comprising the polypeptide of any of paragraphs 1-6.
17. The composition of any of paragraphs 15-17, comprising a proteinaceous network.
18. The composition of any of paragraphs 15-18, wherein the composition further comprises additional proteinaceous biofilm components
19. The composition of any of paragraphs 15-19, further comprising the cell of any of paragraphs 8-11.
20. The use of the cell, composition, or biofilm of any of paragraphs 8-19, to display a polypeptide within the biofilm, with the composition, or on the cell surface.
21. The use of the cell, composition, or biofilm of any of paragraphs 8-19, in an application selected from the group consisting of:
   biocatalysis; industrial biocatalysis; immobilized biocatalysis; chemical production; filtration; isolation of molecules from an aqueous solution; water filtration; bioremediation; nanoparticle synthesis; nanowire synthesis; display of optically active materials; biosensors; surface coating; therapeutic biomaterial; biological scaffold; structural reinforcement of an object; and as a delivery system for therapeutic agents.

EXAMPLES

Example 1

Described herein is a method to genetically modify the major proteinaceous component of bacterial biofilms to display functional peptides, thus reprogramming biofilms for a wide variety of beneficial applications including but not limited to industrial biocatalysis, bioremediation, bioenergy, materials templating, and biosensing. This technology is based on the curli system of *E. coli*, which consists of cell-surface anchored amyloid fibrils that are made from the self-assembly of a secreted protein (FIGS. 1A-1F). The technology described herein demonstrates that functional peptide domains can be appended to the secreted protein so that, once it is assembled, the amyloid fibril network exhibits augmented functionality (e.g., binding to various biological and chemical entities). Furthermore, this extracellular matrix-peptide display technology can be adapted for the immobilization of any protein.

Results

Fusion Domains can be Displayed on Curli Nanofibers.

Many microbes produce biofilms as an extracellular matrix material to colonize various surfaces and protect themselves from environmental stresses. One of the major structural components of these biofilms is nanoscale fibers composed of proteins. The bacteria secrete these proteins into the extracellular milieu, where the protein monomers spontaneously self-assemble into a polymeric chain which is anchored on the cell surface. These protein nanofibers are known to exhibit amyloidogenic structural characteristics and are extremely robust. They have been shown to impart a number of evolutionary advantages, including mediating adhesion to surfaces, invasion of host cells, and sequestering toxic metals.[1-3] Most current biofilm research is focused on inhibiting or dispersing biofilms deleterious to human health. The formation of biofilms as an adhesion and persistence mechanism on almost any surface poses a great risk for infection in the biomedical and food industries[4]. Described herein is a platform technology which utilizes biofilms for beneficial applications. It is demonstrated herein that functional peptides can be engineered into biofilms by the successful expression and secretion of genetic fusions of fimbriae-forming nanofibers such as curli.

Key aspects of the technology described herein can include, but are not limited to: the ability to genetically program various physical, chemical, and biochemical functionalities into the protein structural component of a biofilm; a biofilm composed of curli nanofibers or any such similar extracellular self-assembling protein-based amyloid fibers; an engineered unit of the biofilm nanofiber composed of a self-assembling protein domain containing one or more curli unit or self-assembling domains, a spacer domain of variable length, and a peptide "activity" domain of arbitrary length on the C-terminus of the protein; the N-terminus of the protein can optionally additionally comprise various domains that allow periplasmic localization and/or protein secretion into the extracellular space; the peptide activity domain can be any peptide that allows for substrate adhesion, the binding to any biomolecule or chemical, has self-contained catalytic activity, is involved in catalytic activity in coordination with an externally localized protein, can template inorganic structures, can induce physiological responses in cells, can bind to ions in solution, can self-polymerize or polymerize with other molecules, is optically active, confers electrical conductivity, and/or leads to stimulus-responsive behavior. In some embodiments, proteins can be immobilized on the engineered curli biofilm by expressing on the curli nanofibers a peptide tag that specifically interacts with a protein domain to form a covalent or non-covalent complex. Any target protein fused to this interacting protein domain can thus be displayed on the biofilms by exposing the engineered curli-peptide tag biofilms to the fusion protein. This fusion protein can be expressed in cis or trans and used in various states of purity.

The curli system of *Escherichia coli* is composed of small protein monomers, CsgA, that are secreted by the cell and self-assemble extracellularly into highly robust amyloid nanofibers that are anchored to the cell surface by an outer-membrane bound homologous protein, CsgB.[5] The resulting curli nanofibers have a diameter of ~7 nm, form a tangled curly mass, and are resistant to boiling in detergent. Incubation of curli fibers in ~90% formic acid is required to dissociate the amyloid nanofiber into its monomers. We have demonstrated that it is possible to make genetic fusions to the CsgA protein while maintaining its ability to form extracellular curli fibers (FIG. 1A). This was accomplished by creating a panel of mutants (schematically shown in FIG. 1B, left) consisting of CsgA fused at the N- or C-terminus by various flexible linkers to a metal binding domain (MBD), a peptide domain from the *Pseudomonas* spp. known to bind strongly to stainless steel surfaces.[6] The csgA variants were cloned into plasmids and transformed into a strain of *E. coli* (LSR10) missing the wild-type csgA gene but containing the remaining curli processing machinery. Therefore, upon induction, amyloid formation could be attributed solely to the heterologously engineered CsgA fusion mutants. Congo Red (CR) staining of bacterial colonies on low-salt media is a standard colorimetric indicator for amyloid fibril formation, in which a red coloration of the bacteria indicates successful Curli fiber formation. The results of the insertion panel show that only the C3 fusion, which has the longest linker between the CsgA C-terminus and the MBD, is able to form an appreciable amount of amyloid fibers.

Figure 1B:
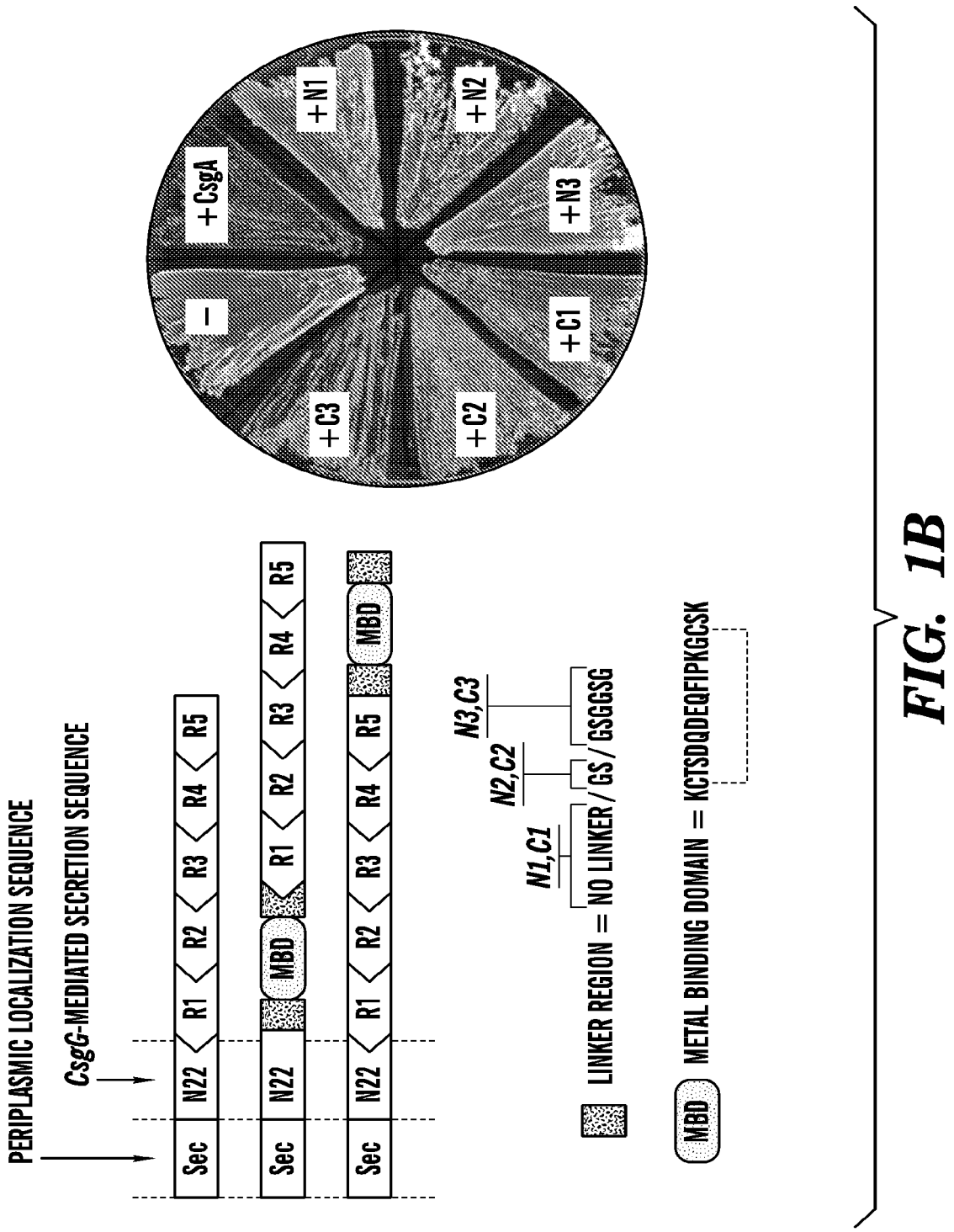
Figure 1D:
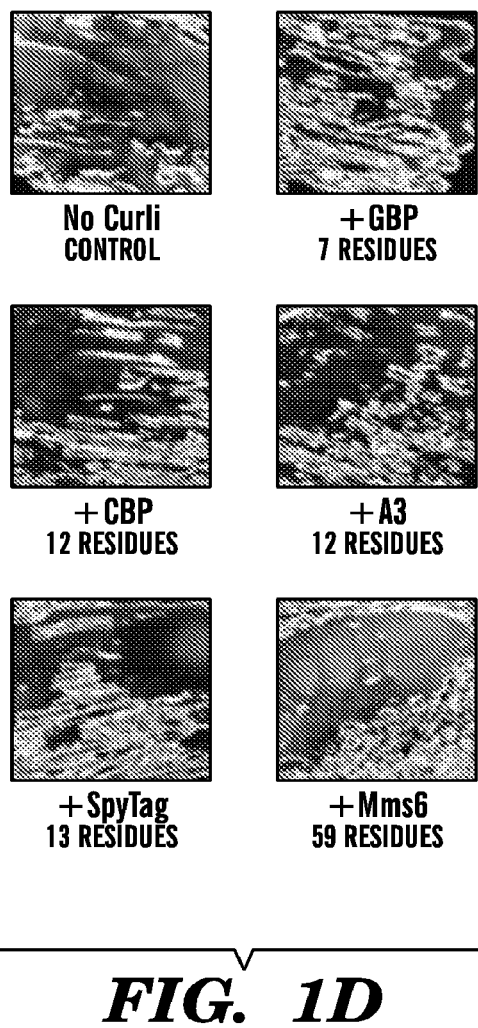
Figure 1E:
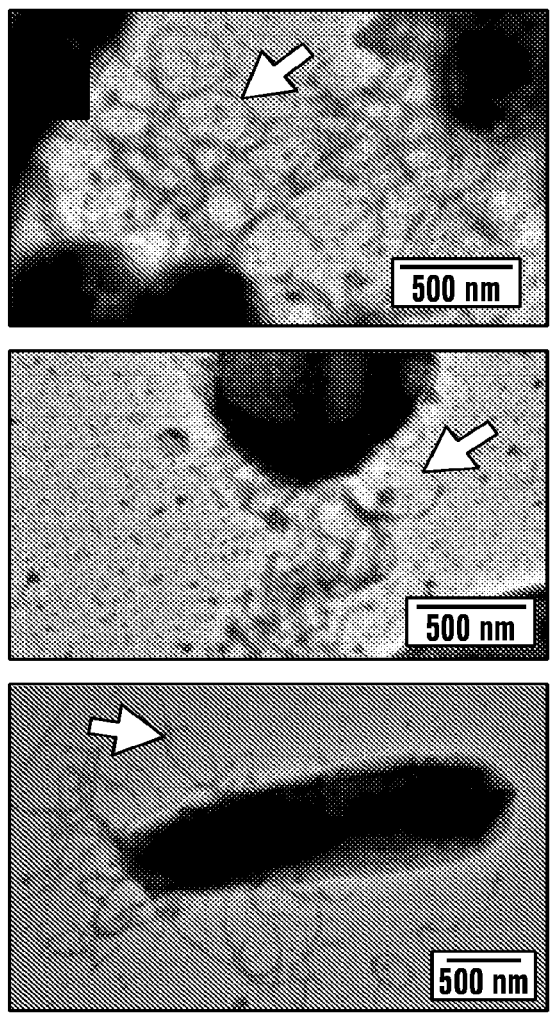
Figure 1F:
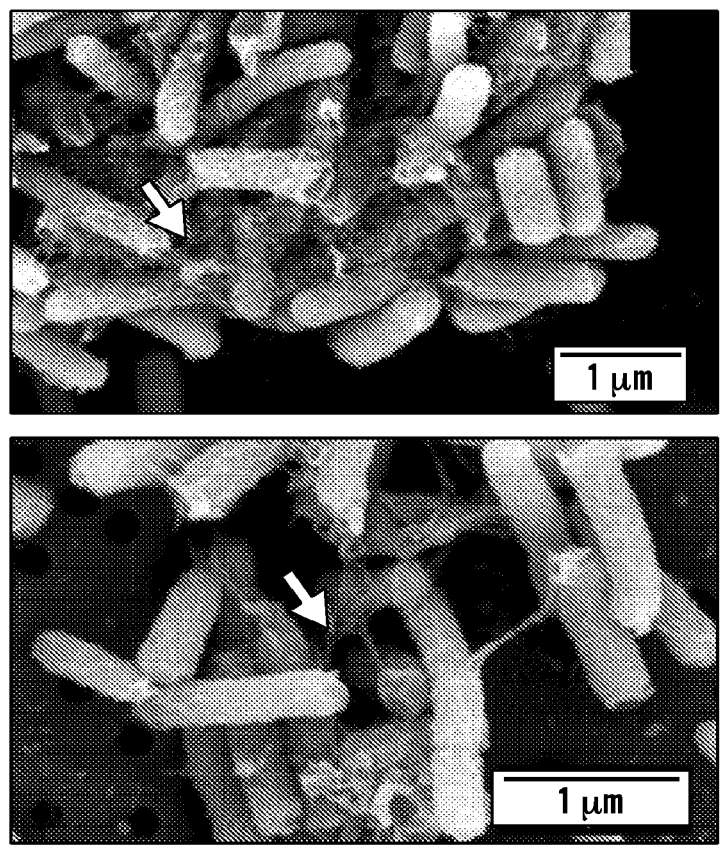

To test the extent of the functional domains that can be fused to the C-terminus of CsgA, a library of different functional peptides and protein domains ranging in size from 7 to 59 residues was selected and cloned into the C-terminal region, while retaining the flexible linker (FIG. 1C). FIG. 1D of the curli fusion constructs streaked onto CR plates indicates that various small functional peptides are tolerated by the curli machinery and form curli nanofibers as evidenced by CR staining, but the 59-amino acid Mms6 domain does not exhibit amyloid-positive CR staining. TEM and FE-SEM images visualizing the curli fibers that result from some of the CsgA fusion proteins support this data, with the MBD and SpyTag peptide fusions at the C3 insertion site producing visible nanofibers (FIGS. 1E-1F). These results demonstrate that 1) it is possible to make genetic fusions to CsgA while maintaining processing by the cellular curli machinery for secretion from the cell and assembly into amyloid fibers extracellularly, and 2) A C-terminal insertion site with a flexible linker is the most tolerant construct architecture for curli secretion and assembly.

Curli-Displayed Fusion Peptide Domains are Functional and can be Used as a Scaffold for the Presentation of Proteins.

Figure 2A:
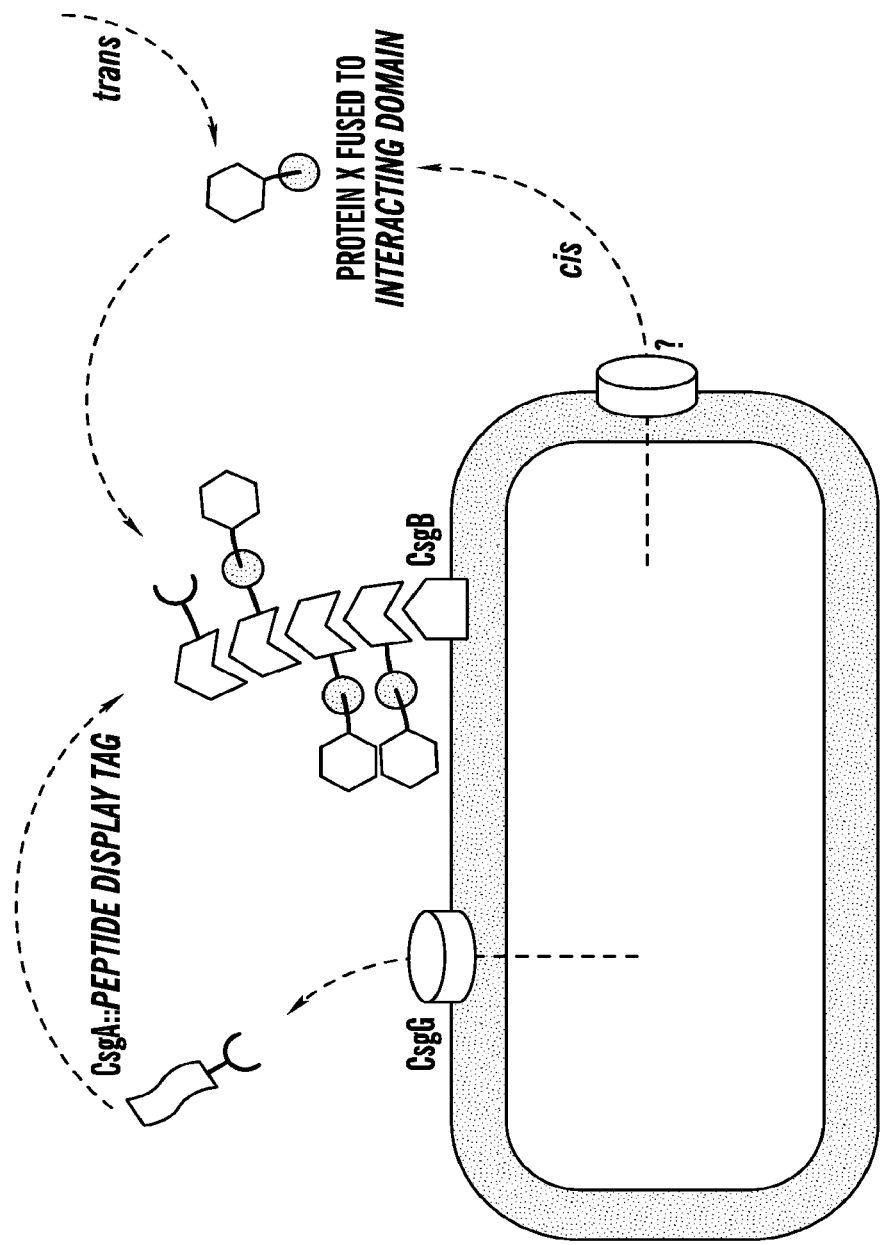
FIGS. 2A-2C depict the functionalization of curli fibers.
Figure 2B:
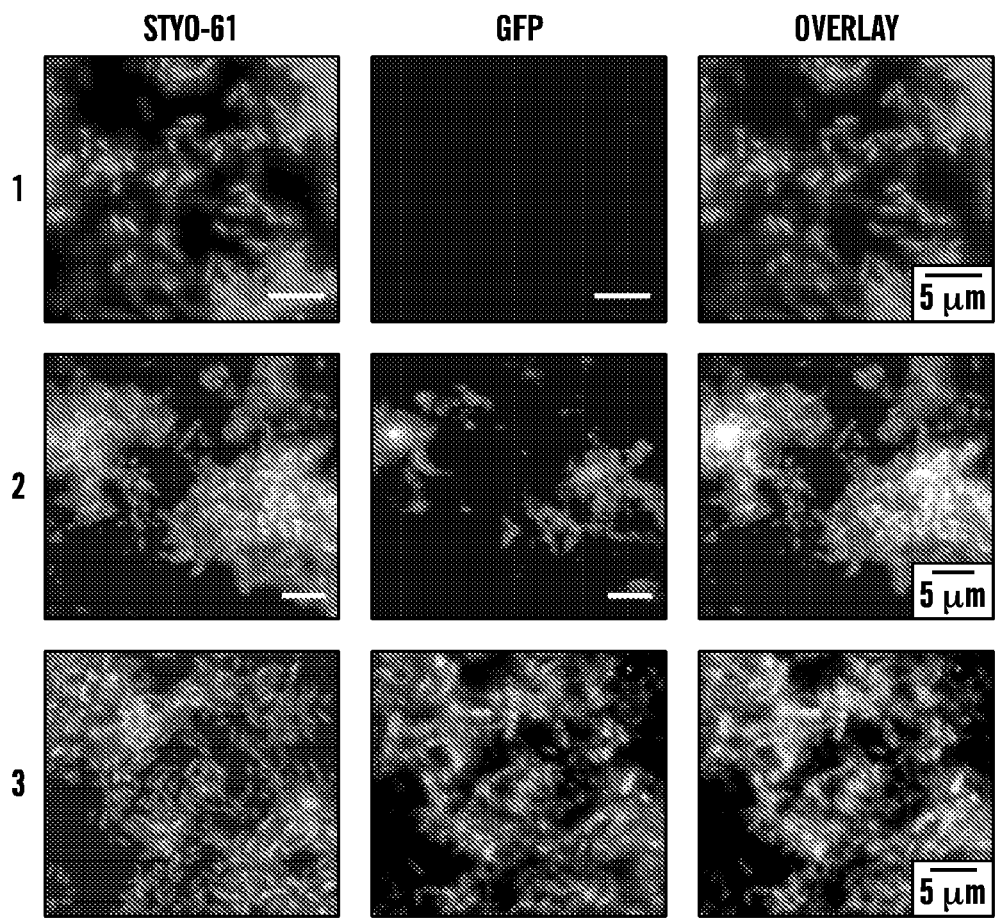

To test if the peptide domains are functional when displayed on the extracellularly assembled engineered curli nanofibers, a peptide tag that specifically interacts with a protein domain was expressed in the engineered curli system (FIG. 2A). This system is a recently demonstrated a covalent capture platform in which the protein domain (called "SpyCatcher", herein referred to as "SC".) is able to specifically and robustly form an isopeptide bond with the peptide tag (called "SpyTag", herein referred to as "ST".).[7] Thus a functionally displayed ST peptide on the curli biofilm will form an irreversible bond to exogenously added SC protein domain that can be fused to any target protein. A reporter fusion protein of a fluorescent protein (Venus) to the SC domain was designed, expressed, and purified. When this purified Venus-SC protein was added to the wild-type curli biofilm displaying no peptide, no localization of fluorescence to the biofilm was observed (FIG. 2B, Row 1). However, when bioengineered curli biofilm displaying the ST peptide was exposed to the Venus-SC protein, significant fluorescence localized to the biofilm was observed (FIG. 2B, Row 2). In contrast, a Venus-SC(E77Q) mutant that is unable to catalyze the covalent bond to the ST peptide does not display strong localized fluorescence (FIG. 2B, Row 3). These results demonstrate: 1) peptides displayed on curli nanofibers are expressed in a functional and accessible form, and 2) that target proteins can be immobilized on peptide-functionalized curli biofilms by fusing the target protein to a protein domain that interacts with a peptide which is displayed by our engineered curli biofilm technology.

Figure 2C:
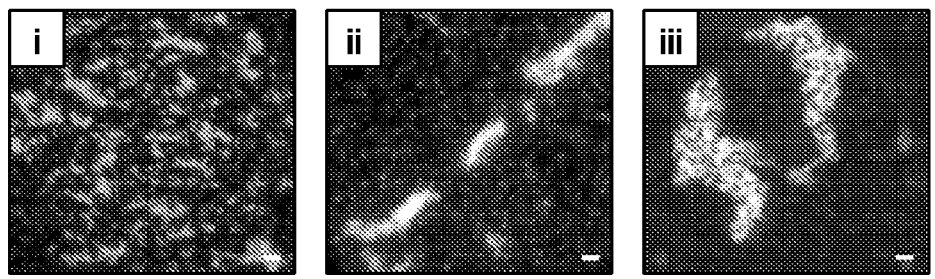

The purification of expressed proteins is not requisite for the protein immobilization strategy. Rather, like many of the affinity purification technologies currently used (i.e., chitin binding or Ni-NTA beads), the curli-SpyTag system can capture SpyCatcher-fusion proteins from cell lysate without extensive purification. In our experiments, Venus-SC and Venus-SC(E77Q) were expressed, cells lysed to release the proteins, the cell debris pelleted and the clarified cellular lysate added directly to the biofilms. As in the experiments described above utilizing purified protein, the Venus-SC is not captured by biofilms expressing curli without ST (FIG. 2C(i)), but is captured by curli-ST expressing biofilms (FIG. 2C(ii)). Again, the Venus-SC(E77Q) mutant is not captured by these curli-ST biofilms (FIG. 2C(iii)). This contributes to the robustness of the engineered curli platform as it combines purification and functional material synthesis into one step: the bacteria produces both the biofilm scaffold and the target protein to be immobilized. Applications as a disruptive technology for industrial biotransformation processes are contemplated, in which multiple complex bioreactor steps can be integrated into a single genetically programmed culture. This reduces the overall cost and increases the efficiency of system setup, which is a major concern for industry adaption[8]

The protein immobilization onto biofilm using the curli peptide display technology may use any of the various technologies consisting of an interacting peptide tag and protein domain, including but not limited to: the SpyTag-SpyCatcher system,[7] the BCCP-Biotin Ligase-Streptavidin system,[9] or Sortase-mediated Ligation.[10] The technology described herein is broadly applicable for the biofilm-immobilization of enzymatic, optically active, electronically active, biotemplating, structural, stimulus-responsive, and binding proteins or any combination thereof.

Applications

The curli system described herein is a biologically produced peptide-functionalized surface coating capable of being programmed to specifically immobilize another chemical or biological entity or to exhibit specific binding properties. The displayed peptide may possess intrinsic properties such as binding to other exogenously added functional components, such as inorganic nanoparticles (especially those with interesting opto-electronic properties or magneto-responsiveness), carbon-based nanostructures (i.e., graphene or nanotubes, which may confer conductivity), or environmental toxins (i.e., hormones or toxic metals). The engineered biofilms can also be used to display peptides that template the formation of inorganic or organic materials. Functionalizing the biofilm with peptides that specifically bind to different materials allows the surface coating of these materials in a genetically programmable manner. In addition, applications whereby the living biofilm is used to immobilize and present any arbitrary protein, as might be useful for applications in biocatalysis, biotemplating, or biosensing are specifically contemplated. In contrast to other engineered systems that serve the same purpose, the synthesis and assembly of the material described herein is accomplished entirely by the bacterial cell, which acts as a factory for the production of programmed nanomaterials.

Potential specific applications include:

Biologically-produced nanomaterials that have programmable optical, magnetoresistive or semiconductor properties from either the peptide/immobilized protein itself or by the induction of templated materials.

By displaying catalytic peptides or enzymes on the curli biofilm, a system for high-efficiency immobilized biocatalysis in which various immobilization substrates can be used for the adhesion of the biofilm and which can be used in any bioreactor design is contemplated.

The peptide/immobilized proteins can also encode for biologically active biomolecules that will allow the biofilm to act as a tissue scaffold or vaccine delivery material.

Expression of peptide/immobilized proteins that bind to or enzymatically neutralize environmental toxins such as synthetic hormones, small molecules, or toxic metals can be used as a biofilm-based technology for bioremediation.

By expressing peptides that are able to specifically bind to precious metals such as gold, silver, platinum, and rhodium on the biofilms described herein, there is a vast possible active surface area for the profitable recovery of such precious materials.

The curli nanofibers can be engineered as conductive nanowires for numerous advanced materials applications by the display of peptides/proteins that are inherently conductive, or by the templating/anchoring of materials that are conductive.

The use of bacteria to generate nanowires for energy storage based upon the expression on the curli biofilm of peptides capable of templating conductive or semi-conductive materials, such as FePO4.

Bacteria can be specifically engineered via the displayed peptide to bind strongly to specific substrates, such as steel, glass, or gold. Such material-specific binding can form the foundation of a biofilm-based biosensing technology.

The curli nanofiber matrix can also be engineered to display peptides/proteins that interact with other molecules in order to enhance or alter the mechanical properties of another material.

By engineering the curli to adhere to specific materials, the biofilm can act as a living coating capable of providing adaptive and regenerative benefits, such as biocatalysis on a wide variety of immobilization substrates, corrosion resistance to the material, enhanced biofilm coverage for microbial fuel cell applications, or act as an environmentally responsive organic(biofilm)-inorganic(substrate) material.

Discussion

Biofilms are used on large scales in technologies for bioremediation and waste water treatment:[1-13] The use of biofilms for still further applications, such as microbial fuel cells,[14-19] biocatalysis,[8, 20-24] and corrosion prevention.[25-27] has been investigated. However, these applications rely on the intrinsic capabilities of naturally occurring microbes. For example, biofilms used in the context of removing heavy metals from water samples employ soil bacteria that are known to have the capacity to sequester metal ions; microbes used in fuel cells are most often those that are known to naturally produce electroconductive extracellular components. One substantial drawback to these existing methods is that it requires a cell that is capable of internalizing the substrate to be bound or biocatalyzed. This severely limits the efficiency of the process by adding a kinetic diffusion barrier. By contrast, the technology describes herein provides a bacterial biofilm component (curli) whose capabilities have been enhanced or augmented with completely new ones based on a rational genetic engineering approach.

Although this circumvents barriers of substrate accessibility mentioned above, The curli-based peptide display system has a number of distinct benefits over traditional cell surface display systems[28-31]. In the technology described herein, each cell acts as a factory to generate engineered nanofibers, and therefore greatly increases the functional surface area of the scaffold available for the display of the peptides. In addition, the curli fibers are extremely stable and can exist even after the removal of the cells, whereas prior cell-surface display systems are vulnerable to harsh conditions which may cause lysis of the cells.

The technology described herein provides a programmable functionalized biofilm, including the immobilization of proteins, which is an advance over the prior art and greatly expands the potential applications of this platform technology. Further, the present technology is preferable to fimbrial display in that curli nanofibers form through the self-assembly of a single monomeric protein, CsgA, whereas the fimbriae systems The fact that the curli forms the major protein component of *E. coli* biofilms and is a simple genetic system composed of a single protein monomer provides distinct advantages to the present described engineered curli platform.

The technology described herein is contemplated to have a number of applications, including but not limited to, biocatalysis, metal recovery, and electrobiological applications. However, the engineered biofilms can be useful for any applications where surface coatings with programmable functions are required. In addition to acting as a material itself, the curli-based system can be useful as a screening tool to rapidly identify or even evolve self-assembling proteins with desired behaviors. The extracellular nature of the curli biofilm, its intrinsic high stability, and vast potential for a high-surface area material will make this technology highly valuable in various biocatalysis, bioremediation, and biomedicine applications.

REFERENCES

1. Giltner, C. L. et al. The *Pseudomonas aeruginosa* type IV pilin receptor binding domain functions as an adhesin for both biotic and abiotic surfaces. Molecular Microbiology 59, 1083-1096 (2006).
2. Duguid, J. P., Anderson, E. S. & Campbell, I. Fimbriae and adhesive properties in Salmonellae. The Journal of pathology and bacteriology 92, 107-138 (1966).
3. Hidalgo, G., Chen, X., Hay, A. G. & Lion, L. W. Curli Produced by *Escherichia coli* PHL628 Provide Protection from Hg(II). Applied and Environmental Microbiology 76, 6939-6941 (2010).
4. Hall-Stoodley, L., Costerton, J. W. & Stoodley, P. Bacterial biofilms: from the natural environment to infectious diseases. Nat Rev Microbiol 2, 95-108 (2004).
5. Hammer, N. D., Schmidt, J. C. & Chapman, M. R. The curli nucleator protein, CsgB, contains an amyloidogenic domain that directs CsgA polymerization. Proceedings of the National Academy of Sciences of the United States of America 104, 12494 (2007).
6. Davis, E. M., Li, D.-y. & Irvin, R. T. A peptide-stainless steel reaction that yields a new bioorganic-metal state of matter. Biomaterials 32, 5311-5319 (2011).
7. Zakeri, B. et al. Peptide tag forming a rapid covalent bond to a protein, through engineering a bacterial adhesin. Proceedings of the National Academy of Sciences 109, E690-7 (2012).
8. Rosche, B., Li, X. Z., Hauer, B., Schmid, A. & Buehler, K. Microbial biofilms: a concept for industrial catalysis? Trends in Biotechnology 27, 636-643 (2009).
9. Beckett, D., Kovaleva, E. & Schatz, P. J. A minimal peptide substrate in biotin holoenzyme synthetase-catalyzed biotinylation. Protein science: a publication of the Protein Society 8, 921-929 (1999).
10. Mao, H., Hart, S. A., Schink, A. & Pollok, B. A. Sortase-Mediated Protein Ligation: A New Method for Protein Engineering. Journal of the American Chemical Society 126, 2670-2671 (2004).

11. McNamara, C. J., Anastasiou, C. C., O'Flaherty, V. & Mitchell, R. Bioremediation of olive mill wastewater. International Biodeterioration & Biodegradation 61, 127134 (2008).
12. Valls, M. & De Lorenzo, V. Exploiting the genetic and biochemical capacities of bacteria for the remediation of heavy metal pollution. FEMS microbiology reviews 26, 327-338 (2002).
13. Wang, Y.-K. et al. Development of a Novel Bioelectrochemical Membrane Reactor for Wastewater Treatment. Environmental Science & Technology 45, 9256-9261 (2011).
14. Erable, B., Duteanu, N. M., Ghangrekar, M. M., Dumas, C. & Scott, K. Application of electro-active biofilms. Biofouling 26, 57-71 (2010).
15. MANSFELD, F. The interaction of bacteria and metal surfaces. Electrochimica Acta 52, 7670-7680 (2007).
16. Strycharz-Glaven, S. M., Snider, R. M., Guiseppi-Elie, A. & Tender, L. M. On the electrical conductivity of microbial nanowires and biofilms. Energy & Environmental Science 4, 4366 (2011).
17. Wang, Z.-W. & Chen, S. Potential of biofilm-based biofuel production. Applied Microbiology and Biotechnology 83, 1-18 (2009).
18. Yu, Y.-Y., Chen, H.-l., Yong, Y.-C., Kim, D.-H. & Song, H. Conductive artificial biofilm dramatically enhances bioelectricity production in *Shewanella*-inoculated microbial fuel cells. Chemical Communications 47, 12825 (2011).
19. Nevin, K. P., Woodard, T. L., Franks, A. E., Summers, Z. M. & Lovley, D. R. Microbial Electrosynthesis: Feeding Microbes Electricity To Convert Carbon Dioxide and Water to Multicarbon Extracellular Organic Compounds. mBio 1, e00103-10-e00103¬, 10 (2010).
20. Li, X. Z., Hauer, B. & Rosche, B. Single-species microbial biofilm screening for industrial applications. Applied Microbiology and Biotechnology 76, 1255-1262 (2007).
21. Li, X. Z., Webb, J. S., Kjelleberg, S. & Rosche, B. Enhanced benzaldehyde tolerance in *Zymomonas mobilis* biofilms and the potential of biofilm applications in fine-chemical production. Applied and Environmental Microbiology 72, 1639-1644 (2006).
22. Gross, R., Hauer, B., Otto, K. & Schmid, A. Microbial biofilms: New catalysts for maximizing productivity of long-term biotransformations. Biotechnology and Bioengineering 98, 1123-1134 (2007).
23. Tsoligkas, A. N. et al. Engineering Biofilms for Biocatalysis. ChemBioChem 12, 1391-1395 (2011).
24. Wood, T. K., Hong, S. H. & Ma, Q. Engineering biofilm formation and dispersal. Trends in Biotechnology 29, 87-94 (2011).
25. Zuo, R. Biofilms: strategies for metal corrosion inhibition employing microorganisms. Applied Microbiology and Biotechnology 76, 1245-1253 (2007).
26. Stadler, R. et al. First evaluation of the applicability of microbial extracellular polymeric substances for corrosion protection of metal substrates. Electrochimica Acta 54, 91-99 (2008).
27. Jayaraman, A., Sun, A. & Wood, T. Characterization of axenic *Pseudomonas fragi* and *Escherichia coli* biofilms that inhibit corrosion of SAE 1018 steel. Journal of applied microbiology 84, 485-492 (2011).
28. Li, D., Newton, S. M. C., Klebba, P. E. & Mao, C. Flagellar Display of Bone-Protein-Derived Peptides for Studying Peptide-Mediated Biomineralization. Langmuir: the ACS journal of surfaces and colloids 28, 16338-16346 (2012).
29. van Bloois, E., Winter, R. T., Kolmar, H. & Fraaije, M. W. Decorating microbes: surface display of proteins on *Escherichia coli*. Trends in Biotechnology 29, 79-86 (2011).
30. Wang, A. A., Mulchandani, A. & Chen, W. Whole-Cell Immobilization Using Cell Surface-Exposed Cellulose-Binding Domain. Biotechnology progress 17, 407-411 (2001).
31. Georgiou, G. et al. Display of heterologous proteins on the surface of microorganisms: from the screening of combinatorial libraries to live recombinant vaccines. Nature Biotechnology 15, 29-34 (1997).
32. Chapman, M. R. et al. Role of *Escherichia coli* curli operons in directing amyloid fiber formation. Science 295, 851-5 (2002).
33. Der Vartanian, M. et al. An *Escherichia coli* CS31A fibrillum chimera capable of inducing memory antibodies in outbred mice following booster immunization with the entero-pathogenic coronavirus transmissible gastroenteritis virus. Vaccine 15, 11120 (1997).
34. Der Vartanian, M. et al. Permissible peptide insertions surrounding the signal peptide-mature protein junction of the ClpG prepilin: CS31A fimbriae of *Escherichia coli* as carriers of foreign sequences. Gene 148, 23-32 (1994).
35. Méchin, M. C., Der Vartanian, M. & Martin, C. The major subunit ClpG of *Escherichia coli* CS31A fibrillae as an expression vector for different combinations of two TGEV coronavirus epitopes. Gene 179, 211-8 (1996).
36. White, A. P., Collinson, S. K., Banser, P. A., Dolhaine, D. J. & Kay, W. W. *Salmonella enteritidis* fimbriae displaying a heterologous epitope reveal a uniquely flexible structure and assembly mechanism. J Mol Biol 296, 361-72 (2000).
37. White, A. P. et al. High efficiency gene replacement in *Salmonella enteritidis*: chimeric fimbrins containing a T-cell epitope from *Leishmania major*. Vaccine 17, 2150-61 (1999)

Example 2

Because of their role in bacterial pathogenicity and persistence, the vast majority of research on biofilms has focused on preventing their formation and promoting their dispersal. However, this has resulted in an overlooked opportunity to develop biofilms as functional materials. Demonstrated herein is a new technology platform, Biofilm-Integrated Nanofiber Display (BIND), in which the display of functional peptides is genetically engineered on the curli system of *E. coli*, the major proteinaceous component of the biofilm matrix consisting of thin amyloidogenic nanofibers. Bacteria in such a system are contemplated as serving as a living foundry for the production, assembly, and post-processing of customized advanced biomaterials and programmable surface coatings. Herein, a fusion site in the structural curli gene csgA is identified that allows for the display of peptides while retaining the ability of secreted CsgA chimeras to self-assemble into curli fiber networks. A library of functional peptides with a range of sizes and secondary structures were recombinantly engineered into the curli biofilms, demonstrating the modularity and flexibility of the curli display system. Furthermore, the kinetics and stability of the BIND nanofibers are established and it is demonstrated that the peptides are fully displayed, as designed. Finally, the retention of peptide functionality in BIND biofilms was demonstrated in three broad applications: engineered adhesion, peptide catalysis, and protein immobilization.

INTRODUCTION

In nature, most bacteria exist as biofilm communities, residing in a self-generated protective nanoscale scaffold of proteins, sugars, lipids, and extracellular DNA that defends against environmental rigors[5]. Biofilm formation is essential for bacterial adhesion and colonization of both natural and man-made surfaces. Characterization of biofilms in the mid-20$^{th}$ century revealed their key role in microbial persistence and pathogenicity, which has recently led to an abundance of research on biofilm prevention and dispersal.[6,7] However, these highly evolved extracellular matrices hold untapped potential as a beneficial nanobiotechnology engineering platform. There is a significant body of work that investigates the use of biofilms for beneficial purposes such as wastewater treatment[8-10] and biotransformations[11-13], but these efforts focus on the use of naturally occurring organisms that happen to have evolved various desired qualities. Efforts to rationally engineer the structure of biofilms at the molecular level have, to our knowledge, been completely absent. To date, there exists no robust and broad technology for the facile engineering of biofilm components.

The presently described approach to controlling the molecular composition of biofilm-based materials relies on the curli system —a proteinaceous component of some *E. coli* biofilms. The curli system is composed of a small 13-kDa-protein monomer, CsgA, that is secreted by the cell and self-assemble into highly robust amyloid nanofibers that are anchored to the cell surface by a homologous outer-membrane protein, CsgB[14-16]. The resulting curli nanofibers have a diameter of ~7 nm and form a tangled curly mass that encapsulates the cells.[17] Curli biosynthesis is promoted by an operon that contains seven genes (csgA-G).[18] Of these, CsgA is the main structural component,[19] while the other proteins are involved in the nucleation of amyloid fibers (CsgB),[20] or the processing (CsgE, F),21, [22] secretion (CsgC, G)23, [24], and control of transcription (CsgD)[17] of CsgA. The curli system was selected for this technology because it exhibits several features that make it amenable to the type of materials engineering platform which is contemplated herein. First, the amyloid fibers formed by CsgA are extremely robust, being able to withstand boiling in SDS[25], increasing their potential utility in harsh environments. Second, since the extracellular fiber network is composed primarily of a single protein, its structural features can be easily controlled by manipulating a single gene. Finally, although analogous extracellular amyloid systems exist in other organisms, notably *Salmonella*26, [27] and *Pseudomonas*,[28] the curli system is by far the best studied, and the fact that it occurs natively in *E. coli* and consists of a single structural protein makes it highly genetically tractable. Although some of these other fimbriae systems have been investigated as potential vaccine delivery agents,[29] there has been no research into their use in other biofilm-based biotechnological applications.

Described herein is a strategy that referred to as "biofilm-integrated nanofiber display" (BIND), which allows the programming of an *E. coli* biofilm's functional properties by genetically appending functional peptide domains to the CsgA protein. After the new CsgA-peptide is secreted and assembled, the amyloid nanofiber network displays the peptide in very high density on its surface. The biofilm's function is then augmented according to the sequence of the displayed peptides. It is demonstrated herein that functional peptide domains of various lengths and secondary structures can be appended to CsgA without precluding the formation of curli fibers. Furthermore, the effect of peptide domain fusion on the self-assembly kinetics of the CsgA mutants is quantified. Lastly, it is demonstrated that the peptide domains maintain their function in the context of the biofilm after secretion and assembly.

Results

Design of BIND for Programmable Functionalized Biofilms

For the design of the BIND platform described herein, a number of considerations were taken into account. The system has to be genetically tractable and modular, allowing for the facile integration of any functional peptide domain into the biofilm. This precludes the use of the polysaccharide biopolymers that form the bulk of biofilm mass,[30,31] as their synthesis relies on multi-enzymatic pathways that are difficult to engineer.[32] Proteinaceous components of biofilms known as fimbriae, which form cell-anchored nanoscale protein fibers, were selected as the scaffold of choice. Of the fimbriae systems in bacteria, the curli system was chosen as these amyloid nanofibers are primarily composed of a single self-assembling protein, CsgA. This maximizes the representation of the functional domain in the assembled network and greatly simplifies the complexity of the system. Furthermore, this system is native to *E. coli*, providing a wealth of genetic tools and expression technologies to work with. Therefore, it was first decided to test fusions of the functional domain to the N- or C-terminus of CsgA.

C-Terminal Peptide Fusions to CsgA are Able to Form Curli Nanofibers

Figure 3:
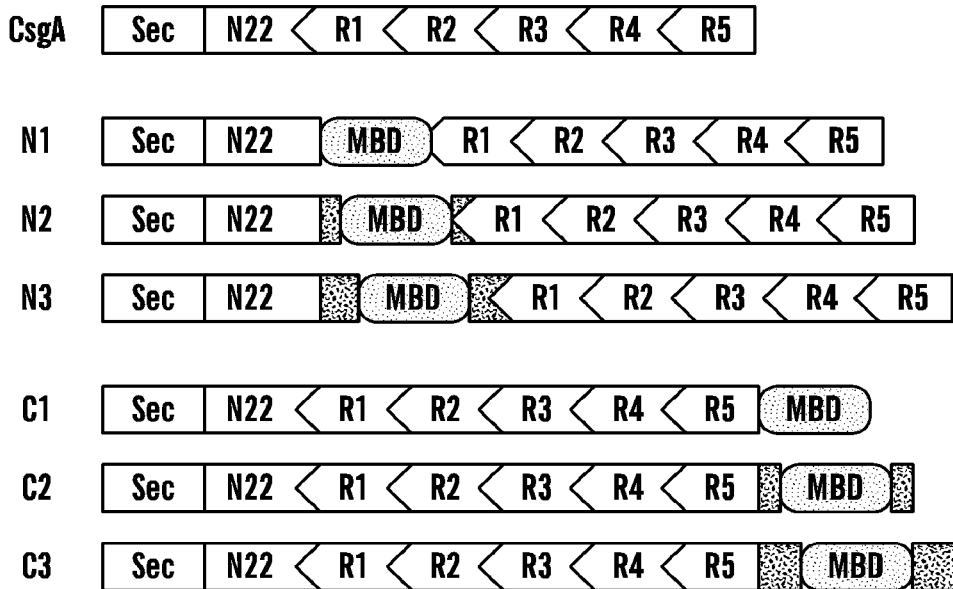
FIG. 3 depicts a schematic of a screen of acceptable sites and linkers for CsgA-peptide fusions. Genes encoding for the panel of CsgA chimeric proteins with either N- or C-terminal fusion sitess. The MBD (SEQ ID NO: 10) was fused to csgA either directly (N1, C1), with a short linker (N2, C2), or with a long linker (N3, C3) (GSGGSG (SEQ ID NO: 13). Sec and N22 sequences were maintained at the N-terminus to promote transport to the periplasmic and extracellular spaces, respectively.

The goal was to create genetic fusions to the CsgA protein that maintain its ability to form curli fibers. This was accomplished by creating a panel of mutants (schematically shown in FIG. 3A) consisting of CsgA fused at the N- or C-terminus to a metal binding domain (MBD), a peptide domain from the *Pseudomonas* spp. known to bind strongly to stainless steel surfaces.[33] Three variants were prepared for each terminus: MBD is linked to CsgA either directly, or with a short (GS) or long (GSGGSG (SEQ ID NO: 13)) flanking linker. The csgA variants were cloned into plasmids and transformed into a strain of *E. coli* (LSR10) missing the wild-type csgA gene, but containing the remaining curli processing machinery.[34] Therefore, upon induction, amyloid formation could be attributed solely to the heterologously engineered CsgA fusion mutants. As a readout of curli fiber production, Congo Red (CR) staining of bacterial colonies on low-salt media was used, which is a standard colorimetric indicator for amyloid fibril formation.[14] The results of the insertion panel show that only the C3 fusion, which has the longest linker between the CsgA C-terminus and the MBD, is able to form an appreciable amount of amyloid fibers (FIG. 1B). Other fusions are not tolerated, as evidenced by the lack of CR staining (FIG. 1B). TEM images visualizing the curli fibers that result from the CsgA fusion proteins support this data, with the C3 insertion site producing visible nanofibers (data not shown). These results clearly demonstrate that it is possible to make C-terminal genetic fusions to CsgA without inhibiting its secretion from the cell and extracellular assembly into amyloid fibers.

The C3 Design Allows for Modular Incorporation of Various Peptides into Curli Biofilms.

Figure 4:
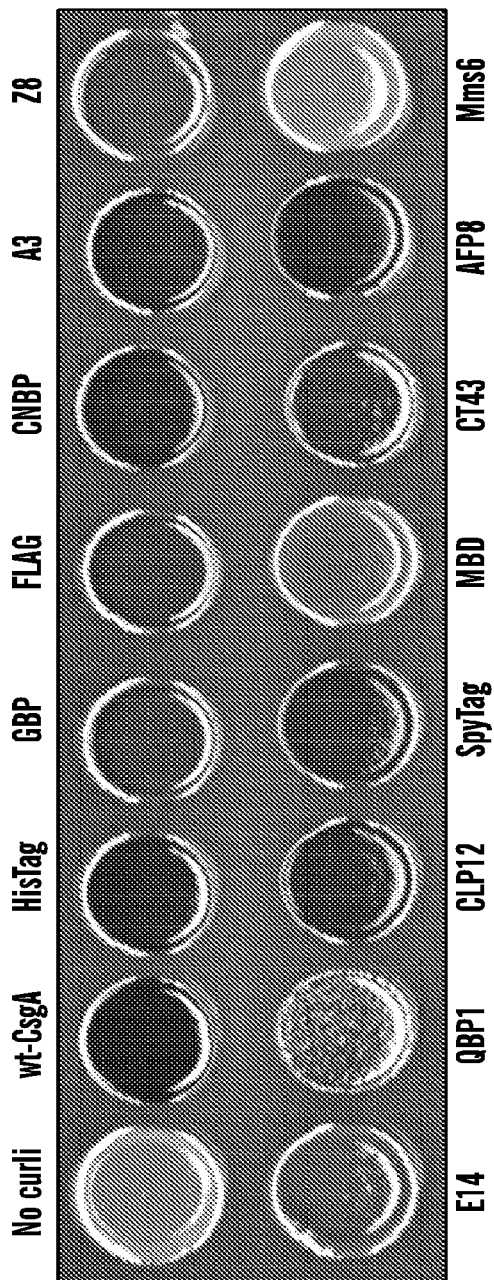
FIG. 4 depicts the modularity of C3 design for the design of BIND biofilms displaying various functional peptides. A panel of peptide domains was chosen to span a range of sizes, secondary structures, and functions. Each peptide was genetically fused to the C-terminus of CsgA through a 6-amino acid flexible linker Spotted cultures were grown for 48 hours on YESCA-CR plates.

To test the modularity of the functional domains that can be fused to the C-terminus of CsgA, a library of peptide domain fusions ranging in size from 7 to 59 amino acids while maintaining the 6 amino acid flexible linker from C3 was created (Table 1). The library also represents different secondary structures, as most of the peptides are not designed to exhibit any defined conformation, while MBD and Mms635 contain intramolecular disulfide bonds, which should lock them into a more rigid conformation. Finally, the library members were designed to span a range of functions that might be potentially useful in future applications of the BIND system to various technologies, including capturing proteins[36] and binding to inorganic nanoparticles[37-39] and surfaces.[33] The library members were cloned into LSR10 cells and probed for the formation of curli-based amyloid networks by CR staining. Positive CR staining (FIG. 2A) and quantitative analyses (FIG. 4) for most of the library members suggests that small peptide fusions were tolerated by the curli export machinery and successfully assembled into extracellular amyloid networks. The only mutant for which there was no positive staining was the 59-amino acid Mms6 domain. CsgA is thought to be transported across the outer membrane by the CsgG complex as an unfolded conformer[15]. Without wishing to be limited by theory, given that the pore size of the CsgG complex is estimated to be ~2 nm,[24] this suggests that larger folded domains may not be compatible with the curli export machinery.

TEM imaging of the modified curli biofilms suggests that the CsgA-peptide fusions assemble into nano-scale fibers similar to those observed for wt-CsgA (data not shown). The fibers display a characteristic tangled curly morphology and appear to be closely associated with the cell surface. The TEM images were intentionally obtained with diluted samples so that the nanostructure of the fibers could be easily discerned. The fibers in these images that appear to be fully extended are likely an artifact of the drying process during sample preparation and do not represent the native fiber morphology. Furthermore, SEM imaging shows that the modified curli biofilms can be very dense and several cell layers thick (data not shown) while maintaining a highly interconnected network of fibers between cells.

In Vitro Self-Assembly Kinetics of CsgA-Peptide Fusions.

In order to determine the effect of peptide domain fusion on the self-assembly of CsgA, several variants were selected for purification and assembly studies in vitro. For purification purposes, the CsgA-peptide fusions were appended to a His-tag followed by an enterokinase cleavage sequence. The purification sequences were inserted in place of the Sec tag such that the proteins would not be exported to the periplasm and after affinity purification from cell lysates, the enterokinase cleavage yielded proteins that were identical to those secreted by the corresponding LSR10 transformants after processing of the native Sec tag[40]. The purified proteins can monitored for their assembly kinetics using an established thioflavin T (ThT) assay.

Functionality of Peptides Displayed with BIND.

Figure 5A:
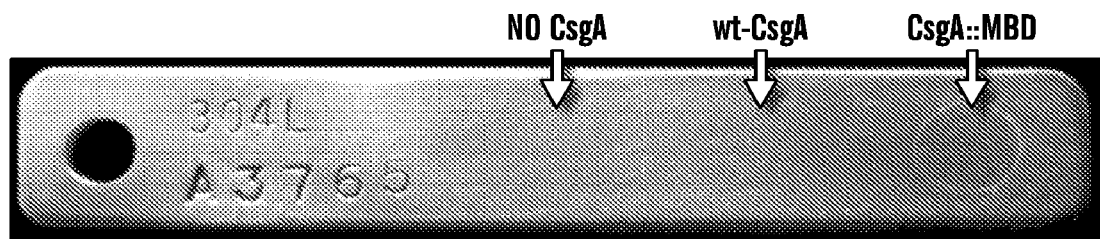
FIGS. 5A-5D demonstrate the programmed adhesion of MBD-BIND biofilms to 304L stainless steel.
Figure 5B:
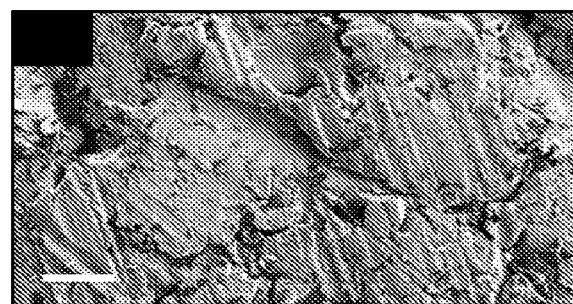
Figure 5C:
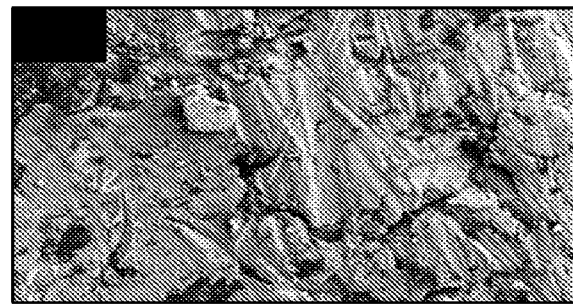
Figure 5D:
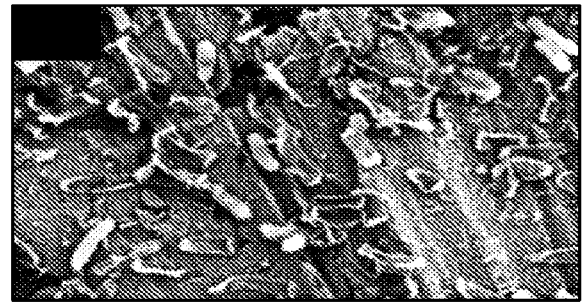

The BIND system is capable of introducing a variety of novel functions to curli-based biofilms. Therefore, in addition to confirming secretion and assembly of CsgA-peptide chimeras, it was also sought to demonstrate that the fused peptide domains maintain their cognate functions in the context of the fully formed biofilms. Accordingly, two peptides were selected from Table 1 (MBD and SpyTag) and their ability to augment biofilm performance was tested. MBD was chosen because its affinity for steel should enhance the adhesion of curli-based biofilms to stainless steel surfaces. To test this hypothesis, LSR10 cells expressing the CsgA-MBD mutant were grown in culture and, after induction, spotted onto stainless steel 304L coupons and allowed to dry in air. The same procedure was followed with cells expressing wt-CsgA and no CsgA as negative controls. Each coupon included an array of three spots —one from each culture. The coupons were then subjected to vigorous washing by submerging them in aqueous buffer and vortexing (FIG. 5A). Biofilms composed of the CsgA-MBD fusion clearly withstood the washing procedure, while those expressing wt-CsgA or no CsgA were easily washed off the surface (FIGS. 5B-5D). Based on this data, it is concluded that the adhesion of curli-based biofilms to non-natural surfaces can be artificially enhanced by appending peptide domains that have been pre-selected to exhibit a desired function.

Figure 6A:
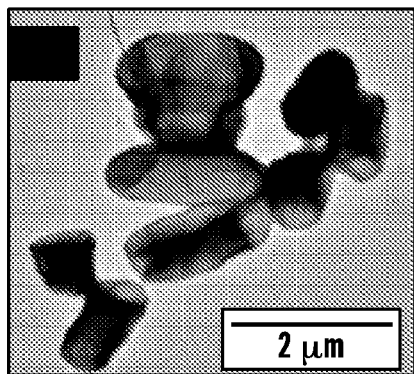
FIGS. 6A-6F demonstrate the covalent immobilization of full-length proteins onto curli biofilm using the SpyTag-SpyCatcher system. TEM and SEM images of PHL628 (AcsgA) strains expressing no curli (6A), wild-type CsgA (FIGS. 6B-6C), and the SpyTag-BIND biofilms (FIGS. 6D-6E).
Figure 6B:
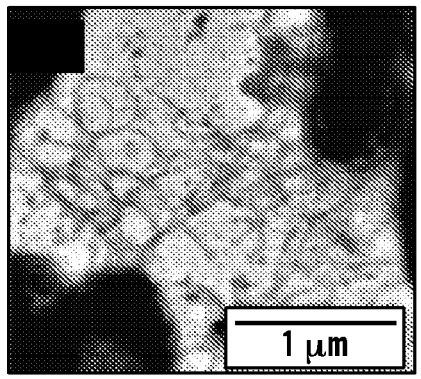
Figure 6C:
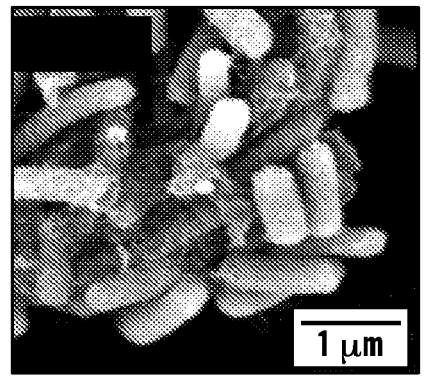
Figure 6D:
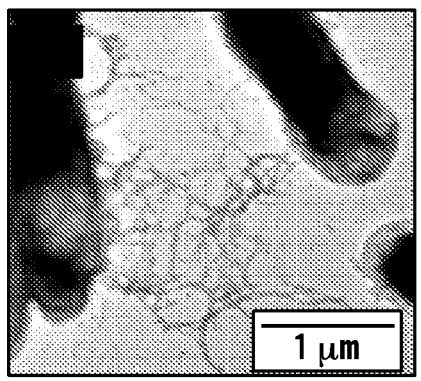
Figure 6E:
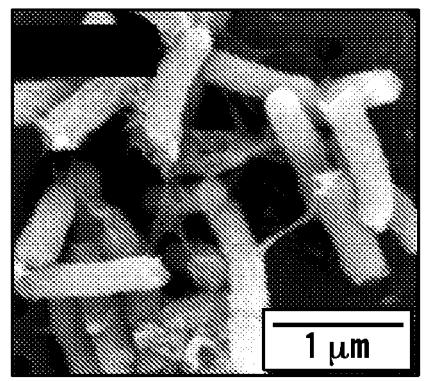
Figure 6F:
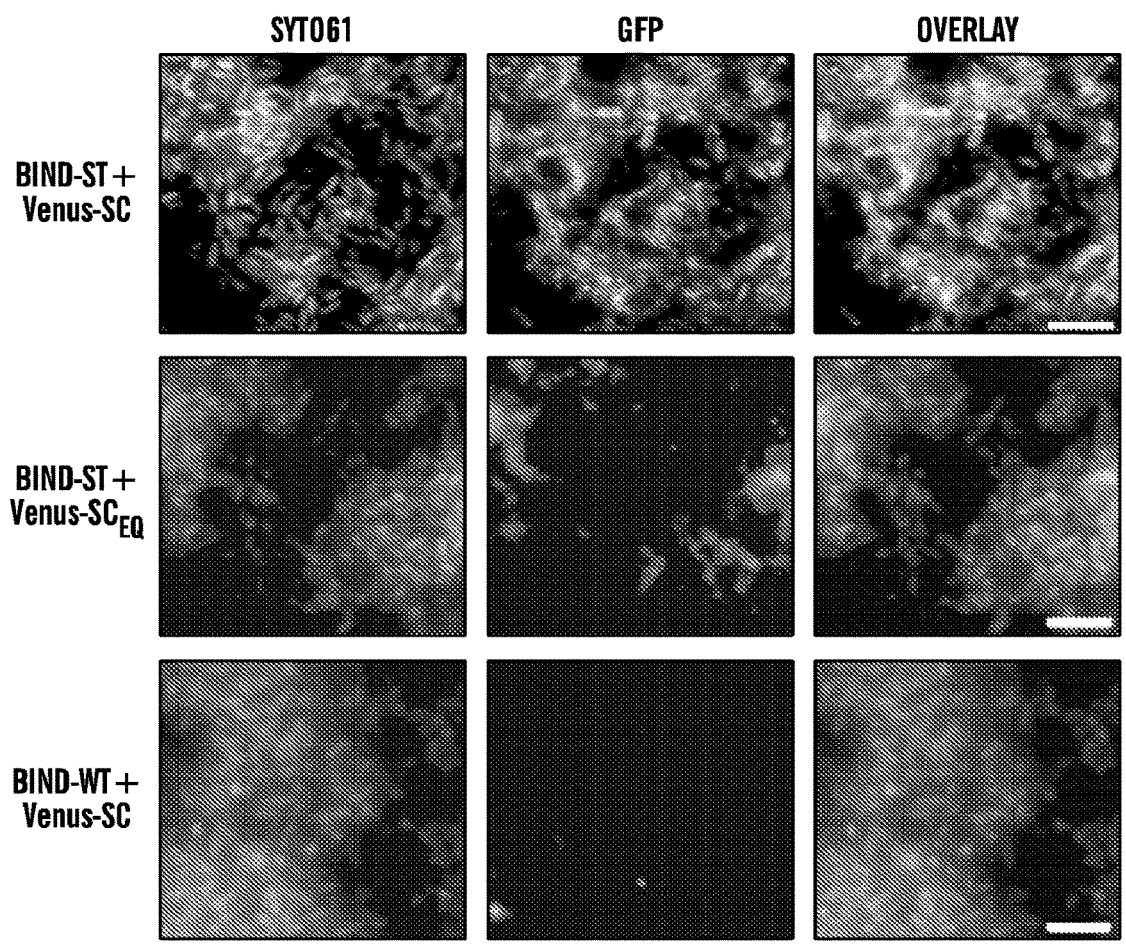

As a second demonstration of the utility of the BIND system, the CsgA-SpyTag mutant was investigated as a means to immobilize full-length proteins to the curli matrix. The SpyTag-SpyCatcher system is a recently developed strategy for protein capture that uses a CnaB2 protein that has been split into a 13 amino acid peptide (SpyTag) and a 15-kDa protein (SpyCatcher).[36] When brought together, the two fragments catalyze the formation of an intermolecular isopeptide bond. It was sought to use this strategy to circumvent the apparent size limitations of the curli export machinery by enabling covalent bond formation between the curli network and larger proteins using completely genetically encodable components. Accordingly, biofilms displaying containing the CsgA-SpyTag chimera were formed on a surface-modified glass substrate using PHL628 cells, an E. coli strain that has been engineered to overproduce CsgA. A SpyCatcher-Venus fusion protein was used to probe for the presence and functionality of the SpyTag domain. Venus is a green fluorescent protein variant with enhanced optical properties. The glass-immobilized biofilms were treated with a nucleic acid stain (SYTO 61, Invitrogen) to test for the presence of cells. Subsequently, they were treated with a solution containing either SpyCather-Venus, or SpyCatcherEQ-Venus, a mutant in which the covalent bond formation has been abolished. Following extensive washing steps, the biofilms were imaged using fluorescence microscopy. Only the proper combination of biofilms expressing the CsgA-SpyTag and treatment with SpyCatcher-Venus resulted in significant co-localization of the two fluorescent signals (FIG. 6F). Biofilms expressing wt-CsgA were unable to capture the fluorescent protein. Similarly, biofilms expressing CsgA-SpyTag did not exhibit green fluorescence when treated with the non-functional SpyCatcherEQ-Venus mutant. Together these results suggest that SpyTag peptide can be fused to CsgA and maintain its functionality after formation of the curli network Discussion The straightforward self-assembling system presented herein allows for the precise molecular control of bacterial extracellular matrix composition by genetic engineering and establishes a platform for the creation of functional bionanomaterials from living systems and perhaps even living functional materials. The advantages of such a synthetic biology platform are numerous: curli fibers can be engineered to display a variety of peptides with useful features, such as binding to or biotemplating the synthesis of inorganic materials, enhancing biofilm adhesion to particular surfaces, or providing a scaffold-like surface coating for the immobilization of other biomolecules. The biofilm itself is a "green" (i.e., environmentally friendly) material in that it is made biosynthetically and requires no petroleum-derived raw building blocks. Additionally, the biofilm has the capacity to be a self-generating and self-repairing renewable material.

Surface modification and functionalization is ubiquitous in nearly all aspects of our society. However, the use of biologically-derived surface coatings are lacking. Life has evolved a highly efficient coating strategy that was an early evolutionary adaptation enabling the bacterial colonization of surfaces[41]. Current applications of biofilms for applied technology utilize naturally occurring biofilms or co-cultures of biofilm-forming bacteria[42] to generate the desired functionality for thin-film biocatalysis or bioremediation. These applications remain limited and the adoption of biofilm-based technology in other industries is greatly hindered by an inability to program biofilm functionality and control the temporal dynamics of biofilm formation.

The curli system of E. coli plays a central role in host-cell adhesion of enteropathogenic strains and is critical for the formation of biofilms[25]. Curli has been extensively studied as a model system for functional bacterial amyloids[18] as well as for the development of biofilm-inhibiting compounds[43]. The curli system is demonstrated herein to be ideal as a programmable biofilm platform as it is predominantly composed of a single genetically programmable unit, the self-assembling CsgA proteins.

Materials And Methods

Cell Strains and Plasmids.

All cloning and protein expression was performed in Mach1™ (Invitrogen) and Rosetta™ cells (EMD), respectively. The csgA gene was isolated from E. coli K-12 genomic DNA and cloned into pBbE1 a, a ColE1 plasmid under control of the Trc promoter[44]. Expression vectors were constructed using pET30a plasmids (EMD), with the native N22 region of the CsgA protein cloned immediately after the enterokinase cleavage site. Peptide insert regions were either fully synthesized (Integrated Dna Technologies) or PCR-generated by overlap extension. All cloning was performed by using isothermal Gibson Assembly as described[45] and verified by DNA sequencing.

Curli Biofilm Formation

To produce curli, LSR10 cells or PHL628 cells were transformed with pBbE1a plasmids encoding for CsgA or CsgA-peptide fusions. As a negative control, cells were transformed with empty pBbE1a plasmid. The cells were then streaked or spotted onto YESCA-CR plates, containing 10 g/L of casamino acids, 1 g/L of yeast extract, and 20 g/L of agar. All media components were from Fisher. The plates were supplemented with 100 mg/mL of ampicillin, 0.5 mM of IPTG, 25 mg/mL of Congo Red and 5 mg/mL of Brilliant Blue G250. The plates were then incubated for 48 hours at 25° C. and then imaged to determine the extent of Congo Red binding. For the spotted plates, the transformants were grown in YESCA liquid media supplemented with 100 mg/mL of ampicillin and 0.2 mM of IPTG for 48 hours at 25° C. before spotting 20 mL onto YESCA-CR plates. This same YESCA liquid induction procedure was used to prepare samples for CsgA purification, and electron microscopy.

Quantitative Congo Red Binding Assays

Determination of Congo Red binding was adapted from previously published methods. Briefly, transformant cultures grown on YESCA plates for 48 hours at 25° C. were scraped and resuspended gently in PBS. The cell resuspention was adjusted to an OD600 of 3. To 1 mL of this, a Congo Red solution was added to a final concentration of 0.001% and allowed to incubate at 4° C. for 1 hour. The cells were then pelleted and the 490 nm absorbance of 200 μL of the supernatant was measured in a BIOTEK H1 microplate reader. The amount of Congo Red binding was determined as the subtractive amount of this measurement against a PBS+Congo Red control. All samples were performed in triplicate.

Chimeric CsgA Purification

Rosetta™ cell transformants were grown in LB until mid-log phase and induced with 0.2 mM IPTG for 3 hours. The cells were pelleted and then frozen at −20° C. for subsequent purification. The pellets were thawed and lysed in BugBuster Protein Extraction Reagent (EMD), 1 mg/mL Lysozyme, 50 μg/mL DNase, and protease inhibitors (Roche). After 30 minutes, the lysate was diluted into a solution of 8 guanidine hydrochloride, 250 mM NaCl, and 50 mM Tris at a pH of 7.5 and incubated for 16 hours to dissolve aggregates. Any insoluble mass was pelleted by centrifugation at 18,000 rpm for 30 minutes, the clarified lysate was filtered through a 0.22 micron filter, and then incubated with Ni-NTA resin (Qiagen) for 2 hours. The protein-bound resin was then washed with 8 guanidine hydrochloride, 250 mM NaCl, 0.1% TRITON™ X-100, 1 mM DTT, and 50 mM Tris (pH of 7.5) and eluted with the same buffer supplemented with 200 mM imidazole. The eluate was dialyzed into EK cleavage buffer (1M Urea, 20 mM methylamine, 50 mM Tris, pH 7.5) and then incubated with 3 μg of enterokinase (Roche) for 24 hours. The cleaved CsgA protein was then lyophilized, treated with 100 μL of HFIP to dissolve any curli fibers, and stored as a dried powder.

ThT Kinetic Assay

Immediately before the ThT assay, the cleaved, HFIP-treated protein was resolubilized into 8M guanidine hydrochloride, 250 mM NaCl, 0.1% TRITON™ X-100, and 50 mM Tris at a pH of 7.5. This solution was FPLC purified on a SEPHADEX® G75 gel-filtration column to remove dimers and oligomers. The fraction containing the monomeric CsgA fusions were then desalted and the concentration determined by UV absorbance. The ThT assay was immediately performed with 30 μM of the CsgA fusion or wild-type protein with 40 μM ThT; the fluorescence was measured in a SpectramaxM2 plate reader at 438ex/495em.

TEM and SEM

Curliated wildtype or BIND cell samples were either directly taken from induced YESCA cultures or scraped from YESCA-CR plates and resuspended in Millipore H2O. For TEM analysis, 5 mL of the sample was spotted onto formvar-carbon grids (Electron Microscopy Sciences), washed twice with Millipore H2O, and stained for 15 seconds with 1% uranyl formate before analysis on a JEOL 1200 TEM. For SEM analysis, samples were applied to Nucleopore filters under vacuum, washed with Millipore H2O and fixed with 2% glutaraldehyde+2% paraformaldehyde overnight at 4° C. The samples were then washed in Millipore H2O, dehydrated with an increasing ethanol step gradient, and dried using an hexamethyldisilazane step gradient before gold sputtering and analysis on a Zeiss Supra 55VP™ FE-SEM.

Immunogold TEM

For anti-FLAG immunogold labeling of the BIND cells displaying the FLAG tag, the cells were first adhered to the TEM grid as described above. Then, the grids were washed 3× in blocking buffer (PBS+1% BSA), floated on a drop containing a 1:1000 dilution of primary anti-FLAG murine antibody in PBS for XX minutes, washed in blocking buffer again, and then floated on a drop of 1:1000 diluted anti-mouse 15 nm gold-conjugated antibody. After a final 3× wash in PBS and then Millipore H2O, the grids were stained with 1% uranyl formate for 15 seconds and imaged on a JEOL 1200 TEM.

SpyCatcher-Venus Construction and Expression

Rosetta™ cells containing pDEST14-SpyCatcher-Venus were grown up in 5 mL overnight cultures in LB at 37 C with 100 mg/L ampicillin 500 mL cultures supplemented with ampicillin were inoculated with the overnight culture and grown up for 6 h at 37 C until an OD of 0.6. SpyCatcher-Venus expression was induced with 0.5 mM IPTG and allowed to express overnight at 18 C. Cells were harvested and lysed and SpyCatcher-Venus was purified on a Ni-NTA column. Protein was collected, buffer exchanged into 50 mM phosphate buffer 50 mM NaCl pH 7, concentrated and stored at −80 C until further use.

Fluorescent Biofilm Imaging

Fluorescent images were taken in epifluorescence mode on a Leica TIRF DM16000B instrument. Glass cover slips (No: 1.5) were plasma activated for 30 s each. Slides were immersed in 0.01 w/v % PLL solution for 2 h and then were placed in 60 C incubator for 2 h. PHL628 WT and CsgA-SpyTag(ST) cells were grown up in 20 mL cultures for 6 h at 37 C in YESCA broth containing 100 mg/L ampicillin until an OD of 0.6. Coverslips were dropped into the cultures and curli expression and biofilm formation were induced with 0.5 mM IPTG and 3% DMSO. Cultures were shaken at 25 C and 150 rpm for 48 h. Slides were removed from the cultures and washed 3×20 min in wash buffer (1x PBS with 0.5% TWEEN® 20). After the washes, 0.5 mL of 1 mg/mL Venus-SpyCatcher or Venus-SpyCatcher(EQ) solution (1×PBS, 1% BSA, 0.5% TWEEN®) was added to slides. The biofilms were incubated for 1 h and then washed 2×20 min with wash buffer. The biofilms were then stained with SYTO 61 (10 uM) for 20 min and washed with wash buffer 2×15 min shaking at 150 rpm. Slides were then imaged in epifluorescence mode with 60× and 100× oil lenses.

REFERENCES

1. Pasteur, L., Germ, Theory, And, Its, Applications, To, Medicine, And, Surgery, Comptes(rendus(de(l'Academie (des(Sciences, (lxxxvi., 1037-43, (1878),
2. Koch, R, Untersuchungen, Über, die, Aetiologie, der, Wundinfectionskrankheiten, (F. C., Vogel, Leipzig, 1878),
3. Morrow, J. F. et al. Replication and transcription of eukaryotic DNA in *Escherichia coli. Proc Natl Acad Sci USA* 71, 1743-7 (1974).
4. Lobban, P. (Stanford University, 1972).
5. Flemming, H C & Wingender, J. The biofilm matrix. *Nat Rev Microbiol* 8, 623-33 (2010).
6. Römling, U. & Balsalobre, C. Biofilm infections, their resilience to therapy and innovative treatment strategies. *Journal of internal medicine* (2012).
7. Wood, T. K., Hong, S. H. & Ma, Q. Engineering biofilm formation and dispersal. *Trends in Biotechnology* 29, 87-94 (2011).
8. Singh, R., Paul, D. & Jain, R. K. Biofilms: implications in bioremediation. *Trends Microbiol* 14, 38997 (2006).
9. Perelo, L. W. Review: In situ and bioremediation of organic pollutants in aquatic sediments. *J Hazard Mater* 177, 81-9 (2010).
10. Verhagen, P., De Gelder, L. & Boon, N. Biofilm based bioremediation strategies for the treatment of pesticide waste streams. *Commun Agric Appl Biol Sci* 76, 239-43 (2011).
11. Gross, R., Hauer, B., Otto, K. & Schmid, A. Microbial biofilms: new catalysts for maximizing productivity of long-term biotransformation. *Biotechnol Bioeng* 98, 1123-34 (2007).
12. Tsoligkas, A. N. et al. Engineering biofilms for biocatalysis. *Chembiochem* 12, 1391-5 (2011).
13. Halan, B., Buehler, K. & Schmid, A. Biofilms as living catalysts in continuous chemical syntheses. *Trends Biotechnol* 30, 453-65 (2012).
14. Chapman, M. R. et al. Role of *Escherichia coli* curli operons in directing amyloid fiber formation. *Science* 295, 851-5 (2002).
15. Wang, X., Smith, D. R., Jones, J. W. & Chapman, M. R. In vitro polymerization of a functional *Escherichia coli* amyloid protein. *J Biol Chem* 282, 3713-9 (2007).
16. Wang, X. & Chapman, M. R. Sequence determinants of bacterial amyloid formation. *J Mol Biol* 380, 570-80 (2008).
17. Barnhart, M. M. & Chapman, M. R. Curli Biogenesis and Function. *Annual Review of Microbiology* 60, 131-147 (2006).
18. Chapman, M. R. Role of *Escherichia coli* Curli Operons in Directing Amyloid Fiber Formation. *Science* (New York, N.Y.) 295, 851-855 (2002).
19. Dueholm, M. S. et al. Fibrillation of the major curli subunit CsgA under a wide range of conditions implies robust design of aggregation. *Biochemistry* (2011).
20. Hammer, N. D., Schmidt, J. C. & Chapman, M. R. The curli nucleator protein, CsgB, contains an amyloidogenic domain that directs CsgA polymerization. *Proceedings of the National Academy of Sciences of the United States of America* 104, 12494 (2007).
21. Nenninger, A. A. et al. CsgE is a curli secretion specificity factor that prevents amyloid fibre aggregation. *Molecular Microbiology* 81, 486-499 (2011).
22. Nenninger, A. A., Robinson, L. S. & Hultgren, S. J. Localized and efficient curli nucleation requires the chaperone-like amyloid assembly protein CsgF. *Proceedings of the National Academy of Sciences of the United States of America* 106, 900 (2009).
23. Loferer, H., Hammar, M. & Normark, S. Availability of the fibre subunit CsgA and the nucleator protein CsgB during assembly of fibronectin-binding curliis limited by the intracellular concentration of the novel lipoprotein CsgG. *Molecular Microbiology* 26, 11-23 (1997).
24. Taylor, J. D. et al. Atomic Resolution Insights into Curli Fiber Biogenesis. *Structure* 19, 1307-1316 (2011).
25. Hammar, M., Arnvist, A., Bian, Z., Olsen, A. & Normark, S. Expression of two csg operons is required for production of fibronectin- and congo red-binding curli polymers in *Escherichia coli* K-12. *Mol Microbiol* 18, 661-70 (1995).
26. Duguid, J. P., Anderson, E. S. & Campbell, L Fimbriae and adhesive properties in Salmonellae. *The Journal of pathology and bacteriology* 92, 107-138 (1966).
27. Collinson, S. K., Parker, J., Hodges, R. S. & Kay, W. W. Structural predictions of AgfA, the insoluble fimbrial subunit of< i> Salmonella</i> thin aggregative fimbriae. *Journal of Molecular Biology* 290, 741-756 (1999).
28. Dueholm, M. S. et al. Functional amyloid in *Pseudomonas. Molecular Microbiology*, no-no (2010).
29. White, A. P. et al. High efficiency gene replacement in *Salmonella enteritidis*: chimeric fimbrins containing a T-cell epitope from *Leishmania major. Vaccine* 17, 2150-2161 (1999).
30. Flemming, H-C & Wingender, J. The biofilm matrix. *Nature Reviews Microbiology* (2010).
31. Vu, B., Chen, M., Crawford, R. J. & Ivanova, E. P. Bacterial Extracellular Polysaccharides Involved in Biofilm Formation. *Molecules* 14, 2535-2554 (2009).

32. Freitas, F., Alves, V. D. & Reis, M. A. M. Advances in bacterial exopolysaccharides: from production to biotechnological applications. *Trends in Biotechnology* 29, 388-398 (2011).
33. Giltner, C. L. et al. The *Pseudomonas aeruginosa* type IV pilin receptor binding domain functions as an adhesin for both biotic and abiotic surfaces. *Molecular Microbiology* 59, 1083-1096 (2006).
34. Wang, X., Thou, Y., Ren, J. J., Hammer, N. D. & Chapman, M. R. Gatekeeper residues in the major curlin subunit modulate bacterial amyloid fiber biogenesis. *Proceedings of the National Academy of Sciences* 107, 163-168 (2010).
35. Arakaki, A. A Novel Protein Tightly Bound to Bacterial Magnetic Particles in Magnetospirillum magneticum Strain AMB-1. *Journal of Biological Chemistry* 278, 8745-8750 (2002).
36. Zakeri, B. et al. Peptide tag forming a rapid covalent bond to a protein, through engineering a bacterial adhesin. *Proceedings of the National Academy of Sciences* 109, E690-7 (2012).
37. Thou, W., Schwartz, D. T. & Baneyx, F. o. Single-Pot Biofabrication of Zinc Sulfide Immuno-Quantum Dots. *Journal of the American Chemical Society* 132, 4731-4738 (2010).
38. Slocik, J. M., Stone, M. O. & Naik, R. R. Synthesis of Gold Nanoparticles Using Multifunctional Peptides. *Small* 1, 1048-1052 (2005).
39. Kim, S. N. et al. Preferential Binding of Peptides to Graphene Edges and Planes. *Journal of the American Chemical Society* 133, 14480-14483 (2011).
40. Shewmaker, F. et al. The functional curli amyloid is not based on in-register parallel beta-sheet structure. *J Biol Chem* 284, 25065-76 (2009).
41. Westall, F. et al. Early Archean fossil bacteria and biofilms in hydrothermally-influenced sediments from the Barberton greenstone belt, South Africa. *Precambrian Research* 106, 93-116 (2001).
42. Zhang, J., Zhang, E., Scott, K. & Burgess, J. G. Enhanced electricity production by use of reconstituted artificial consortia of estuarine bacteria grown as biofilms. *Environ Sci Technol* 46, 2984-92 (2012).
43. Cegelski, L. et al. Small-molecule inhibitors target *Escherichia coli* amyloid biogenesis and biofilm formation. *Nat Chem Biol* 5, 913-9 (2009).
44. Lee, T. S. et al. BglBrick vectors and datasheets: A synthetic biology platform for gene expression. *J Biol Eng* 5, 12 (2011).
45. Gibson, D. G. et al. Enzymatic assembly of DNA molecules up to several hundred kilobases. *Nat Methods* 6, 343-5 (2009).

TABLE 1

| Peptide | Sequence | Length (aa) | Type | Function | Reference |
|---|---|---|---|---|---|
| HIS | HHHHHH (SEQ ID NO: 15) | 6 | Affinity Tag | Affinity Tag | Bio/Technology 1688, 6(11): 1321. |
| GBP | EPLQLKM (SEQ ID NO: 6) | 7 | Substrate Binding | Graphene edge binding | JACS 2011, 133: 14480. |
| FLAG | DYKDDDDK (SEQ ID NO: 16) | 8 | Affinity Tag | Affinity tag | Nature Biotech. 1988, 6: 1204. |
| CBP | HSSYVVYAFN NKT (SEQ ID NO: 7) | 12 | Substrate Binding | Carbon nanotube binding | Nano. Lett. 2006, 6: 40. |
| A3 | AYSSGAPPMP PF (SEQ ID NO: 8) | 12 | Substrate Binding | Gold surface binding | Small 2005 1(11): 1048. |
| Z8 | LRRSSEAHNSI V (SEQ ID NO: 17) | 12 | NP templating | ZnS quantum dot templating | J. Mater. Chem. 2003, 13: 2414. |
| E14 | PWIPTPRPTFT G (SEQ ID NO: 18) | 12 | NP templating | CdS quantum dot templating | J. Mater. Chem. 2003, 13: 2414. |
| QBP1 | PPPWLPYMPP WS (SEQ ID NO: 19) | 12 | Substrate Binding | Quartz/Glass binding | Bioinformatics 2007, 23: 2816. |
| CLP12 | NPYHPTIPAQS VH (SEQ ID NO: 20) | 12 | Mineral templating | Hydroxyapatite templating | Langmuir 2011, 27: 7620. |
| SpyTag | AHIVMVDAY KPTK (SEQ ID NO: 9) | 13 | Protein Display | Covalent capture/display of proteins | PNAS 2012, 109(12): E690. |
| CT43 | CGPAGDSSGV DSRSVGPC (SEQ ID NO: 11) | 18 | NP templating | ZnS quantum dot templating | JACS 2010, 132: 4731. |

TABLE 1-continued

| Peptide | Sequence | Length (aa) | Type | Function | Reference |
|---|---|---|---|---|---|
| MBD | KCTSDQDEQF IPKGCSKGSG GSG (SEQ ID NO: 21) | 23 | Substrate Binding | Binding to stainless steel surfaces | Mol. Microbiol. 2006, 59(4): 1083. |
| AFP8 | DTASDAAAA AALTAANAK AAAELTAAN AAAAAATAR (SEQ ID NO: 22) | 37 | Substrate Binding | Ice crystal binding | JBC 1998, 273(19): 11714. |
| Mms6 | GGTIVVTGKGL GLGLGLGLGA WGPIILGVVG AGAVYAYMK SRDIESAQSDE EVELRDALA (SEQ ID NO: 12) | 59 | NP templating | Magnetite NP templating | JBC 2003, 278(10): 8745. |

Example 3: Programmable Biofilm-Based Materials from Engineered Curli Nanofibers Because of their role in bacterial pathogenicity and persistence, the vast majority of research on biofilms has focused on preventing their formation and promoting their dispersal. However, this has resulted in an overlooked opportunity to develop biofilms as functional materials. Demonstrated herein is a new technology platform, Biofilm-Integrated Nanofiber Display (BIND), in which the display of functional peptides is genetically engineered on the curli system of E. coli, the major proteinaceous component of the biofilm matrix consisting of thin amyloidogenic nanofibers. It is contemplated herein that bacteria in such a system can serve as a living foundry for the production, assembly, and post-processing of customized advanced biomaterials and programmable surface coatings. Identified herein is a fusion site in the structural curli gene csgA that allows for the display of peptides while retaining the ability of secreted CsgA chimeras to self-assemble into curli fiber networks. A library of functional peptides with a range of sizes and secondary structures were recombinantly engineered into the curli biofilms, demonstrating the modularity and flexibility of the curli display system. Furthermore, the kinetics and stability of the BIND nanofibers are established and it is demonstrated that the peptides are fully displayed, as designed. Finally, the retention of peptide functionality in BIND biofilms was demonstrated in three broad applications: engineered adhesion, peptide catalysis, and protein immobilization.

When Louis Pasteur and Robert Koch developed the germ theory of disease in the 19th century, microbes assumed a singular role as a dominant threat to human health1, 2. However, with advances in microbial research and the advent of recombinant DNA technology by Lobban, Cohen, and Boyer, we entered an era where microorganisms could be genetically manipulated to generate biomolecules for a myriad of technologies, essentially domesticating microbial biochemistry3, 4. As described herein, bacterial biofilms are embarking on a similar trajectory. In nature, most bacteria exist as biofilm communities, residing in a self-generated protective nanoscale scaffold of proteins, sugars, lipids, and extracellular DNA that defends against environmental rigors5. Biofilm formation is essential for bacterial adhesion and colonization of both natural and man-made surfaces. Characterization of biofilms in the mid-20th century revealed their key role in microbial persistence and pathogenicity, which has recently led to an abundance of research on biofilm prevention and dispersal.6, 7 However, these highly evolved extracellular matrices hold untapped potential as a beneficial nanobiotechnology engineering platform. There is a significant body of work that investigates the use of biofilms for beneficial purposes such as wastewater treatment8-10 and biotransformations11-13, but these efforts focus on the use of naturally occurring organisms that happen to have evolved various desired qualities. Efforts to rationally engineer the structure of biofilms at the molecular level have, to our knowledge, been completely absent. To date, there exists no robust and broad technology for the facile engineering of biofilm components.

The approach described herein to controlling the molecular composition of biofilm-based materials relies on the curli system —a proteinaceous component of some E. coli biofilms. The curli system is composed of a small 13-kDa-protein monomer, CsgA, that is secreted by the cell and self-assemble into highly robust amyloid nanofibers that are anchored to the cell surface by a homologous outer-membrane protein, CsgB14-16. The resulting curli nanofibers have a diameter of ~7 nm and form a tangled curly mass that encapsulates the cells.17 Curli biosynthesis is promoted by an operon that contains seven genes (csgA-G).18 Of these, CsgA is the main structural component,19 while the other proteins are involved in the nucleation of amyloid fibers (CsgB),20 or the processing (CsgE, F),21, 22 secretion (CsgC, G)23, 24, and control of transcription (CsgD)17 of CsgA. The curli system was utilized because it exhibits several features that make it amenable to the type of materials engineering platform that are contemplated herein. First, the amyloid fibers formed by CsgA are extremely robust, being able to withstand boiling in SDS25, increasing their potential utility in harsh environments. Second, since the extracellular fiber network is composed primarily of a single protein, its structural features can be easily controlled by manipulating a single gene. Finally, although analogous extracellular amyloid systems exist in other organisms, notably Salmonella26, 27 and Pseudomonas,28 the curli system is by far the best studied, and the fact that it occurs natively in E. coli and consists of a single structural protein makes it highly genetically tractable. Although some of these other fimbriae systems have been investigated as cell-surface display technologies for potential vaccine delivery agents,29 there has been no research into their use in other biofilm-based biotechnological applications.

Described herein is a strategy called "biofilm-integrated nanofiber display" (BIND), which permits the programming of an E. coli biofilm's functional properties by genetically appending functional peptide domains to the CsgA protein. After the new CsgA-peptide is secreted and assembled, the amyloid nanofiber network displays the peptide in very high density on its surface. The biofilm's function is then augmented according to the sequence of the displayed peptides. It is demonstrated herein that functional peptide domains of various lengths and secondary structures can be appended to CsgA without precluding the formation of curli fibers. Furthermore, the effect of peptide domain fusion on the self-assembly kinetics of the CsgA mutants is quantified. Lastly, it is demonstrated herein that the peptide domains maintain their function in the context of the biofilm after secretion and assembly.

Results

Design of BIND for Programmable Functionalized Biofilms. For the design of our BIND platform, a number of considerations were taken into account. The system has to be genetically tractable and modular, allowing for the facile integration of any functional peptide domain into the biofilm. This precludes the use of the polysaccharide biopolymers that form the bulk of biofilm mass,30, 31 as their synthesis relies on multi-enzymatic pathways that are difficult to engineer.32 Proteinaceous components of biofilms known as fimbriae, which form cell-anchored nanoscale protein fibers, were selected as the scaffold of choice. Of the fimbriae systems in bacteria, the curli system was chosen as these amyloid nanofibers are primarily composed of a single self-assembling protein, CsgA. This maximizes the representation of the functional domain in the assembled network and greatly simplifies the complexity of the system. Furthermore, this well-studied system is native to E. coli, providing a wealth of genetic tools and expression technologies to work with. Therefore, we first decided to test fusions of the functional domain to the N- or C-terminus of CsgA.

Figure 7A:
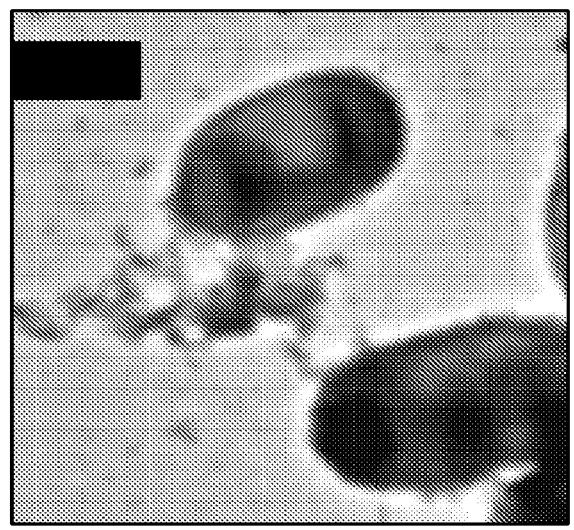
FIGS. 7A-7B depict TEM images of cells expressing C3 mutation (FIG. 7A) and wt-CsgA (FIG. 7B) for comparison.
Figure 7B:
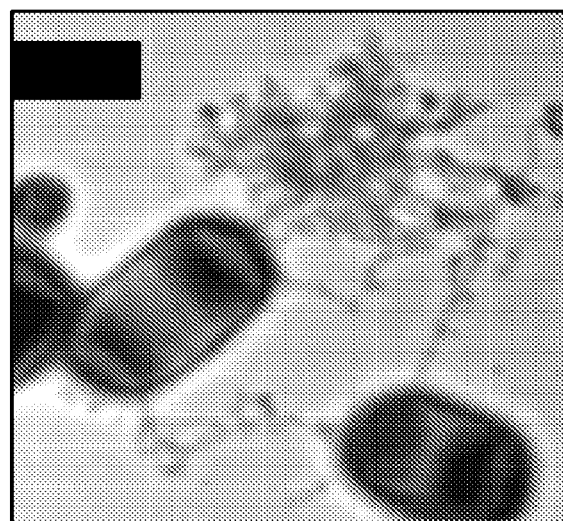

C-terminal Peptide Fusions to CsgA Are Able to Form Curli Nanofibers. Described herein is the creation of genetic fusions to the CsgA protein that maintain its ability to form curli fibers. This was accomplished by creating a panel of mutants (schematically shown in FIG. 3) consisting of CsgA fused at the N- or C-terminus to a metal binding domain (MBD), a peptide domain from the Pseudomonas spp. known to bind strongly to stainless steel surfaces.33 Three variants were prepared for each terminus: MBD is linked to CsgA either directly, or with a short (GS) or long (GSGGSG (SEQ ID NO: 13)) flanking linker. The csgA variants were cloned into plasmids and transformed into a strain of E. coli (LSR10) missing the wild-type csgA gene, but containing the remaining curli processing machinery.34 Therefore, upon induction, amyloid formation could be attributed solely to the heterologously engineered CsgA fusion mutants. As a readout of curli fiber production, Congo Red (CR) staining of bacterial colonies on low-salt media, which is a standard colorimetric indicator for amyloid fibril formation, was used.14 The results of the insertion panel show that only the C3 fusion, which has the longest linker between the CsgA C-terminus and the MBD, is able to form an appreciable amount of amyloid fibers (FIG. 1B). Other fusions are not tolerated, as evidenced by the lack of CR staining (FIG. 1B). TEM images visualizing the curli fibers that result from the CsgA fusion proteins support this data, with the C3 insertion site producing visible nanofibers (FIG. 7A; wild-type curli shown for comparison in FIG. 7B). These results clearly demonstrate that it is possible to make C-terminal genetic fusions to CsgA without inhibiting its secretion from the cell and extracellular assembly into amyloid fibers.

The C3 Design Allows for Modular Incorporation of Various Peptides Into Curli Biofilms.

To test the modularity of the functional domains that can be fused to the C-terminus of CsgA, we created a library of peptide domain fusions ranging in size from 7 to 59 amino acids while maintaining the 6 amino acid flexible linker from C3 (Table 1). The library also represents different secondary structures, as most of the peptides are not designed to exhibit any defined conformation, while MBD and Mms635 contain intramolecular disulfide bonds, which should lock them into a more rigid conformation. Finally, the library members were designed to span a range of functions that might be potentially useful in future applications of the BIND system to various technologies, including capturing proteins36 and binding to inorganic nanoparticles37-39 and surfaces.33 The library members were cloned into LSR10 cells and probed for the formation of curli-based amyloid networks by CR staining Positive CR staining (FIG. 2A) and quantitative analyses (FIG. 4) for most of the library members suggests that small peptide fusions were tolerated by the curli export machinery and successfully assembled into extracellular amyloid networks. The only mutant for which there was no positive staining was the 59-amino acid Mms6 domain. This was not entirely unexpected, since CsgA is thought to be transported across the outer membrane by the CsgG complex as an unfolded conformer15. Given that the pore size of the CsgG complex is estimated to be ~2 nm, 24 this suggests that larger folded domains may not be compatible with the curli export machinery.

TEM imaging of the modified curli biofilms indicates that the CsgA-peptide fusions assemble into nano-scale fibers similar to those observed for wt-CsgA (data not shown). The fibers display a characteristic tangled curly morphology and appear to be closely associated with the cell surface. The TEM images were intentionally obtained with diluted samples so that the nanostructure of the fibers could be easily discerned. The fibers in these images that appear to be fully extended are likely an artifact of the drying process during sample preparation and do not represent the native fiber morphology. Furthermore, SEM imaging shows that the modified curli biofilms can be very dense and several cell layers thick (data not shown) while maintaining a highly interconnected network of fibers between cells.

In Vitro Self-assembly Kinetics of CsgA-Peptide Fusions. In order to determine the effect of peptide domain fusion on the self-assembly of CsgA, several variants were selected for purification and assembly studies in vitro. For purification purposes, the CsgA-peptide fusions were appended to a His-tag followed by an enterokinase cleavage sequence. The purification sequences were inserted in place of the Sec tag such that the proteins would not be exported to the periplasm and after affinity purification from cell lysates, the enterokinase cleavage yielded proteins that were identical to those secreted by the corresponding LSR10 transformants after processing of the native Sec tag40. The purified proteins were monitored for their assembly kinetics using an established thioflavin T (ThT) assay.

Functionality of Peptides Displayed with BIND. The BIND system described herein can introduce a variety of novel functions to curli-based biofilms. Therefore, in addition to confirming secretion and assembly of CsgA-peptide chimeras, it was also sought to demonstrate that the fused peptide domains maintain their cognate functions in the context of the fully formed biofilms. Accordingly, two peptides from Table 1 were selected (MBD and SpyTag) and their ability to augment biofilm performance tested. MBD was chosen because its affinity for steel should enhance the adhesion of curli-based biofilms to stainless steel surfaces. To test this hypothesis, LSR10 cells expressing the CsgA-MBD mutant were grown in culture and, after induction, spotted onto stainless steel 304L coupons and allowed to dry in air. The same procedure was followed with cells expressing wt-CsgA and no CsgA as negative controls. Each coupon included an array of three spots —one from each culture. The coupons were then subjected to vigorous washing by submerging them in aqueous buffer and vortexing (FIG. 5A). Biofilms composed of the CsgA-MBD fusion clearly withstood the washing procedure, while those expressing wt-CsgA or no CsgA were easily washed off the surface (FIGS. 5B-5D).

These data indicate that the adhesion of curli-based biofilms to non-natural surfaces can be artificially enhanced by appending peptide domains that have been pre-selected to exhibit a desired function.

As a second demonstration of the utility of the BIND system, the CsgA-SpyTag mutant was investigated as a means to immobilize full-length proteins to the curli matrix. The SpyTag-SpyCatcher system is a recently developed strategy for protein capture that uses a CnaB2 protein that has been split into a 13 amino acid peptide (SpyTag) and a 15-kDa protein (SpyCatcher).36 When brought together, the two fragments catalyze the formation of an intermolecular isopeptide bond. This strategy was used to circumvent the apparent size limitations of the curli export machinery by enabling covalent bond formation between the curli network and larger proteins using completely genetically encodable components. Accordingly, biofilms displaying containing the CsgA-SpyTag chimera were formed on a surface-modified glass substrate using PHL628 cells, an *E. coli* strain that has been engineered to over-produce CsgA. A SpyCatcher-Venus fusion protein was used to probe for the presence and functionality of the SpyTag domain. Venus is a green fluorescent protein variant with enhanced optical properties. The glass-immobilized biofilms were treated with a nucleic acid stain (SYTO 61, Invitrogen) to test for the presence of cells. Subsequently, they were treated with a solution containing either SpyCather-Venus, or SpyCatcherEQ-Venus, a mutant in which the covalent bond formation has been abolished. Following extensive washing steps, the biofilms were imaged using fluorescence microscopy. Only the proper combination of biofilms expressing the CsgA-SpyTag and treatment with SpyCatcher-Venus resulted in significant co-localization of the two fluorescent signals (FIG. 6F). Biofilms expressing wt-CsgA were unable to capture the fluorescent protein. Similarly, biofilms expressing CsgA-SpyTag did not exhibit green fluorescence when treated with the non-functional SpyCatcherEQ-Venus mutant. Together these results indicate that SpyTag peptide can be fused to CsgA and maintain its functionality after formation of the curli network.

Discussion

The straightforward self-assembling system presented herein allows for the precise molecular control of bacterial extracellular matrix composition by genetic engineering and establishes a platform for the creation of functional bionanomaterials from living systems and perhaps even living functional materials. The advantages of such a synthetic biology platform are numerous: curli fibers can be engineered to display a variety of peptides with useful features, such as binding to or biotemplating the synthesis of inorganic materials, enhancing biofilm adhesion to particular surfaces, or providing a scaffold-like surface coating for the immobilization of other biomolecules. The biofilm itself is a "green" (i.e., environmentally friendly) material in that it is made biosynthetically and requires no petroleum-derived raw building blocks. Additionally, the biofilm has the capacity to be a self-generating and self-repairing renewable material.

Surface modification and functionalization is ubiquitous in nearly all aspects of our society. However, the use of biologically-derived surface coatings are lacking. Life has evolved a highly efficient coating strategy that was an early evolutionary adaptation enabling the bacterial colonization of surfaces41. Current applications of biofilms for applied technology utilize naturally occurring biofilms or co-cultures of biofilm-forming bacteria42 to generate the desired functionality for thin-film biocatalysis or bioremediation. These applications remain limited and the adoption of biofilm-based technology in other industries is greatly hindered by an inability to program biofilm functionality and control the temporal dynamics of biofilm formation.

The curli system of *E. coli* plays a central role in host-cell adhesion of enteropathogenic strains and is critical for the formation of biofilms25. Curli has been extensively studied as a model system for functional bacterial amyloids18 as well as for the development of biofilm-inhibiting compounds43. It is demonstrated herein that the curli system can be a programmable biofilm platform as it is predominantly composed of a single genetically programmable unit, the self-assembling CsgA protein.

Materials and Methods

Cell Strains and Plasmids. All cloning and protein expression was performed in Mach1™ (Invitrogen) and Rosetta™ cells (EMD), respectively. The csgA gene was isolated from *E. coli* K-12 genomic DNA and cloned into pBbEl a, a ColE1 plasmid under control of the Trc promoter44. Expression vectors were constructed using pET30a plasmids (EMD), with the native N22 region of the CsgA protein cloned immediately after the enterokinase cleavage site. Peptide insert regions were either fully synthesized (Integrated Dna Technologies) or PCR-generated by overlap extension. All cloning was performed by using isothermal Gibson Assembly as described45 and verified by DNA sequencing.

Curli Biofilm Formation. To produce curli, LSR10 cells or PHL628 cells were transformed with pBbE1a plasmids encoding for CsgA or CsgA-peptide fusions. As a negative control, cells were transformed with empty pBbE1 a plasmid. The cells were then streaked or spotted onto YESCA-CR plates, containing 10 g/L of casamino acids, 1 g/L of yeast extract, and 20 g/L of agar. All media components were from Fisher. The plates were supplemented with 100 mg/mL of ampicillin, 0.5 mM of IPTG, 25 mg/mL of Congo Red and 5 mg/mL of Brilliant Blue G250. The plates were then incubated for 48 hours at 25° C. and then imaged to determine the extent of Congo Red binding. For the spotted plates, the transformants were grown in YESCA liquid media supplemented with 100 mg/mL of ampicillin and 0.2 mM of IPTG for 48 hours at 25° C. before spotting 20 mL onto YESCA-CR plates. This same YESCA liquid induction procedure was used to prepare samples for CsgA purification, and electron microscopy.

Quantitative Congo Red Binding Assays. Determination of Congo Red binding was adapted from previously published methods. Briefly, transformant cultures grown on YESCA plates for 48 hours at 25° C. were scraped and resuspended gently in PBS. The cell resuspention was adjusted to an OD600 of 3. To 1 mL of this, a Congo Red solution was added to a final concentration of 0.001% and allowed to incubate at 4° C. for 1 hour. The cells were then pelleted and the 490 nm absorbance of 200 µL of the supernatant was measured in a BioTek H1 microplate reader. The amount of Congo Red binding was determined as the subtractive amount of this measurement against a PBS+ Congo Red control. All samples were performed in triplicate.

Chimeric CsgA Purification. Rosetta™ cell transformants were grown in LB until mid-log phase and induced with 0.2 mM IPTG for 3 hours. The cells were pelleted and then frozen at −20° C. for subsequent purification. The pellets were thawed and lysed in BugBuster Protein Extraction Reagent™ (EMD), 1 mg/mL Lysozyme, 50 µg/mL DNase, and protease inhibitors (Roche). After 30 minutes, the lysate was diluted into a solution of 8 guanidine hydrochloride, 250 mM NaCl, and 50 mM Tris at a pH of 7.5 and incubated for 16 hours to dissolve aggregates. Any insoluble mass was pelleted by centrifugation at 18,000 rpm for 30 minutes, the clarified lysate was filtered through a 0.22 micron filter, and then incubated with Ni-NTA resin (Qiagen) for 2 hours. The protein-bound resin was then washed with 8 guanidine hydrochloride, 250 mM NaCl, 0.1% TRITON™ X-100, 1 mM DTT, and 50 mM Tris (pH of 7.5) and eluted with the same buffer supplemented with 200 mM imidazole. The eluate was dialyzed into EK cleavage buffer (1M Urea, 20 mM methylamine, 50 mM Tris, pH 7.5) and then incubated with 3 ng of enterokinase (Roche) for 24 hours. The cleaved CsgA protein was then lyophilized, treated with 100 µL of HFIP to dissolve any curli fibers, and stored as a dried powder.

ThT Kinetic Assay Immediately before the ThT assay, the cleaved, HFIP-treated protein was resolubilized into 8M guanidine hydrochloride, 250 mM NaCl, 0.1% TRITON™ X-100, and 50 mM Tris at a pH of 7.5. This solution was FPLC purified on a SEPHADEX® G75 gel-filtration column to remove dimers and oligomers. The fraction containing the monomeric CsgA fusions were then desalted and the concentration determined by UV absorbance. The ThT assay was immediately performed with 30 µM of the CsgA fusion or wild-type protein with 40 µM ThT; the fluorescence was measured in a SpectramaxM2 plate reader at 438ex/495em.

TEM and SEM. Curliated wildtype or BIND cell samples were either directly taken from induced YESCA cultures or scraped from YESCA-CR plates and resuspended in Millipore H2O. For TEM analysis, 5 mL of the sample was spotted onto formvar-carbon grids (Electron Microscopy Sciences), washed twice with Millipore H2O, and stained for 15 seconds with 1% uranyl formate before analysis on a JEOL 1200 TEM. For SEM analysis, samples were applied to NUCLEOPORE filters under vacuum, washed with Millipore H2O and fixed with 2% glutaraldehyde+2% paraformaldehyde overnight at 4° C. The samples were then washed in Millipore H2O, dehydrated with an increasing ethanol step gradient, and dried using an hexamethyldisilazane step gradient before gold sputtering and analysis on a Zeiss Supra 55VP™ FE-SEM.

Immunogold TEM. For anti-FLAG immunogold labeling of the BIND cells displaying the FLAG tag, the cells were first adhered to the TEM grid as described above. Then, the grids were washed 3× in blocking buffer (PBS+1% BSA), floated on a drop containing a 1:1000 dilution of primary anti-FLAG murine antibody in PBS for XX minutes, washed in blocking buffer again, and then floated on a drop of 1:1000 diluted anti-mouse 15 nm gold-conjugated antibody. After a final 3× wash in PBS and then Millipore H2O, the grids were stained with 1% uranyl formate for 15 seconds and imaged on a JEOL 1200™ TEM.

SpyCatcher-Venus construction and expression. Rosetta™ cells containing pDEST14-SpyCatcher-Venus were grown up in 5 mL overnight cultures in LB at 37 C with 100 mg/L ampicillin. 500 mL cultures supplemented with ampicillin were inoculated with the overnight culture and grown up for 6 h at 37 C until an OD of 0.6. SpyCatcher-Venus expression was induced with 0.5 mM IPTG and allowed to express overnight at 18 C. Cells were harvested and lysed and SpyCatcher-Venus was purified on a Ni-NTA column. Protein was collected, buffer exchanged into 50 mM phosphate buffer 50 mM NaCl pH 7, concentrated and stored at −80 C until further use.

Fluorescent Biofilm Imaging. Fluorescent images were taken in epifluorescence mode on a Leica TIRF DM16000B™ instrument. Glass cover slips (No: 1.5) were plasma activated for 30 s each. Slides were immersed in 0.01 w/v % PLL solution for 2 h and then were placed in 60 C incubator for 2 h. PHL628 WT and CsgA-SpyTag(ST) cells were grown up in 20 mL cultures for 6 h at 37 C in YESCA broth containing 100 mg/L ampicillin until an OD of 0.6. Coverslips were dropped into the cultures and curli expression and biofilm formation were induced with 0.5 mM IPTG and 3% DMSO. Cultures were shaken at 25 C and 150 rpm for 48 h. Slides were removed from the cultures and washed 3×20 min in wash buffer (lx PBS with 0.5% TWEEN® 20). After the washes, 0.5 mL of 1 mg/mL Venus-SpyCatcher or Venus-SpyCatcher(EQ) solution (1×PBS, 1% BSA, 0.5% TWEEN®) was added to slides. The biofilms were incubated for 1 h and then washed 2×20 min with wash buffer. The biofilms were then stained with Syto 61 (10 uM) for 20 min and washed with wash buffer 2×15 min shaking at 150 rpm. Slides were then imaged in epifluorescence mode with 60× and 100× oil lenses.

REFERENCES

1. Pasteur, L. Germ Theory And Its Applications To Medicine And Surgery. Comptes rendus de l'Academie des Sciences, lxxxvi., 1037-43 (1878).
2. Koch, R. Untersuchungen Über die Aetiologie der Wundinfectionskrankheiten (F. C. W. Vogel, Leipzig, 1878).
3. Morrow, J. F. et al. Replication and transcription of eukaryotic DNA in *Escherichia coli*. Proc Natl Acad Sci USA 71, 1743-7 (1974).
4. Lobban, P. (Stanford University, 1972).
5. Hemming, H. C. & Wingender, J. The biofilm matrix. Nat Rev Microbiol 8, 623-33 (2010).
6. Romling, U. & Balsalobre, C. Biofilm infections, their resilience to therapy and innovative treatment strategies. Journal of internal medicine (2012).
7. Wood, T. K., Hong, S. H. & Ma, Q. Engineering biofilm formation and dispersal. Trends in Biotechnology 29, 87-94 (2011).
8. Singh, R., Paul, D. & Jain, R. K. Biofilms: implications in bioremediation. Trends Microbiol 14, 389-97 (2006).
9. Perelo, L. W. Review: In situ and bioremediation of organic pollutants in aquatic sediments. J Hazard Mater 177, 81-9 (2010).

10. Verhagen, P., De Gelder, L. & Boon, N. Biofilm based bioremediation strategies for the treatment of pesticide waste streams. Commun Agric Appl Biol Sci 76, 239-43 (2011).
11. Gross, R., Hauer, B., Otto, K. & Schmid, A. Microbial biofilms: new catalysts for maximizing productivity of long-term biotransformations. Biotechnol Bioeng 98, 1123-34 (2007).
12. Tsoligkas, A. N. et al. Engineering biofilms for biocatalysis. Chembiochem 12, 1391-5 (2011).
13. Halan, B., Buehler, K. & Schmid, A. Biofilms as living catalysts in continuous chemical syntheses. Trends Biotechnol 30, 453-65 (2012).
14. Chapman, M. R. et al. Role of *Escherichia coli* curli operons in directing amyloid fiber formation. Science 295, 851-5 (2002).
15. Wang, X., Smith, D. R., Jones, J. W. & Chapman, M. R. In vitro polymerization of a functional *Escherichia coli* amyloid protein. J Biol Chem 282, 3713-9 (2007).
16. Wang, X. & Chapman, M. R. Sequence determinants of bacterial amyloid formation. J Mol Biol 380, 570-80 (2008).
17. Barnhart, M. M. & Chapman, M. R. Curli Biogenesis and Function. Annual Review of Microbiology 60, 131-147 (2006).
18. Chapman, M. R. Role of *Escherichia coli* Curli Operons in Directing Amyloid Fiber Formation. Science (New York, N.Y.) 295, 851-855 (2002).
19. Dueholm, M. S. et al. Fibrillation of the major curli subunit CsgA under a wide range of conditions implies robust design of aggregation. Biochemistry (2011).
20. Hammer, N. D., Schmidt, J. C. & Chapman, M. R. The curli nucleator protein, CsgB, contains an amyloidogenic domain that directs CsgA polymerization. Proceedings of the National Academy of Sciences of the United States of America 104, 12494 (2007).
21. Nenninger, A. A. et al. CsgE is a curli secretion specificity factor that prevents amyloid fibre aggregation. Molecular Microbiology 81, 486-499 (2011).
22. Nenninger, A. A., Robinson, L. S. & Hultgren, S. J. Localized and efficient curli nucleation requires the chaperone-like amyloid assembly protein CsgF. Proceedings of the National Academy of Sciences of the United States of America 106, 900 (2009).
23. Loferer, H., Hammar, M. & Normark, S. Availability of the fibre subunit CsgA and the nucleator protein CsgB during assembly of fibronectin-binding curliis limited by the intracellular concentration of the novel lipoprotein CsgG. Molecular Microbiology 26, 11-23 (1997).
24. Taylor, J. D. et al. Atomic Resolution Insights into Curli Fiber Biogenesis. Structure 19, 1307-1316 (2011).
25. Hammar, M., Arnqvist, A., Bian, Z., Olsen, A. & Normark, S. Expression of two csg operons is required for production of fibronectin- and congo red-binding curli polymers in *Escherichia coli* K-12. Mol Microbiol 18, 661-70 (1995).
26. Duguid, J. P., Anderson, E. S. & Campbell, I. Fimbriae and adhesive properties in Salmonellae. The Journal of pathology and bacteriology 92, 107-138 (1966).
27. Collinson, S. K., Parker, J., Hodges, R. S. & Kay, W. W. Structural predictions of AgfA, the insoluble fimbrial subunit of< i> Salmonella</i> thin aggregative fimbriae. Journal of Molecular Biology 290, 741-756 (1999).
28. Dueholm, M. S. et al. Functional amyloid in *Pseudomonas*. Molecular Microbiology, no-no (2010).
29. White, A. P. et al. High efficiency gene replacement in *Salmonella enteritidis*: chimeric fimbrins containing a T-cell epitope from *Leishmania major*. Vaccine 17, 2150-2161 (1999).
30. Hemming, H.-C. & Wingender, J. The biofilm matrix. Nature Reviews Microbiology (2010).
31. Vu, B., Chen, M., Crawford, R. J. & Ivanova, E. P. Bacterial Extracellular Polysaccharides Involved in Biofilm Formation. Molecules 14, 2535-2554 (2009).
32. Freitas, F., Alves, V. D. & Reis, M. A. M. Advances in bacterial exopolysaccharides: from production to biotechnological applications. Trends in Biotechnology 29, 388-398 (2011).
33. Giltner, C. L. et al. The *Pseudomonas aeruginosa* type IV pilin receptor binding domain functions as an adhesin for both biotic and abiotic surfaces. Molecular Microbiology 59, 1083-1096 (2006).
34. Wang, X., Zhou, Y., Ren, J. J., Hammer, N. D. & Chapman, M. R. Gatekeeper residues in the major curlin subunit modulate bacterial amyloid fiber biogenesis. Proceedings of the National Academy of Sciences 107, 163-168 (2010).
35. Arakaki, A. A Novel Protein Tightly Bound to Bacterial Magnetic Particles in Magnetospirillum magneticum Strain AMB-1. Journal of Biological Chemistry 278, 8745-8750 (2002).
36. Zakeri, B. et al. Peptide tag forming a rapid covalent bond to a protein, through engineering a bacterial adhesin. Proceedings of the National Academy of Sciences 109, E690-7 (2012).
37. Zhou, W., Schwartz, D. T. & Baneyx, F. o. Single-Pot Biofabrication of Zinc Sulfide Immuno-Quantum Dots. Journal of the American Chemical Society 132, 4731-4738 (2010).
38. Slocik, J. M., Stone, M. O. & Naik, R. R. Synthesis of Gold Nanoparticles Using Multifunctional Peptides. Small 1, 1048-1052 (2005).
39. Kim, S. N. et al. Preferential Binding of Peptides to Graphene Edges and Planes. Journal of the American Chemical Society 133, 14480-14483 (2011).
40. Shewmaker, F. et al. The functional curli amyloid is not based on in-register parallel beta-sheet structure. J Biol Chem 284, 25065-76 (2009).
41. Westall, F. et al. Early Archean fossil bacteria and biofilms in hydrothermally-influenced sediments from the Barberton greenstone belt, South Africa. Precambrian Research 106, 93-116 (2001).
42. Zhang, J., Zhang, E., Scott, K. & Burgess, J. G. Enhanced electricity production by use of reconstituted artificial consortia of estuarine bacteria grown as biofilms. Environ Sci Technol 46, 2984-92 (2012).
43. Cegelski, L. et al. Small-molecule inhibitors target *Escherichia coli* amyloid biogenesis and biofilm formation. Nat Chem Biol 5, 913-9 (2009).
44. Lee, T. S. et al. BglBrick vectors and datasheets: A synthetic biology platform for gene expression. J Biol Eng 5, 12 (2011).
45. Gibson, D. G. et al. Enzymatic assembly of DNA molecules up to several hundred kilobases. Nat Methods 6, 343-5 (2009).

Example 4: Orthogonal Enzyme Immobilization onto Curli Fibers of *E. coli* Biofilm Using biofilms for catalysis is desirable due to the their ability to withstand harsh conditions, their natural attachment to surfaces and their scalability. Whole cell catalysis using biofilms has limitations, however, due to the need for mass transport of substrates across the cell membrane. Enzyme display on the surface of bacteria has had limited success because of a need to co-express the enzyme with a trans-membrane or surface-displayed protein and the limited surface real estate of bacteria. Using Biofilm Integrated Nanofiber Display, BIND, a platform as described herein was developed for covalently and site-specifically attaching orthogonal enzymes to the extracellular matrix of E. coli biofilms. α-Amylase fused to an attachment domain, Spy-Catcher, was immobilized onto E. coli biofilms displaying curli fibers with a capture domain, SpyTag. It is demonstrated herein that biofilms protected the enzyme from harsh pH conditions compared to free enzyme. Furthermore, the biofilms protected the immobilized α-Amylase from denaturation in immiscible organic solvents. Described herein is a new method of using the extracellular polymeric matrix of E. coli for creating versatile and controllable biocatalytic surfaces.

Biocatalysis provides an environmentally friendly alternative[1] to chemical synthesis with its ability to perform complex chemical transformations in a scalable manner[2]. The main types of biocatalysts are whole-cell engineered microbes[3], cell lysates or purified enzymes[4] Nature has evolved enzymes to be able to perform catalysis that creates stereoselective intermediates of large, complex molecules, a feat that the synthetic chemistry field is still trying to replicate. Furthermore, in whole-cell catalysis, multi-enzyme pathways allow the transformation of simple input molecules, such as glucose, into high value products[5].

Despite the advantages of these biocatalysts, they have their respective disadvantages. Whole-cell catalysts have limitations in the types of reactions they can catalyze due to solubility of the substrate in water[6], mass transfer limitations from hindered diffusion of the substrate or product across the cell membrane[7], and the generation of byproducts or side-reactions[8]. Since the cells are not immobilized, they must be separated from the reaction mixture to isolate the product. Immobilized enzymes do not face the problems with mass transport or isolation, however the cost of purifying enzymes on a large scale is significant[8] and the activity of the enzyme can be adversely affected by the purification[9] or the immobilization process. Due to their general instability, purified enzymes are frequently immobilized onto porous surfaces when used for large-scale application, adding to the cost of the catalyst[10]. Biphasic systems have been developed to address the problem of substrate insolubility in aqueous solvents, however these systems face issues with cell toxicity, biocatalyst inactivation over prolonged exposure to organic solvents and denaturation of the catalyst from shearing upon vigorous mixing[11].

Biofilms are matrix-enclosed bacteria adhered to each other and/or to surfaces or interfaces[12]. They have many advantages over planktonic cells, like the ones traditionally used for whole-cell catalysis, because the bacteria in a biofilm secrete an extracellular polymeric matrix that provides protection against toxic chemicals[13], metals[14] and physical stress[15]. At the same time, they retain the advantages of whole cell catalysts including stabilization of the required enzyme(s) in a natural, biological environment[8], renewability and the ability to tune activity through engineering.

Current surface display technologies suffer from major limitations including difficulty with co-displaying more than one enzyme and enzyme complexes and limitations on the number of displayed enzymes due to the finite surface real estate of the bacteria.

To address the current technological limitations, described herein is a new biofilm immobilization platform, Biofilm-Integrated Nanofiber Display (BIND). BIND modifies the proteinacious component of E. coli biofilms, curli fibers, with functional peptides. In curli biosynthesis, curli monomer CsgA is secreted through the outer membrane transported CsgG, anchored onto the transmembrane protein CsgB and subsequently self-assemble into amyloid fibers roughly 7 nm in diameter[17]. A number of CsgA-functional peptide chimeras can be secreted through the curli expression pathway. When this CsgA-peptide assembles into curli fibers, the peptides become functional handles that can be used to modify the fibers, to capture metals, nanoparticles or for adhesion[18]. BIND permites the creation of catalytic surfaces through the transformation of the vast and inert polymer network of E. coli biofilm extracellular matrices into an immobilization surface. Since the substrate and product of a reaction do not have to cross any membranes, this approach solves the problem of mass transport to the biocatalyst.

The Remaut group's expression system has limitations for proteins with more innate structure—proteins containing disulfide bonds that create loops greater than the internal diameter of CsgG (~2.5 nm), for example[19]. The work described herein provides a more generalizable method for displaying proteins on curli fibers. As a result, the Spy-Catcher-SpyTag system was employed. SpyCatcher catalyzes the formation of an isopeptide bond with the 14-amino acid SpyTag[20]. As previously shown, CsgA-SpyTag assembles into near-native curli fibers with the SpyTag accessible for conjugation to SpyCatcher[18].

It is demonstrated herein that the SpyCatcher-SpyTag system can be used to immobilize a large enzyme, α-Amylase, onto the curli fibers of E. coli biofilms (FIGS. 8A-8D). This reaction is robust, with the ability to form site-specific attachment between the two components. even in a complex mixture. The activity of the enzyme on the biofilm was characterized using a filter-plate assay and it was shown that α-Amylase activity is retained under a range of pH and organic solvent incubation conditions, even when metabolic activity of the cells is lost.

Materials and Methods

Cell Strains and Plasmids. All cloning and protein expression was performed in Mach1™ (Invitrogen) and Rosetta™ cells (EMD), respectively. E. coli csgA and csgA-SpyTag genes were cloned into pBbE1a, a ColE1 plasmid under control of the Trc promoter, as previously described. CsgA was expressed in YESCA media, containing 10 g/L of casamino acids (Fisher, BP1424), 1 g/L of yeast extract (Fisher, BP1422). α-Amylase was isolated from *Bacillus licheniformis* ATCC 14580. SpyCatcher gene in pDEST14 was acquired from Addgene (35044). Amylase was inserted at the N-terminus of SpyCatcher and the construct transferred to a pET28b vector, expressed in Rosetta™ cells grown in Terrific Broth (Sigma T0918). The csgA deletion mutant was PHL628-ΔcsgA (MG1655 malA-Kan ompR234 AcsgA). Cells were lysed using a Misonix Probe Sonicator 4000™. Milipore PCF and hydrophilic PTFE filter plates (PCFMSSLBPC10, MSRLN0410) and the Milipore Multi-Screen™ vacuum manifold setup was used for filter plate assays. For Amylase activity, 4-nitrophenyl-a-D-maltopentaoside (pNPMP, Sigma, 66068-38-0) was used as a substrate and α-Amylase from *Bacillus licheniformis* (Sigma, A3403) as a standard.

Curli Expression. PHL628 cells were transformed with pBbE1a plasmids encoding for CsgA or CsgA-ST fusions prior to each experiment. The cells were then streaked onto YESCA plates, containing 10 g/L of casamino acids, 1 g/L of yeast extract, and 15 g/L of agar. The plates were supplemented with 100 g/mL of ampicillin. PHL628 cells were grown up in YESCA with Ampicillin until an OD of 0.4-0.6 at 30° C. Curli expression was induced with 0.3 mM IPTG. Cultures were shaken for 18 h24 h at 25° C. and 150 rpm.

Quantitative Congo Red (CR) Binding Assays. Determination of Congo Red (CR) binding was adapted from previously published methods. Briefly, 1 mL of induced cultures grown in YESCA were pelleted at 5000 g for 10 min and resuspended gently in PBS. 150 uL of 0.2 mM Congo Red solution in H2O was added to this and allowed to incubate at 25° C. for 10 min. The cells were then pelleted at 21 k g and the 490 nm absorbance of 200 μL of the supernatant was measured in a BIOTEK H1 microplate reader. The amount of Congo Red binding was determined as the subtractive amount of this measurement against a PBS+Congo Red control. Congo Red absorbance was translated to concentration using a standard curve.

Amylase-SpyCatcher expression Rosetta™ cells containing pET28b Amylase-Spycatcher were grown up in 5 mL overnight cultures in LB at 30° C. with 100 mg/L kanamycin. 1L of terrific broth was supplemented with kanamycin to 100 mg/L, inoculated with the overnight culture and grown up for 5 h at 30° C. until an OD of 0.4. AmylaseSC expression was induced with 0.5 mM IPTG and allowed to express overnight at 20° C. Cells were harvested and lysed in TBST and AmylaseSC was purified on a Ni-NTA column. Protein was collected, buffer exchanged into PBS and used within a day for experiments.

CsgA conjugation gels. Starter cultures of PHL628 WT and ST were grown up ON in 100 ug/mL Amp. The starter cultures were used to grow up 50 mL of bacteria and curli production was induced at OD 0.6. Cells were allowed to express curli for 24 h. Cells were spun down at 4700 g for 10 min and supernatant discarded. The pellets were redissolved in 3 mL PBS with protease inhibitors. Cells were sonicated using a probe sonicator at 15 W 5× (1 min on, 0.5 min off) cycles. Cells were again spun down at 4700 g for 10 min. 100 uL of the supernatant was spun down at 21000 g and the presence of curli was checked using a CR assay. The rest of the supernatant was incubated with previously isolated Amylase-SpyCatcher for 24 h. NaCl was added to the solution until 200 uM and solution was spun down at 21000 g for 10 min. The supernatant was removed and the pellet was washed 1×1 mL H2O and spun down again at 21000 g for 10 min. Pellet and supernatant were dried in separate tubes using a speed vac. Residue was redissolved in 1.5 mL formic acid and 0.2 mL HFIP to break up the curli fibers into monomers and the solvent evaporated off again. Residues were dissolved in Laemli buffer containing 4M Urea, heated for 5 min and ran on gel at 75V for 2 h.

In vitro Amylase-SpyCatcher Activity Assay. p-nitrophenyl-a-D-maltopentaoside (pNPMP) ws choosen as the substrate to measure amylase activity because hydrolysis 4-nitrophenol (pNP) from the pentasaccharide can be monitored at 405 nm. The absorbance intensity of pNP is dependent on its protonation state, so we ran all reactions in PBS at pH 7.4 in a 96-well plate format.

Concentration of AmylaseSC and α-Amylase (Sigma) was measured using a Bradford assay and diluted to 1.35 mM. 85 uL of 0.065-2 mM pNPMP in ddH2O was added to 50 uL of protein in PBS. Activity was measured at 405 nm ON in Biotek H1 microplate reader.

Curli Biofilm Filter Plate Assays. CsgA and CsgA-ST expressing PHL628 cells were cultured for 18 h at 25° C. at 150 rpm as described above. Curli content was measured using the quantitative Congo Red binding assay. 50-100 uL of cells (normalized to CR absorption) were transferred onto Milipore PCF of PTFE membrane filter plates blocked with 2-4% BSA for 1.5 h. The media was filtered through using a vacuum manifold. Cells were washed 2×200 uL PBS. Cells were incubated ON with 50 uL of AmylaseSC in PBS containing 1-2% BSA overnight. Liquid was removed using vacuum filtration and the biofilms were washed quickly 3×150 uL 0.3% BSA in PBS and 3 more times over 90 min shaking.

For activity assays in water-miscible solvents, 50 uL of 2× solvent solution in PBS was added with 50 uL of 2.5 mM pNPMP in H2O. Plates were placed on a desktop shaker at room temperature for 1.5-2 h. At the end of the experiment, the supernatant was vacuum filtered into a new 96-well plate and 4-nitrophenol release measured at 405 nm.

For activity assays in water-immiscible solvents, biofilms were incubated with 100-150 uL of solvent for 1 h. Solvent was removed and cells washed 2×150 uL 0.3% BSA in PBS. 50 uL of PBS and 50 uL of 2.5 mM pNPMP were added to the biofilm. Plates were placed on a desktop shaker at room temperature for 1.5 h. At the end of the experiment, the supernatant was vacuum filtered into a new 96-well plate and pNP release measured at 405 nm. Reference for relative activity is the pH 7 PBS condition.

MTS assay. Cell viability was tested using Promega CellTiter 96® Aqueous Non-Redioactive Cell Proliferation Assay. Functionalized biofilms were prepared as described above. Subsequent to exposure of biofilms to pH, miscible and immiscible organic solvents, biofilms were washed with PBS, incubated with Assay buffer for 1 h, filtered through and results read optically at 490 nm. Reference for relative metabolic activity is the pH 7 PBS condition.

SEM. Scanning electron microscopy was performed on the Zeiss Ultra Plus FESEM at the Harvard University Center for Nanoscale Systems. For SEM imaging, the enzyme-bound biofilms were fixed in 2% gluteraldehyde 4% paraformaldehyde for 30 min, then washed twice with water. The filter membranes were detached from the filter plate, dehydrated with an increasing ethanol gradient, dried on a critical point dryer, then gold-sputtered and imaged on an FESEM (5 kV operating voltage).

Confocal Microscopy. Confocal microscopy was performed on assayed cells and fixed cells from PCF plate samples. Cells were incubated with DAPI for 20 min and washed 4× over 2 h with 0.2% BSA in PBS. Membranes from PCF plates were cut out and membranes were placed between two cover slips to image with a LEICA SP5 X MP Inverted Confocal Microscope with 63× glycerol lens.

Results and Discussion

Characterization of AmylaseSC stability. Only a few methods are currently used that allow site-specific, covalent attachment of proteins to polymers or surfaces. These generally involve post-translational modification, or introduction of orthogonal chemical units through unnatural amino acids[21]. The SpyCatcher-SpyTag technology described herein is unique in that it introduces a covalent post-translational modification using completely genetically engineerable components with biologically compatible reaction conditions. SpyTag-SpyCatcher technology was selected over fusing enzymes directly to CsgA monomers because the CsgA secretion machinery (namely the transported CsgG) has been shown to have low tolerance for large, structured proteins[19].

α-Amylase was used as the proof of concept demonstration for catalytic biofilms because of its wide use, industrial applicability and the commercial availability of a water-soluble colorimetric substrate. While multiple proteins (127 domains, MBP, GFP) have been successfully attached to SpyCatcher[20], being able to create a functional enzyme-SpyCatcher fusion has not been shown before. When fusing two proteins together, there is a concern that the activity of the enzyme will diminish due to destabilization by the fused domain or blocking of the active site. When designing our Amylase-SpyCatcher construct, a 13 amino acid linker was included between the two proteins to try to mitigate such destabilization effects.

In order to test the stability of AmylaseSC, AmylaseSC activity was examined over a span of 64 days and at temperature ranges up to 80° C. As seen from the activity data gathered at 64 days, even at 37° C., α-Amylase only looses 13% of its activity, and when attached to SpyCatcher, that activity loss is still relatively small at 30%. Looking over a wider temperature range, AmylaseSC lost activity faster than α-Amylase only above 60° C. (FIG. 14B). Since the normal operating range of most cell-based applications are below 60° C., it can be concluded that at relevant temperatures, the two enzymes perform the same.

Figure 15A:
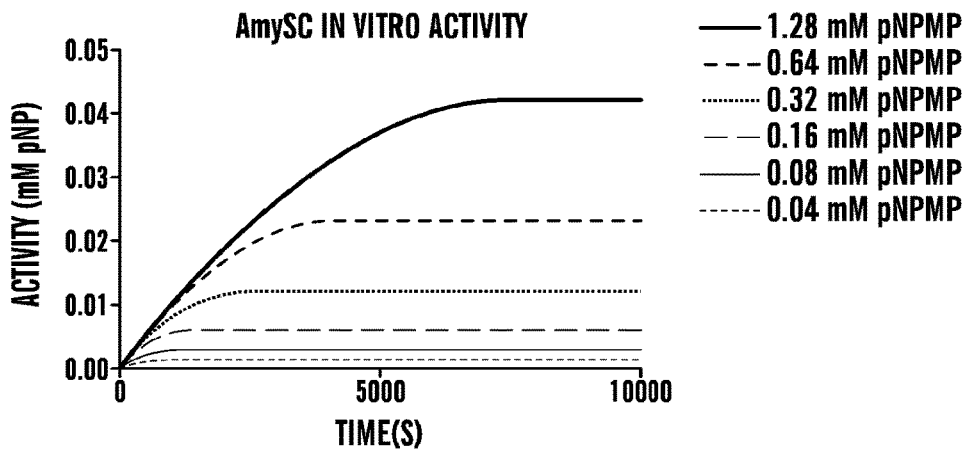
FIGS. 15A-15B demonstrate in vitro enzyme kinetics.
Figure 15B:
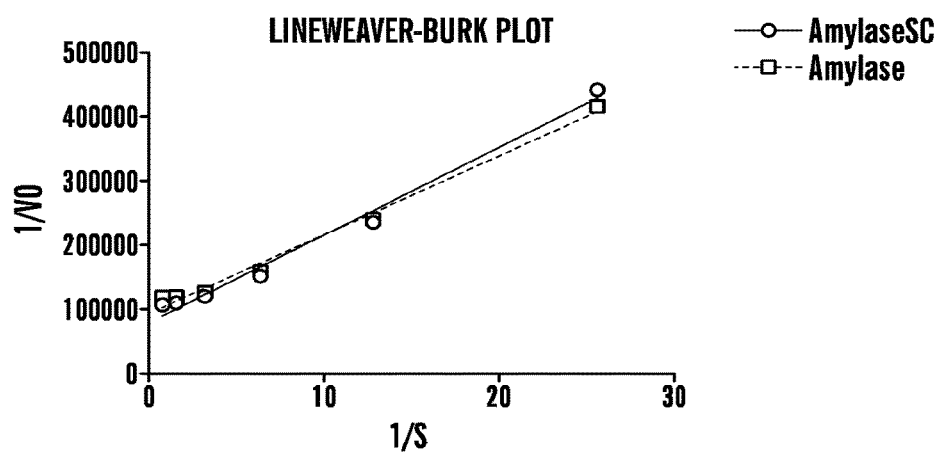

Kinetic studies of AmylaseSC were conducted in vitro in order to determine the effect of attaching α-Amylase to SpyCatcher on activity. Michaelis-Menten analysis of the results showed that the Km/kcat values were nearly identical between wild-type α-Amylase and Amylase-SC (FIG. 15A-15B), indicating that the fusion protein is able to catalyze reactions with the same efficiency as wild-type.

AmylaseSC attachment to SpyTag expressing curli fibers in vitro. In order for AmylaseSC to be able to attach to curli fibers, the SpyTag peptide needs to be accessible. In a biofilm, the peptides may be blocked due to interaction with a surface, other bacteria, other proteins or nearby SpyTag peptides and curli. Furthermore, attachment of the enzyme from a complex mixture is a desirable quality for an immobilization platform because large-scale purification of enzymes is both expensive and time-consuming[22].

In order to demonstrate that AmylaseSC can attach to CsgA-ST in a relevant complex mixture, while the curli fibers are assembled. AmylaseSC was incubated with crudely purified curli fibers and bound protein visualized using a denaturing SDS-Page gel. Due to the harsh sample preparation conditions, which involved using 8M urea and formic acid, all non-specificly bound proteins should be broken up and only covalently bound entities should run as one band. As can be seen in lanes 1 and 2 on the gel (FIG. 9), a band at around 90 kDa (the combined weight of CsgA-ST+AmylaseSC) appears in the CsgA-ST conjugation reaction precipitate, but not in the CsgA wild type sample, illustrating covalent conjugation of AmylaseSC to CsgA-ST. Unconjugated AmylaseSC is found in the soluble fractions.

AinylaseSC immobilization onto biofilms. A 96-well filter plate setup was used to test the catalytic potential of the functional biofilms. Cells were grown in culture and allowed to express curli for 18 h before being transferred into 96-well filter plates. The biofilms were then functionalized with AmylaseSC over 24 h and reacted with pNPMP. After the desired reaction time, the solutions were filtered into another 96-well plate and analyzed for the hydrolysis of pNP.

A seeding density of cells was chosen such that the biofilm would be composed of a mono or bilayer of cells on the filters. This cell density was desirable because the MG1655 AcsgA omnpR234 cells used in these experiment express both curli and cellulose in their extracellular matrix, resulting in a large quantity of extracellular material that blocks the filters when present in higher density. Confocal fluorescence images of the biofilms stained with DAPT are shown in FIGS. 10A-10B. As can be seen, the cells are surrounded by a thick matte of extracellular material. Due to the compression of the fibers from the vacuum filtration, it is difficult to distinguish between curli and cellulose on the images, however it is evident that the extracellular matrix forms a large, accessible surface area. Although this matrix looks solid on the SEM images (data not shown), it is most likely porous in reality because the DAPI staining was done on the same samples prior to SEM imaging, indicating that small molecules can get through.

Figure 11B:
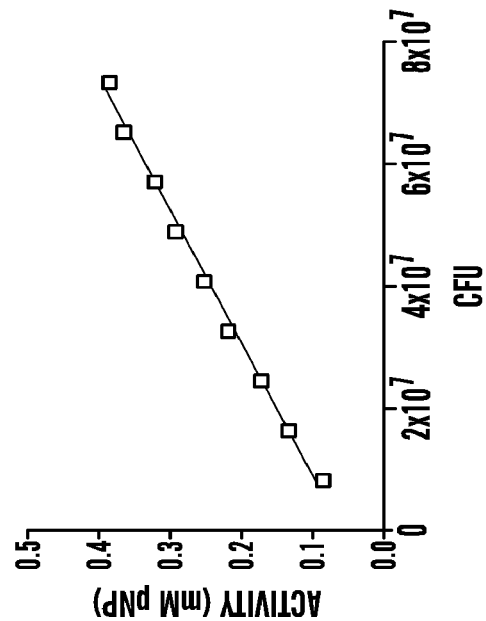
FIGS. 11A-11B demonstrate AmylaseSC immobilization onto biofilms. CsgA WT and CsgA-ST expressing biofilms are incubated with AmylaseSC for 1.5 h.
Figure 11A:
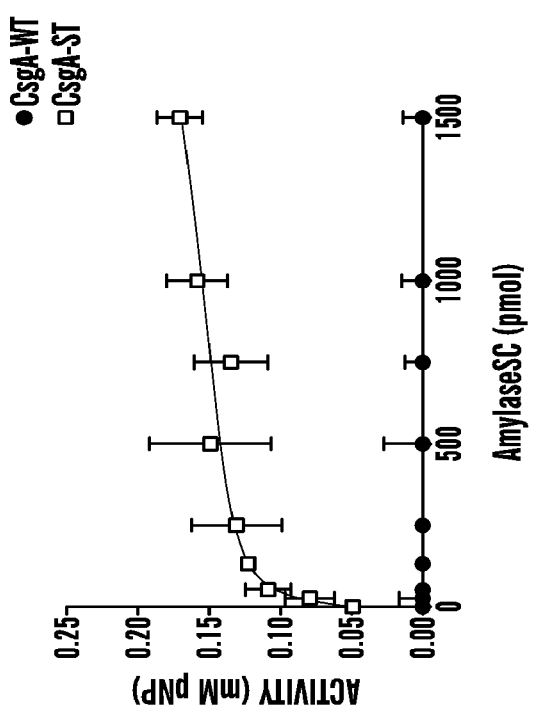

It was next sought to determine the amount of AmylaseSC that would saturate the available SpyTag sites on the biofilm. Biofilms with around $4 \times 10^7$ cells were incubated with 20-1500 pmol AmylaseSC and the activity of the enzymes on the biofilms was measured. As shown in FIG. 11A, the maximum activity of the biofilm is reached above roughly 250 pmol AmylaseSC in the incubation buffer. It is important to note that this does not accurately reflect the amount of AmylaseSC actually attached to the biofilm—even at 20 pmol enzyme, most of the enzyme is observed in the reaction supernatant (data not shown). Instead of seeing a saturated signal at the 20 pmol incubation concentration, it is hypothesized that the reason a normal binding curve is observed is due to the limited diffusion of the enzyme. That is, since the biofilm is located at the bottom of the 96-well plate, rather than being distributed throughout the well, not all of the AmylaseSC can find eligible CsgA-ST to bind to within the incubation time. For the experiments in the rest of the paper, biofilms were incubated with 750 pmol AmylaseSC to ensure saturation of the sites.

The relationship between the amount of cells per well and the activity of the biofilm provides information about the relationship between cell count and the amount of curli available for immobilizing AmylaseSC. As biofilms become thicker, there is a decrease in the extent to which molecules, such as nutrients, antibiotics, etc. can reach the bottom layers of cells[12,23]. This provides biofilm with an important evolutionary advantage over planktonic bacteria, however in the case of the present catalytic system, there is an inevitable tradeoff between biofilm thickness and the ability of AmylaseSC to reach possible conjugation sites and for the amylase substrate to reach catalytic sites. FIG. 11B shows that the activity of the biofilm linearly increases between $8 \times 10^6$ CFU to $7 \times 10^7$ CFU/well (upper limit due to filter clogging). This indicates that the curli that is added with each increase in cell count is accessible to the same extent as curli previously found in the biofilm. Using linear regression, with every $10^7$ cells added to the biofilms in this range, an extra 4.6 nmol or 3.7% of total pNPMP is hydrolyzed in the present system. This number would be higher if the filters were constantly shaken or used in a flow system.

AmylaseSC activity on biofilms under various pH. The change in ionization of charged residues on an enzyme can disrupt the enzyme's activity[24] by partially unfolding the protein and/or destabilizing the active site. It was hypothesized that an enzyme immobilized onto curli fibers would be less susceptible to activity loss due to extreme pH because of a buffering effect created by ionizable groups on the cells, curli fibers and other nearby proteins.

Figure 12A:
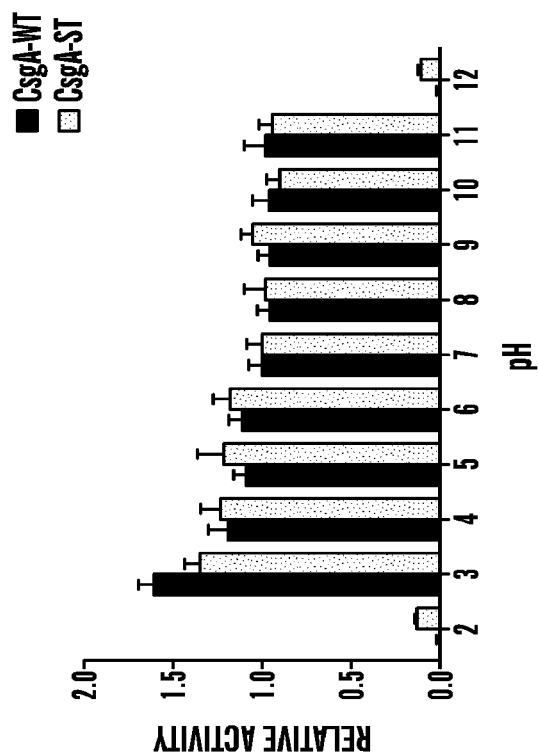
FIGS. 12A-12B demonstrate the activity of immobilized AmylaseSC with varying pH. CsgA WT and CsgA-ST expressing biofilms are incubated with PBS pH 2-12 for 2 h.

The activity of enzymes as a function of pH was measured between pH 2-12. This range was chosen because it has been previously shown that α-Amylase looses activity around pH 4 and $10^2$. As shown in FIG. 12A, AmylaseSC attached to the biofilms is close to 100% active at pH 4 and 10 while, under these conditions, α-amylase in solution looses 40% of its activity at those pHs. Neither the solution phase nor the immobilized enzyme shows activity below pH 3 or above pH 11, suggesting that the environment around immobilized AmylaseSC is partially buffered. With less stable enzymes than α-amylase, the protective effect of these biofilms may be even more pronounced.

Figure 12B:
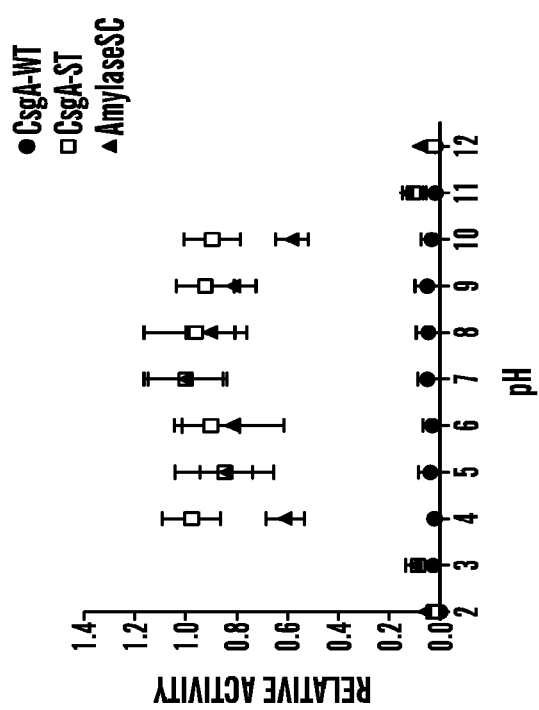

Metabolic activity of the biofilms was tested to determine if the same pH effect is observable on the internal enzyme activity as for AmylaseSC on the curli fibers. FIG. 12B shows that biofilms have metabolic activity at all pHs except pH 2 and 12. The higher activity at pH 3-6 than pH 7 (normalization pH) is most likely a result of stress on the cells from lower pH, which increases their metabolic activity as they try to mitigate sub-optimal environmental conditions. A higher pH tolerance for the whole cells is reasonable because the enzymes inside cells would be better protected from denaturation than enzymes on the extracellular matrix.

AmylaseSC activity on biofilms in organic solvents. For the successful use of catalytic biofilms, they may need to withstand conditions that are not normally beneficial for bacterial growth or enzyme stability. One major reason for this is that many small molecule enzyme substrates cannot be dissolved in water. There have been several ways developed to attempt to circumvent this problem, including immobilization of enzymes onto porous scaffolds that are then used in organic solvents[26-28] and the use of two-phase aqueous-organic systems[29,30]. In both of these cases, the organic soluble molecule briefly enters the aqueous phase, where the enzyme is able to catalyze the reaction, and then exits again into the organic phase.

Figure 13B:
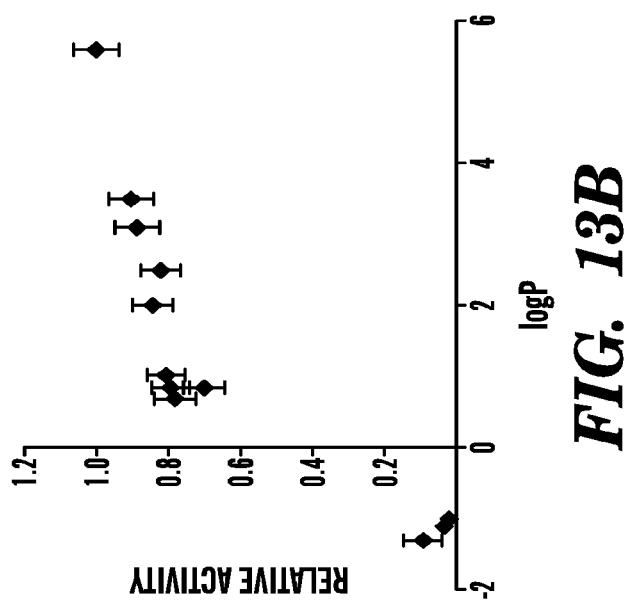
FIGS. 13A-13D demonstrate the activity of biofilms in organic solvents. Biofilms functionalized with AmylaseSC are incubated in water-miscible and immiscible organic solvents.
Figure 13A:
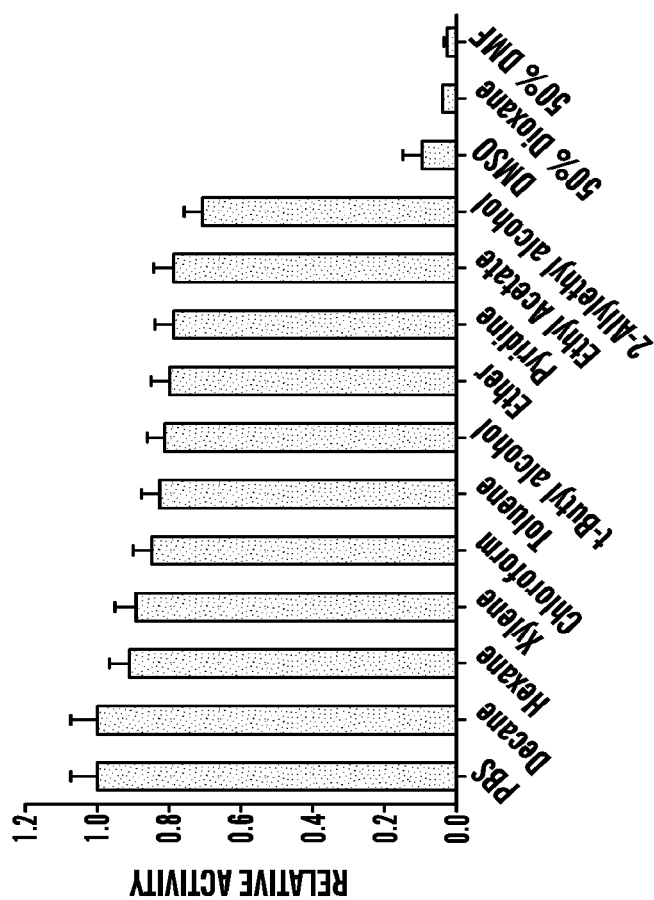

It was hypothesized that like these two-phase aqueous-organic systems, when exposed to hydrophobic solvents, the biofilm would stay hydrated and provide a protective shell around the enzymes. To test this, the biofilm was incubated with a panel of water-miscible and non-miscible organic solvents and the activity and viability of the biofilms tested. Since pNPMP is not soluble in solvents other than water, for non-miscible solvents, the biofilms were incubated in the organics and then replaced the solvent with PBS while measuring activity. As shown in FIG. 13A. the relative activity of AmylaseSC is only slightly affected by incubation with non-miscible solvents, but completely disappears in miscible solvents.

The partitioning coefficient, a measure of hydrophobicity, correlates in an s-curve manner with bioactivity[31]. In general, water-miscible solvents have a log P<0, log P of 0-2 corresponds to polar organic compounds and log P>2 to mostly nonpolar compounds. For whole cell catalysts, a log P of 2 is necessary for any activity. The results plotted against the partition coefficient show that enzyme activity is preserved when biofilms are incubated in solvents with log P0-100% activity is retained for solvents with log P>2 and, in contrast to whole cell catalysts, 70-90% activity is retained in solvents with log P 0.6-0.8. This is a unique feature of the present system and points to the potential of a broader use for the biofilm platform in organic synthesis.

Figure 13D:
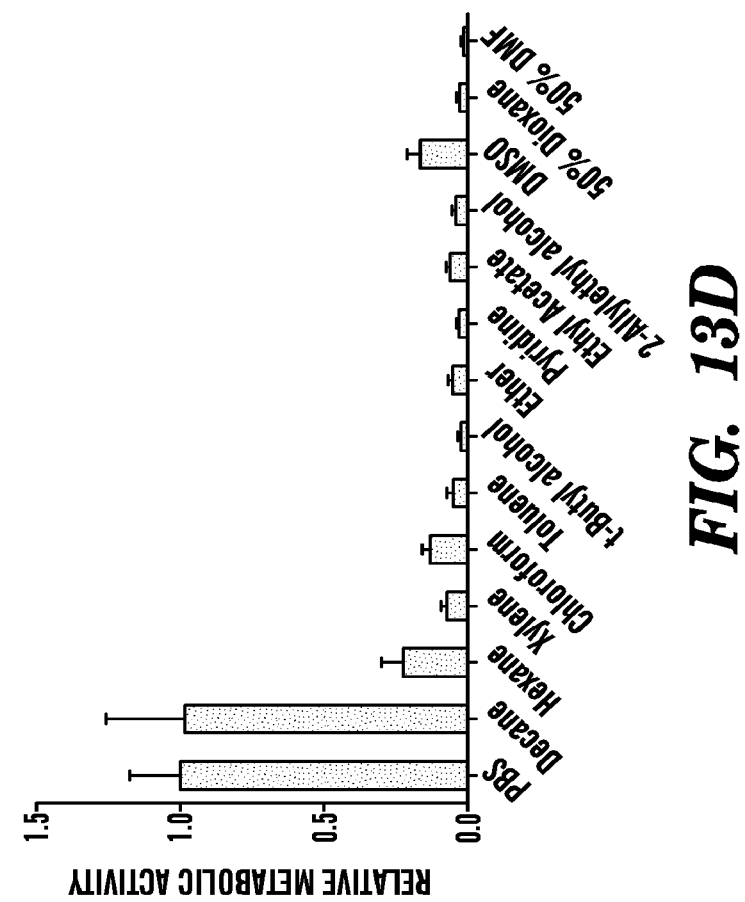
Figure 13C:
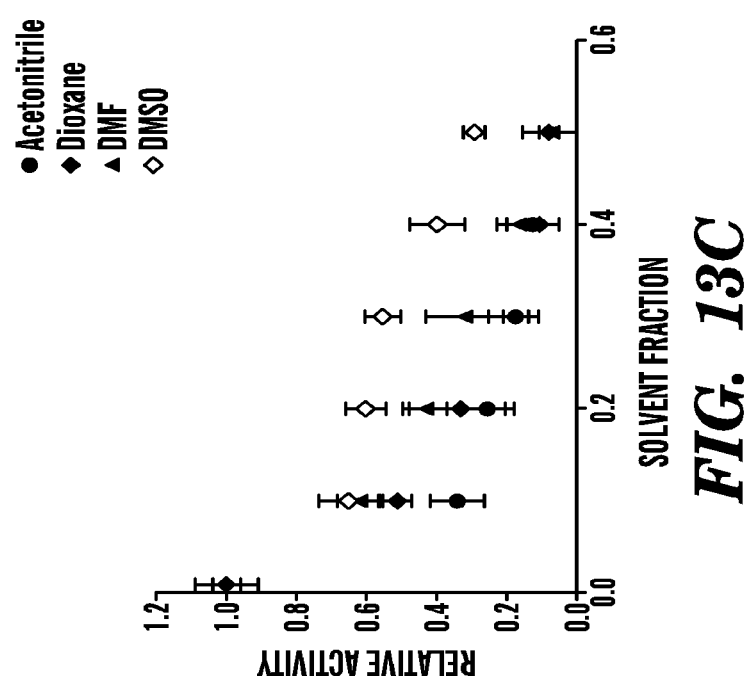

To investigate if there was a limit up to which AmylaseSC could tolerate miscible organic solvents, activity in 10-50% acetonitrile, dioxane, DMF and DMSO was examined (FIG. 13C). Even at 10% solvent, the biofilms lost between 30-60% of their activity and nearly all activity by 50%. Out of the solvents tested. DMSO caused the least activity loss.

To understand the utility of the BIND technology for various biocatalytic applications, it is important to know whether the cells themselves can stay alive at the same time as the catalyst. If the cells die in organic solvents, then they are unable to regenerate the curli network and enzyme, if they are programmed to synthesize both. In this case, the curli functions as a high-surface area polymer similar to synthetic polymer systems, except with a large number of attachment domains. If the cells are able to stay alive, then it is possible to imagine an integrated, renewable system in which both the curli and enzyme are regenerated and the expression of either of those components can be externally controlled. To understand which category the present system falls into, the metabolic activity of the cells was examined as a measure of cell viability (FIG. 13D). The most hydrophobic solvent. decane (log P=5.6), was the only organic solvent in which the cells stayed alive after incubation.

Cell death upon incubation with organic solvents is potentially a beneficial feature of this system, however. One major challenge when working with biofilm reactors is the difficulty to control the growth of the bacteria. Generally, bacteria grow until they clog the reactor, causing the need for the whole system to be cleaned and the biofilm replaced[22]. In the present system, organic solvent can be used to kill the bacteria without destroying the catalyst, effectively eliminating this problem.

Conclusions

Demonstrated herein is a novel platform for the immobilization of an orthogonal enzyme onto the extracellular matrix of an engineered biofilm. Using the BIND technology, biofilms displaying functional handles were created on the curli network of *E. coli*. Subsequently the SpyTag-SpyCatcher technology was used to site-specifically conjugate α-Amylase to the biofilms.

The novelty of the BIND system lies in the ability to create a functionalizable polymer surface that is a scalable alternative to environmentally unfriendly synthetic polymers. Unlike most such polymers, CsgA-ST expressing curli fibers displays functional handles that can be easily modified by any enzyme expressed as a fusion protein with SpyCatcher. Like enzymes displayed on synthetic polymers, displaying enzymes using BIND allows biocatalysis on a living surface without the mass transfer limitations in uniting the substrate and the enzyme in a whole cell catalyst.

Furthermore, all parts of the system are genetically controllable, from the synthesis of the curli fibers to the expression of the enzyme-SpyCatcher fusion protein, making this technology highly adaptable to many applications. The BIND platform at its core is an immobilization strategy and this paper further demonstrates that BIND can be used to display enzymes that are then protected from harsh environmental conditions. Vast amount of research effort is placed, and will be placed in the future, in optimizing enzymes for the catalysis of synthetic intermediates for applications such as pharmaceutical synthesis and breakdown. The BIND system eliminates the need to reengineer bacteria to incorporate these new enzymes in whole cell or biofilm catalysis by allowing the researcher to simply switch out the enzyme attached to curli.

Another advantage of the BIND system is that the functional state of the cells is irrelevant to the catalysis. In whole cell biofilm catalysis, only a fraction of cells are performing the actual catalytic function[22,32], while the rest of the cells may be growing, inactive or dead. Furthermore, the metabolic activity of cells shifts during the biofilm maturation process, so the activity is not constant during the lifetime of the experiment[33]. Since the enzymes are displayed on the external polymer network in BIND, their ability to catalyze a reaction is independent of the stage of the cell cycle.

It is contemplated herein that the methods and compositions described herein permit displaying multiple enzymes on curli, either by using SpyCatcher-SpyTag immobilization only or by using a combination of immobilization domains.

This would produce biofilms that can synthesize or break down molecules through multiple enzymatic steps. As shown previously, clustering of sequential enzymatic steps on the nanoscale has advantages in terms of the efficiency of the catalytic process[34].

Finally, development of enzyme display using BIND permits the integration of the curli and enzyme synthesis machinery into the same bacterium. Integrating curli and enzyme synthesis machinery would allow the enzyme-Spy-Catcher fusion to be expressed and secreted by the immobilized bacteria, eliminating the need for a separate protein isolation step. This would lead to the creation of a completely self-functionalizing catalytic surface. Potential applications of such a technology would lie in many forms of 'green' biocatalysis, including in pharmaceutical synthesis, breakdown of pharmaceuticals in wastewater, removal of contaminants from groundwater or the creation of catalytic surfaces for bioenergy.

References

1. Sheldon, R. A. & Rantwijk, F. V. Biocatalysis for Sustainable Organic Synthesis. *Aust. J. Chem.* 57, 281 (2004).
2. Wohlgemuth, R. Modular and scalable biocatalytic tools for practical safety, health and environmental improvements in the production of speciality chemicals. *Biocatal Biotransformation* 25, 178-185 (2007).
3. Murphy, C. D. The microbial cell factory. *Org. Biomol. Chem.* (2011).
4. Pollard, D. J. & Woodley, J. M. Biocatalysis for pharmaceutical intermediates: the future is now. *Trends in Biotechnology* (2007).
5. Eriksen, D. T., Lian, J. & Zhao, H. Journal of Structural Biology. *Journal of Structural Biology* 185, 234-242 (2014).
6. Leon, R., Fernandes, P., Pinheiro, H. M. & Cabral, J. Whole-cell biocatalysis in organic media. *Enzyme and Microbial Technology* 23, 483-500 (1998).
7. Chen, R. R. Permeability issues in whole-cell bioprocesses and cellular membrane engineering. *Appl Microbiol Biotechnol* 74, 730-738 (2007).
8. Halan, B., Buehler, K. & Schmid, A. Biofilms as living catalysts incontinuous chemical syntheses. *Trends in Biotechnology* 30, 453-465 (2012).
9. Mark, J. H. & Rebecca, J. M. Biofilms and their engineered counterparts: A new generation of immobilised biocatalysts. *Catal. Sci. Technol.* 2, 1544-1547 (2012).
10. Zhou, Z. & Hartmann, M. Recent Progress in Biocatalysis with Enzymes Immobilized on Mesoporous Hosts. *Top Catal* 55, 1081-1100 (2012).
11. Wang, Z., van Oers, M. C. M., Rutjes, F. P. J. T. & van Hest, J. C. M. Polymersome Colloidosomes for Enzyme Catalysis in a Biphasic System. *Angew. Chem. Int. Ed.* 51, 10746-10750 (2012).
12. Costerton, J. W., Lewandowski, Z., Caldwell, D. E., Korber, D. R. & Lappin-Scott, H. M. Microbial biofilms. *Annu. Rev. Microbiol.* 49, 711-745 (1995).
13. Fang, H. H. P., Xu, L.-C. & Chan, K.-Y. Effects of toxic metals and chemicals on biofilm and biocorrosion. *Water Res.* 36, 4709-4716 (2002).
14. Harrison, J. J., Ceri, H. & Turner, R. J. Multimetal resistance and tolerance in microbial biofilms. *Nature Publishing Group* 5, 928-938 (2007).
15. Gross, R., Lang, K., BÃ¼hler, K. & Schmid, A. Characterization of a biofilm membrane reactor and its prospects for fine chemical synthesis. *Biotechnol. Bioeng.* n/a-n/a (2009). doi:10.1002/bit.22584
16. van Bloois, E., Winter, R. T., Kolmar, H. & Fraaije, M. W. Decorating microbes: surface display of proteins on *Escherichia coli*. *Trends in Biotechnology* 29, 79-86 (2011).
17. Chapman, M. R. Role of *Escherichia coli* Curli Operons in Directing Amyloid Fiber Formation. *Science* 295, 851-855 (2002).
18. Chen, A. Y. et al. Synthesis and patterning of tunable multiscale materials with engineered cells. *Nat Mater* (2014). doi:10.1038/nmat3912
19. Van Gerven, N. et al. Secretion and functional display of fusion proteins through the curli biogenesis pathway. *Molecular Microbiology* 91, 1022-1035 (2014).
20. Zakeri, B. et al. Peptide tag forming a rapid covalent bond to a protein, through engineering a bacterial adhesin. *Proc. Natl. Acad. Sci. U.S.A.* 109, E690-7 (2012).
21. Sletten, E. M. & Bertozzi, C. R. Bioorthogonal chemistry: fishing for selectivity in a sea of functionality. *Angew. Chem. Int. Ed. Engl.* 48, 6974-6998 (2009).
22. Qureshi, N., Annous, B. A., Ezeji, T. C., Karcher, P. & Maddox, I. S. Microbial Cell Factories |Full text| Biofilm reactors for industrial bioconversion processes: employing potential of enhanced reaction rates. *Microb Cell Fact* 4, 24 (2005).
23. Stewart, P. S. Diffusion in Biofilms. *J. Bacteriol.* 185, 1485-1491 (2003).
24. Di Russo, N. V., Estrin, D. A., Martf, M. A. & Roitberg, A. E. pH-Dependent Conformational Changes in Proteins and Their Effect on Experimental pKas: The Case of Nitrophorin 4. *PLoS Comput Biol* 8, e1002761 (2012).
25. Nielsen, J. E., Borchert, T. V. & Vriend, G. The determinants of α-amylase pH-activity profiles. *Protein Engineering* 14, 505-512 (2001).
26. Sinisterra, J. V. & Dalton, H. in *Progress in Biotechnology* 11, 416-423 (Elsevier, 1996).
27. Hertzberg, S., Kvittingen, L., Anthonsen, T. & SkjAk-Brwk, G. Alginate as immobilization matrix and stabilizing agent in a two-phase liquid system: Application in lipase-catalysed reactions. *Enzyme and Microbial Technology* 14, 42-47 (1992).
28. Kawakami, K., Tsuruda, S. & Miyagi, K. Immobilization of microbial cells in a mixed matrix of silicone polymer and calcium alginate gel: epoxidation of 1-octene by *Nocardia corallina* B-276 in organic media. *Biotechnol. Prog.* 6, 357-361 (1990).
29. Muñoz, R., Daugulis, A. J., Hemindez, M. & Quijano, G. Biotechnology Advances. *Biotechnology Advances* 30, 1707-1720 (2012).
30. Brink, L & Tramper, J. Modelling the effects of mass transfer on kinetics of propene epoxidation of immobilized *Mycobacterium* cells: 1. Pseudo-one-substrate conditions and negligible product inhibition. *Enzyme and Microbial Technology* 8, 281-288 (1986).
31. Laane, C., Boeren, S., Vos, K. & Veeger, C. Rules for optimization of biocatalysis in organic solvents. *Biotechnol. Bioeng.* 30, 81-87 (1987).
32. Qureshi, N., Paterson, A. H. J. & Maddox, I. S. Model for continuous production of solvents from whey permeate in a packed bed reactor using cells of *Clostridium acetobutylicum* immobilized by adsorption onto bonechar. *Appl Microbiol Biotechnol* 29, 323-328 (1988).
33. Jones, K. & Bradshaw, S. B. Biofilm formation by the enterobacteriaceae: a comparison between *Salmonella* enteritidis, Escherichia coli and a nitrogen-fixing strain of Klebsiella pneumoniae. J. Appl. Bacteriol. 80, 458-464 (1996).

34. Schoffelen, S. & van Hest, J. C. M. Multi-enzyme systems: bringing enzymes together in vitro. Soft Matter 8, 1736 (2012).

Example 5: Programmable Biofilm-Based Materials from Engineered Curl Nanofibers

Self-assembling living systems that are autonomously generating, renewable, and programmable are the next generation of advanced biomaterials. Described herein is "Biofilm-Integrated Nanofiber Display" (BIND) as a strategy for the programmable functionalization of the E. coli biofilm matrix by genetically appending various peptides to the amyloidogenic protein CsgA(1), a biofilm proteinaceous component. CsgA fusion proteins are successfully secreted by the cellular export machinery, self-assemble into amyloid nanofiber networks, and display the peptide of interest in high density. The displayed peptide domains confer various non-natural functions to the biofilms, including adhesion to specific surfaces, nanoparticle templating, protein immobilization, or a combination thereof. BIND is a novel strategy for the broad functionalization of biofilms and demonstrates the utility of biofilms as a designable biomaterial.

In the last century, advances in our understanding of bacterial systems have expanded the role of the microbe from being regarded solely as a health threat to being exploited as genetically programmable factories for the production of biomolecules and chemicals. Bacterial biofilms are embarking on a similar trajectory vis-&-vis functional advanced materials. The majority of bacteria in the natural world exist as biofilms: organized communities of cells ensconced in a network of extracellular polysaccharides, proteins, and other biomolecular components(2). This extracellular matrix protects bacteria from environmental rigors and mediates substrate adhesion, thus promoting microbial persistence and pathogenicity.

Hence, most biofilm research has focused their eradication due to the negative roles biofilms play in clinical infection. Described herein is the domestication of biofilms as a platform for a programmable and modular self-assembling nanomaterial, with the bacterium serving as a living foundry for the synthesis of its raw building blocks, its assembly into higher order structures, and its maintenance over time. While there has been limited investigation into the use of naturally occurring biofilms for beneficial purposes such as energy generation(3), wastewater treatment(4) and biotransformations(5), their widespread use is hindered by a lack of methods to rationally engineer biofilm formation, morphology, adhesion, and function. Any engineering of biofilms to date has focused on altering the cellular populations rather than the biofilm material itself. Although methods exist to display peptides and proteins on various extracellular scaffolds(6), efforts to rationally engineer the molecular structure and properties of the biofilm matrix have, to our knowledge, been completely absent.

The present approach, described herein, to engineering the biofilm extracellular matrix for practical applications focuses on the curli system—the primary proteinaceous structural component of E. coli biofilms. Curli are highly robust functional amyloid nanofibers with a diameter of ~7 nm that form a tangled network encapsulating the cells. Curli are formed from the extracellular self-assembly CsgA, a small secreted 13 kDa protein. A homologous outer-membrane protein, CsgB, nucleates CsgA assembly and also anchors the nanofibers to the bacterial surface. The curli biosynthetic operon contains seven genes (csgA-G)(1), whose products mediate the processing (CsgE, F), secretion (CsgC, G), and transcriptional regulation (CsgD) of CsgA and CsgB.

The curli system exhibits numerous features that make it an ideal platform for the type of materials engineering by way of synthetic biology described herein. First, since the curli nanofiber is composed primarily of one protein, it presents a tractable entry point towards creating a large diversity of biofilm extracellular matrices with conventional genetic engineering methods. In contrast, it would be more difficult to engineer the exopolysaccharide component of biofilms, as polysaccharide synthesis is often tied to multi-step pathways with a limited tolerance for chemically diverse monomers compared to the protein synthetic machinery. Second, the functional amyloid fibers formed by CsgA are extremely robust, being able to withstand boiling in detergents(7) and extended incubation in solvents, increasing their potential utility in harsh environments. Similar amyloid nanofibers have been shown to have a strength comparable to steel and a mechanical stiffness comparable to silk(8), suggesting that biofilms with high amyloid content may be able to withstand mechanically demanding environments. Third, functional amyloid fibrils are abundant in many naturally occurring bacterial biofilms and can constitute up to 10-40% of the total biovolume(9), suggesting that curli can be artificially engineered to comprise a significant portion of the biofilm. In addition, although analogous extracellular functional amyloids are produced by many bacteria, the curli system is the best studied and is native to the canonical model bacteria, making it an attractive starting platform for the development of engineered materials. Lastly, recent findings have shown that the curli system can efficiently export amyloidogenic polypeptides and was capable of expressing a functional CsgA-camelid antibody fragment fusion, demonstrating that the curli system can be used in a broad and modular way for the display of functional peptides throughout the E. coli biofilm matrix (10, 11).

Figure 16A:
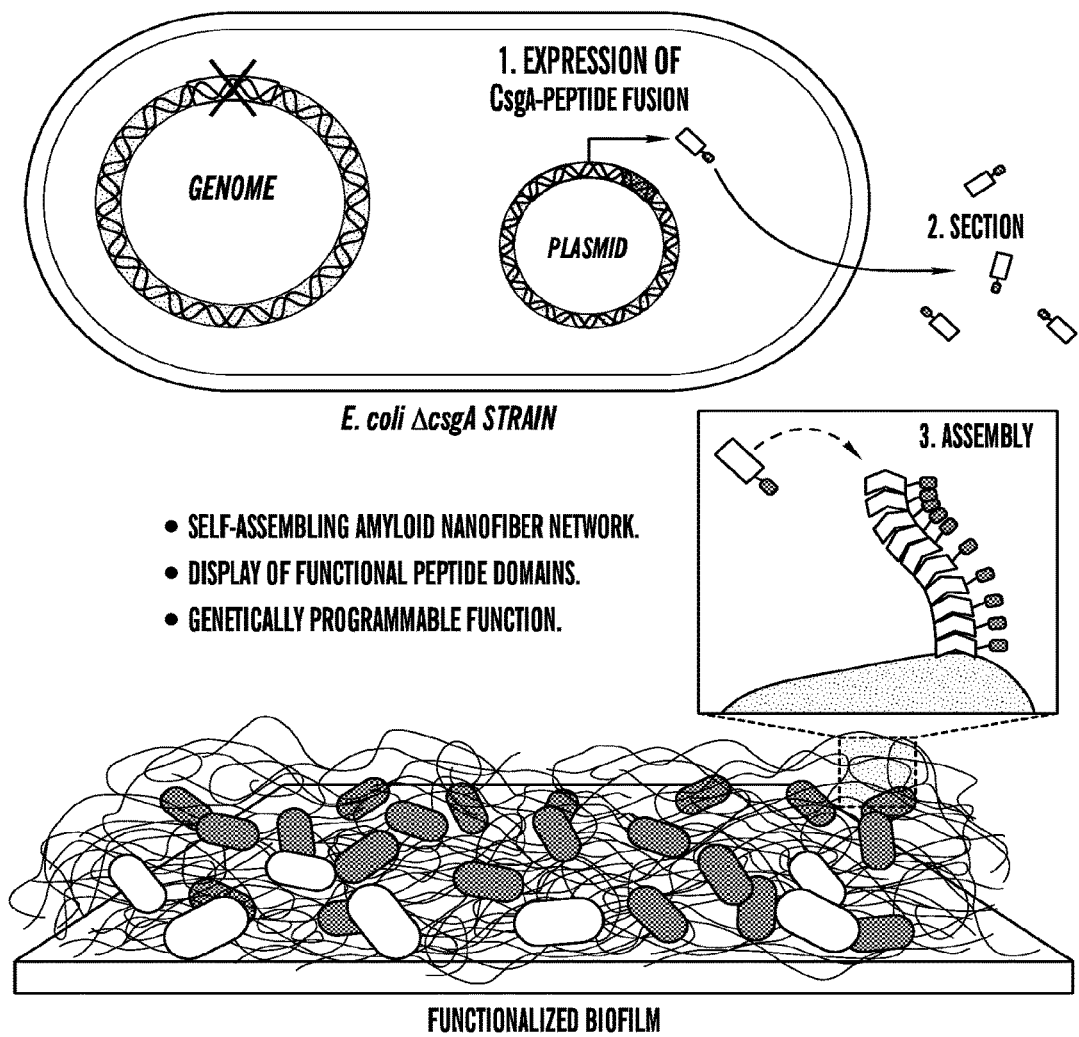
FIGS. 16A-16P demonstrate the genetic programming and modularity of the BIND system.

The BIND system enables the precise genetic programming of the E. coli biofilm matrix by fusing functional peptide domains to the CsgA protein (FIG. 16A). It is demonstrated herein that the chimeric CsgA variants are secreted by the native cellular export machinery and assemble into networks of curli fibers that resemble the wild-type system. It is also demonstrated that this technique is compatible with a wide range of peptide domains of various lengths and secondary structures. Lastly, it is demonstrated that the peptide domains maintain their function after secretion and assembly and confer artificial functions to the biofilm as a whole. In three proof-of-concept experiments, the ability to program different functions into the biofilm is highlighted: specific adhesion to an abiotic surface, nanoparticle templating, and site-specific covalent immobilization of an arbitrary functionalized recombinant protein.

Figure 20B:
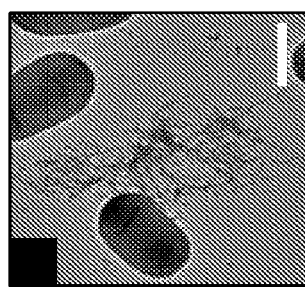
FIGS. 20A-20N depict TEM images of the peptide fusion BIND library transformed into LSR10 (MC4100, csgA) cells with no CsgA (FIG. 20A), wt-CsgA (FIG. 20B), and the BIND peptide panel (see Table 1): HIS (FIG. 20C), GBP (FIG. 20D), FLAG (FIG. 20E), CNBP (FIG. 20F), A3 (FIG. 20G), CLP12 (FIG. 20H), QBP1 (FIG. 20I), SpyTag (FIG. 20J), MBD (FIG. 20K), CT43 (FIG. 20L), AFP8 (FIG. 20M), and Mms6 (FIG. 20N). Scale bars, 1 μm.
Figure 20A:
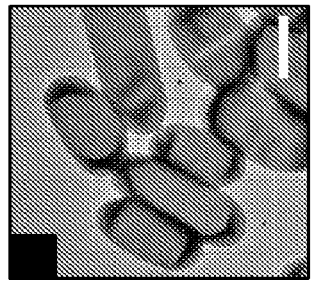
Figure 20F:
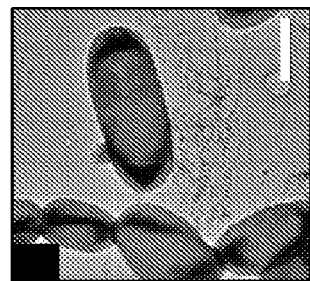
Figure 20E:
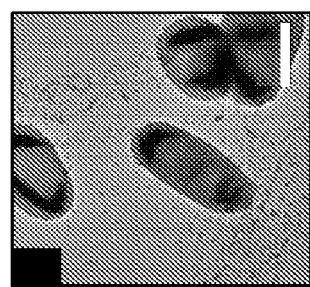
Figure 20D:
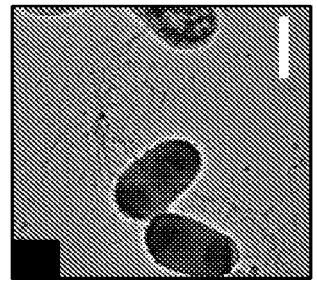
Figure 20C:
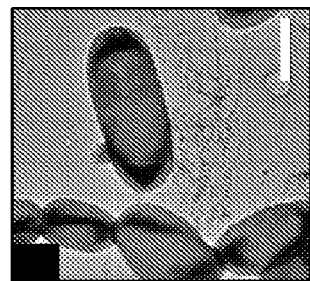
Figure 20J:
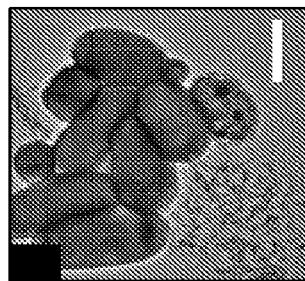
Figure 20N:
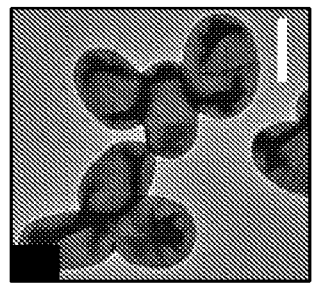
Figure 20I:
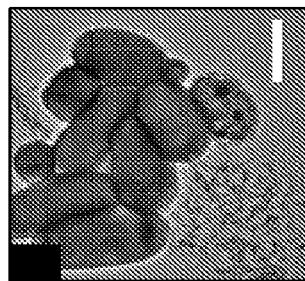
Figure 20M:
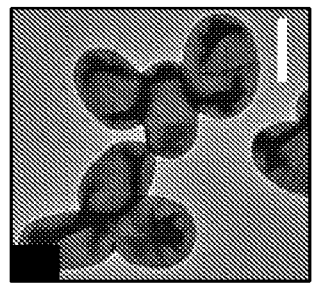
Figure 20H:
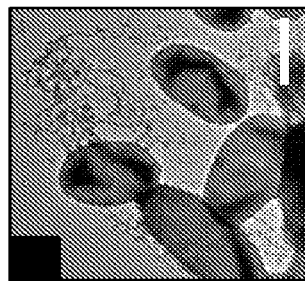
Figure 20L:
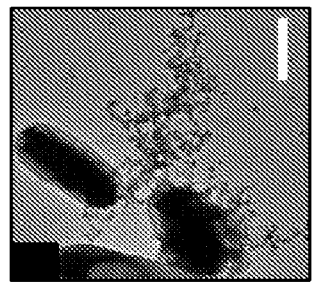
Figure 20G:
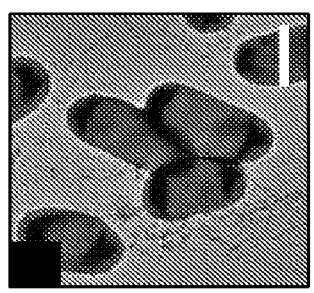
Figure 20K:
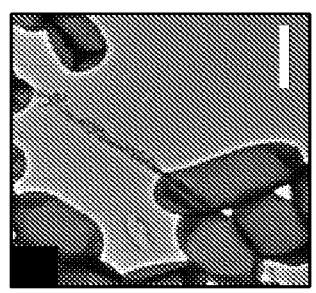

In order to determine suitable fusion points to append peptides to CsgA, a library (FIG. 3) was generated consisting of N- and C-terminal fusions to a peptide domain known to bind strongly to stainless steel surfaces(12). Terminal fusions were chosen to allow for the integration of both linear and circularly constrained peptides. Three variants were prepared for each terminus with varying flexible linker lengths. The csgA variants were expressed in a csgA deletion strain of E. coli (LSR10) that retains the remaining curli processing machinery under native regulation(13). This strain does not produce flagella, cellulose, or LPS Opolysaccharides(14-16). Thus any extracellular fibers could be attributed solely to the selfassembly of heterologously engineered CsgA fusion mutants. An amyloid-staining colorimetric dye, Congo Red (CR), was used to determine the extent of curli production for the various mutants. Based on this assay, only the C3 fusion site with the longest C-terminal linker between CsgA and MBD was able to form an appreciable amount of amyloid fibers (FIG. 1B). It is possible that the N-terminal fusions inhibited cellular export due to their proximity to the CsgGspecific export recognition sequence. Scanning (SEM, FIG. 16M) and transmission electron microscopy (TEM, FIG. 20M) characterization of the C3 mutant curli fibers confirmed that they exhibited morphology similar to the wild-type CsgA fibers.

Figure 16B:
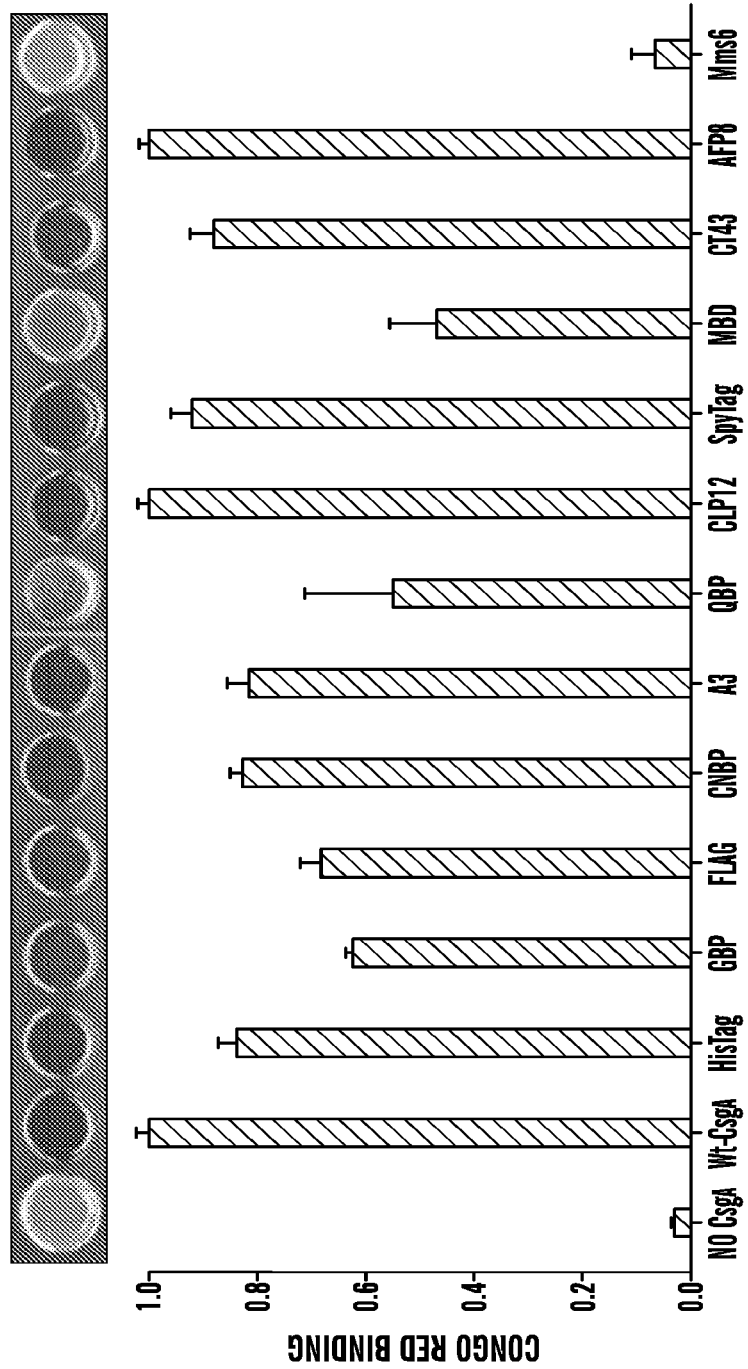
FIG. 16B depicts quantitative assessment of the Congo Red binding from quadruplicate YESCA-CR spotted cultures using intensity quantitation (ImageJ™) measures the relative amyloid produced for each CsgA-peptide fusion, normalized to wild-type CsgA. A representative set of culture spots onto YESCA-CR agar is shown at the top.
Figure 16H:
Figure 16D:
Figure 16G:
Figure 16C:
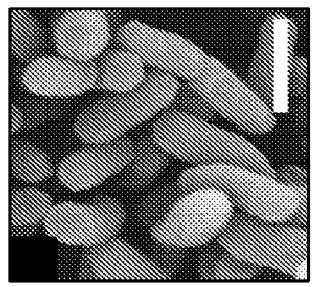
Figure 16F:
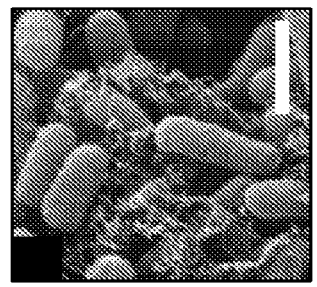
Figure 16E:
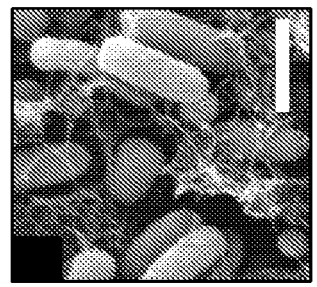
Figure 16I:
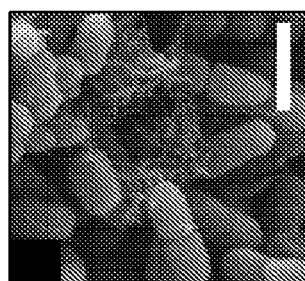
Figure 16J:
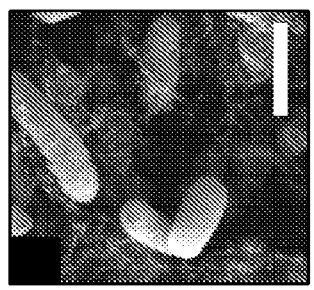
Figure 16K:
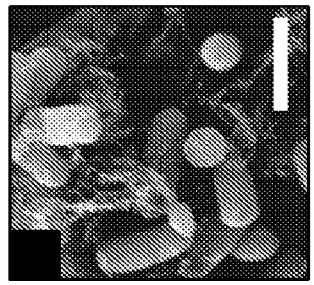
Figure 16L:
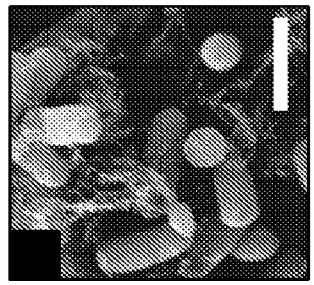
Figure 16M:
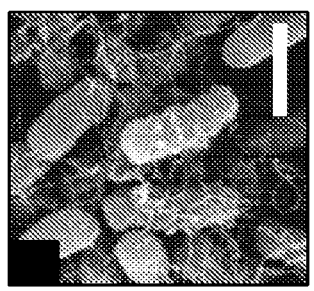
Figure 16N:
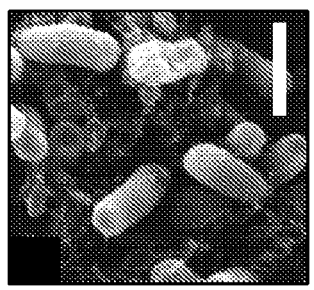
Figure 16O:
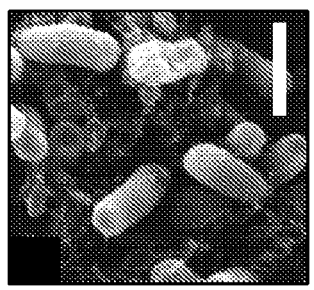
Figure 16P:
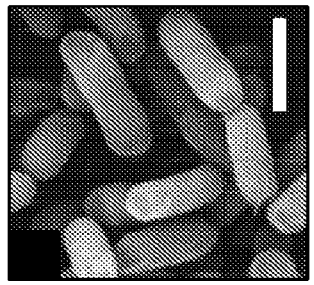
Figure 17:
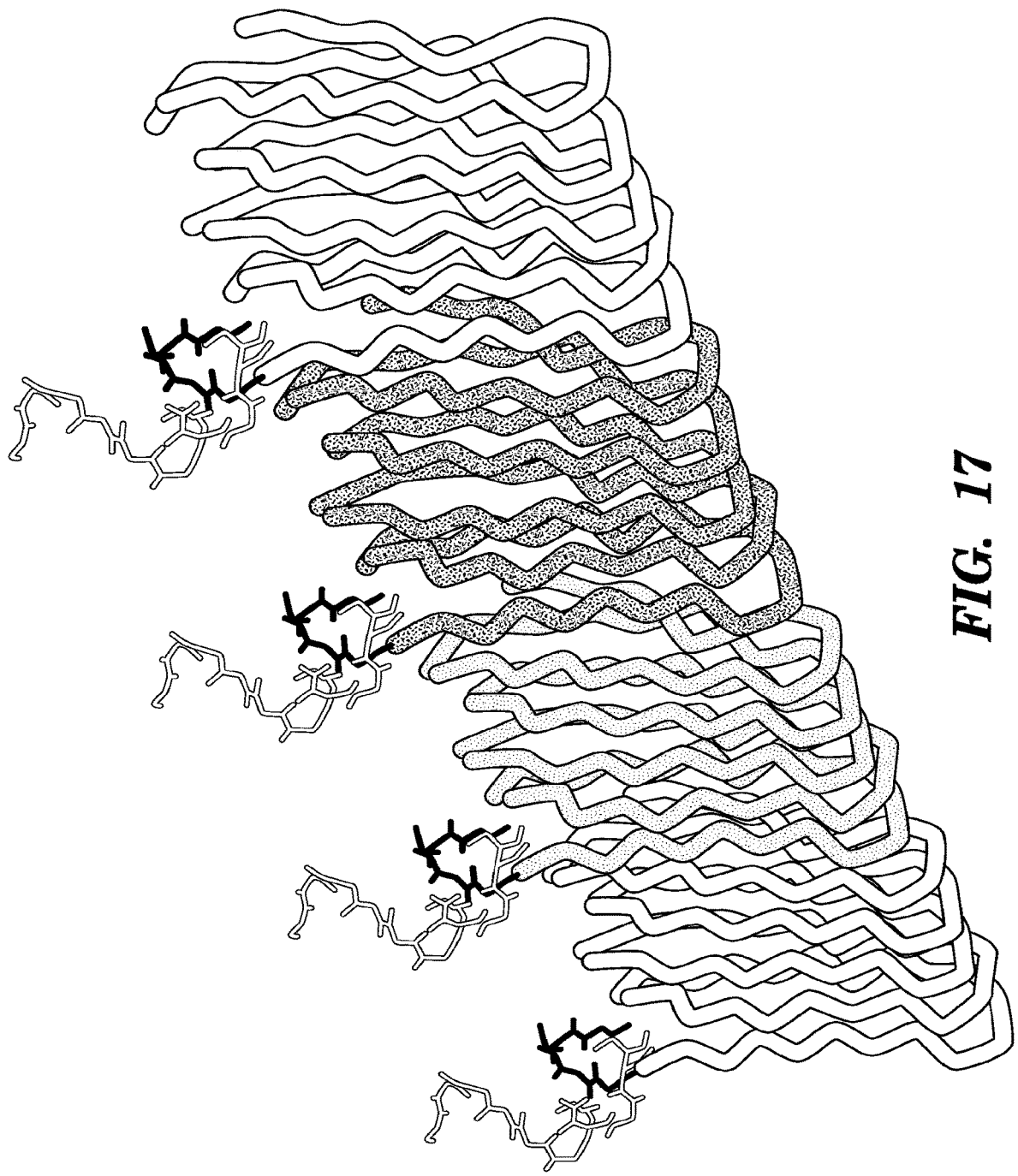
FIG. 17 depicts a three-dimensional protein model of the BIND system based on the C3 insertion site. Self-assembling CsgA amyloid domains are derived from protein threading of the CsgA sequence onto an AgfA homology model. An example peptide domain, SpyTag (see Table 1), is shown in and the 6-residue flexible linker. This peptide structure was predicted using PepFold and all structural manipulation performed in PyMol.
Figure 21B:
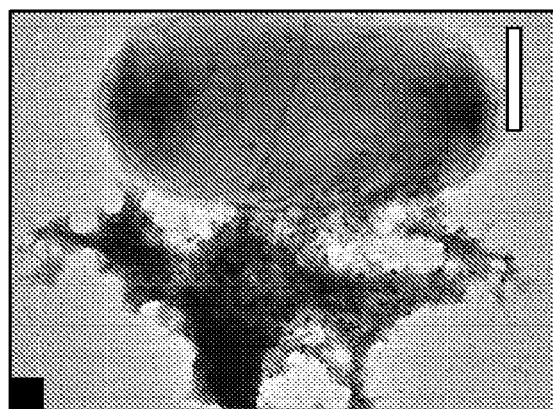
FIGS. 21A-21B demonstrate immunogold TEM of FLAG-tagged BIND and wildtype CsgA nanofibers.
Figure 21A:
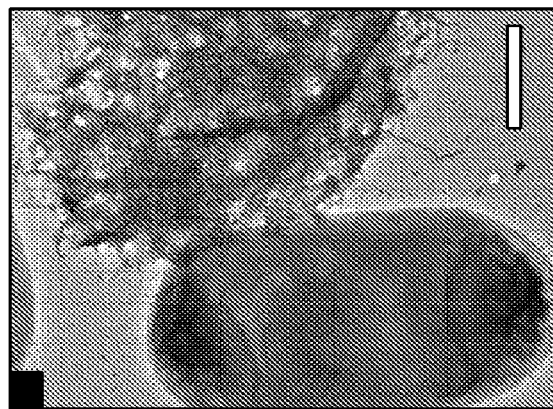
Figure 22:
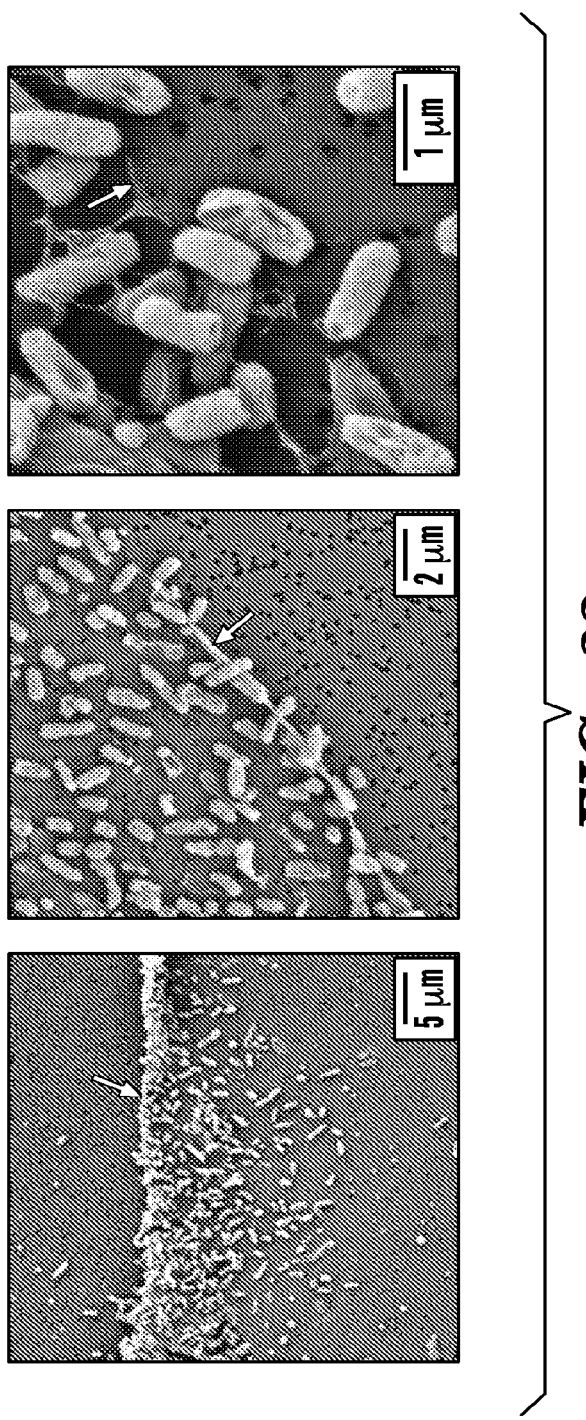
FIG. 22 depicts images demonstrating that FLAG-BIND biofilms occur as extensive 2D amyloid sheets. SEM images of meshlike sheets formed by LSR10 cells transformed with CsgA-FLAG are shown at various magnifications, filtered onto Nuclepore membranes. The arrows in each image points to the leading edge of the amyloid film.

Having identified a suitable fusion site, a library of 12 peptide domain fusions was created to test the effect of peptide length and structure on secretion and assembly. The library members ranged in length from 7 to 59 amino acids, encoded a wide variety of functions(17-28), and were fused to CsgA C-terminus using the six-amino acid flexible linker (Table 1, FIG. 17). The library members were cloned into LSR10 cells and probed for the formation of curli by CR staining. Quantitative differences in curli production between library members were monitored by measuring the staining intensity of transformants spotted on CR plates (FIG. 16B). SEM (FIG. 16C-16P) and TEM (FIGS. 20A-20N) of the modified curli biofilms supports the CR data for the production of extracellular amyloid. Overall, most small peptide fusions were tolerated by the curli export machinery and could successfully assemble into amyloid networks. Immunostaining of BIND biofilms expressing the CsgA-FLAG mutant with anti-FLAG antibody confirmed the presence and accessibility of the peptide domain (FIGS. 21A-21B). The only mutant for which there was no positive CR staining was the 59-amino acid Mms6 protein domain, confirming previous findings that polypeptides with long sequences or inherent structure may not be exported efficiently through the CsgG outer membrane transporter, which has a pore size of 2 nm (10, 29). For the curli-producing strains, the CsgA-peptide fusions assemble into nanoscale fibers similar in morphology to wt-CsgA (FIG. 16C-16O). The fibers display a characteristic tangled morphology and appear to be closely associated with the cell surface in meshlike networks, suggesting that peptides of arbitrary sequence and function could be displayed on the surface of curli fibers. Some of the BIND variants, such as the FLAG-BIND, exhibited the ability to form extensive thin, fabric-like 2D meshes unseen in normal curli biofilms, suggesting that the platform can also be manipulated to alter the macromolecular architecture of biofilms (FIG. 22).

The true value of the BIND system is in its ability to perform as an active surface coating whose function can be genetically programmed in a modular fashion. As a demonstration of some of these capabilities, three peptides were selected from Table 1 (MBD, A3 and SpyTag) and their ability to introduce new functions to curli-producing biofilms tested, specifically, the ability to enhance adhesion to abiotic surfaces, to biotemplate the growth of inorganic nanoparticles, and to covalently immobilize full-length proteins. For these studies PHL628, a csgA deletion strain which overproduces the curli processing machinery and is also able to produce CR-positive biofilms was used (FIG. 4) (30).

In order to make BIND an efficient platform for developing interfacial materials, it will be critical to tune the nanofiber adhesion to specific abiotic surfaces. As an example of this capability, the adhesion of E. coli cells displaying MBD to 304L stainless steel, the most versatile and widely used steel alloy, was tested. PHL628 cells expressing the CsgA-MBD mutant were spotted onto 304L coupons, allowed to adhere for 48 hours, and then vigorously washed in aqueous buffer (FIG. 5A) to remove non-specifically bound cells. Biofilms composed of the CsgA-MBD fusion withstood the washing procedure, while those expressing wt-CsgA or no CsgA were easily washed off the surface (FIGS. 18B-18E). This result demonstrates that BIND programming using MBD is sufficient to impart adhesive function to biofilms. The modularity of the BIND platform lends itself to a plug-and-play approach to the design of biofilm adhesion for applications in bioremediation or chemical synthesis, where non-specific biofilm growth is viewed as a disadvantage. This capability will be particularly useful in applications where patterned surfaces are used to spatially control biofilm formation, or where it is desired to localize biofilm growth to specific materials, as is often the case in industrial bioreactors.

Figure 18C:
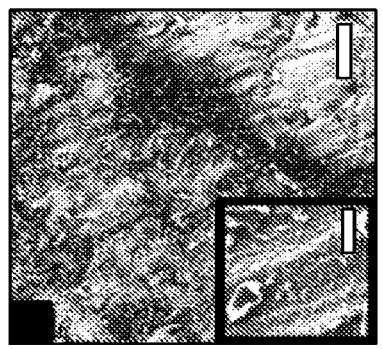
FIGS. 18A-18E demonstrate that BIND biofilms can be programmed to adhere to substrates or biotemplate nanoparticles. Adhesion of PHL628 csgA cells expressing no curli, wild-type CsgA, and CsgAMBD was tested by spotting grown cultures onto a 304L steel coupon and incubating for 48 hours. Cells expressing no curli proteins (FIG. 18A) or wild-type CsgA (FIG. 18B) did not adhere to the steel surface, unlike those expressing the MBD-BIND system (FIG. 18C); scale bars, 10 μm. The inset in (FIG. 18C) shows the biofilm-modified steel surface, scale bar, 1 μm. Silver nanoparticles were template by A3-BIND biofilms incubated in aqueous AgNO3. PHL628 csgA cells expressing either wildtype CsgA or CsgA-A3 were analyzed by TEM after incubation in 147 mM AgNO3 for 4 hours (FIGS. 18D and 18E).
Figure 18B:
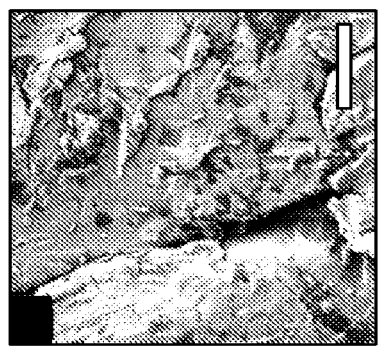
Figure 18A:
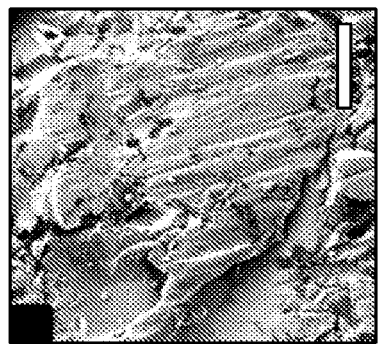
Figure 18E:
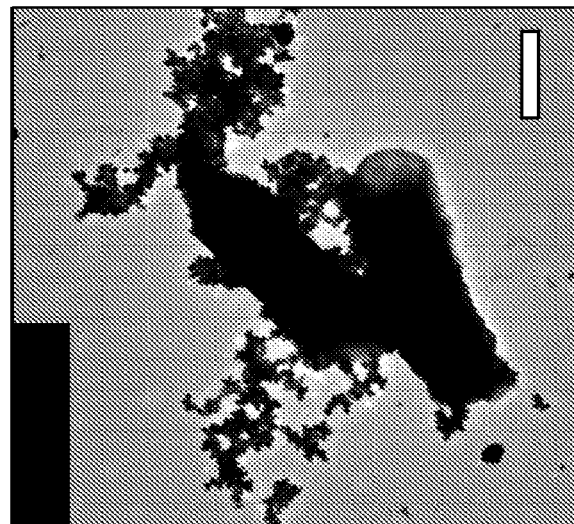
Figure 18D:
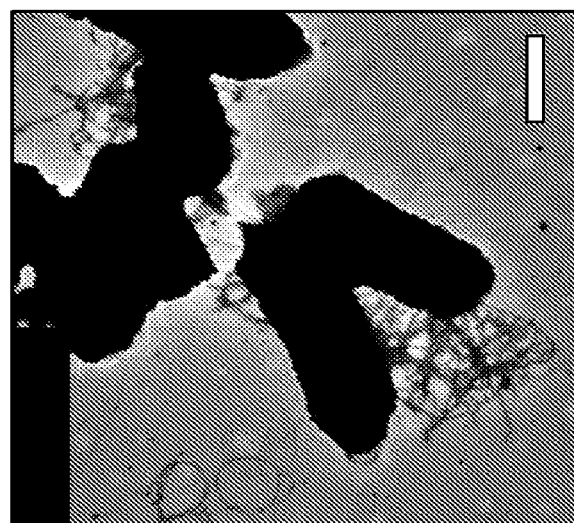
Figure 19A:
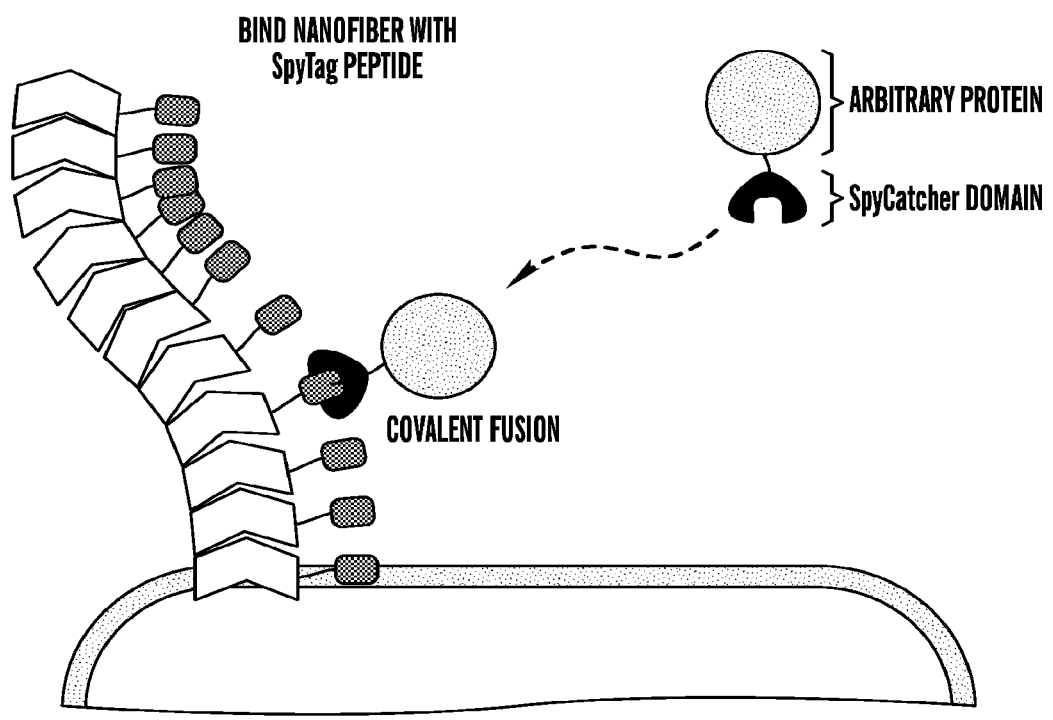
FIGS. 19A-19G demonstrate covalent immobilization of full-length proteins onto curli biofilm.
Figure 19B:
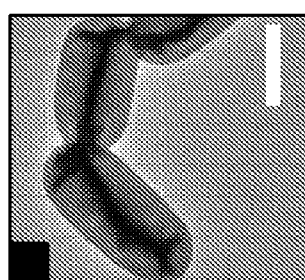
Figure 19C:
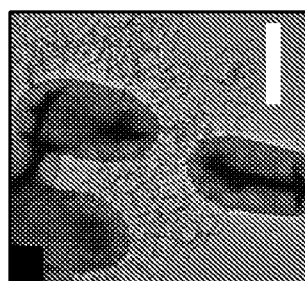
Figure 19D:
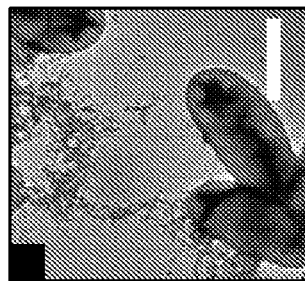
Figure 19E:
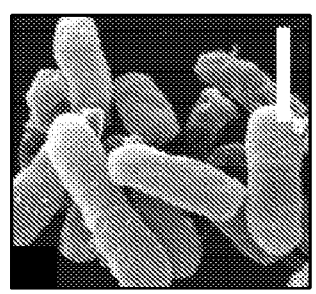
Figure 19F:
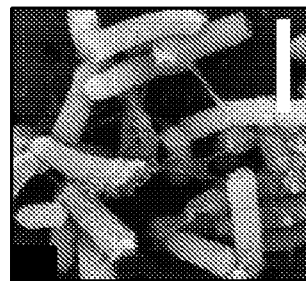
Figure 19G:
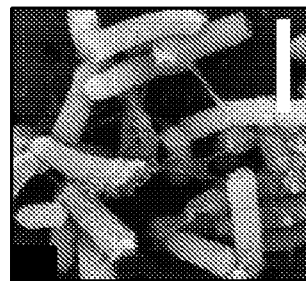

Peptide binding to surfaces can also be used to promote materials templating, which is demonstrated herein using BIND composed of a CsgA-A3 fusion. The A3 peptide was previously developed by phage display to bind silver and has been shown to control the templating of silver nanoparticles. The A3-BIND biofilms demonstrate an enhanced ability to bind to growing silver nanoparticles from a solution of AgNO3 in contrast to the wildtype biofilm (FIGS. 18D-18E). In addition to displaying short peptides, it was reasoned that the utility of the BIND system would be greatly expanded if it could be used to display full proteins of arbitrary length and dimensions to program the biofilm with artificial catalytic, electron transport, or sensing capabilities. A completely genetically encodable strategy was employed (FIG. 19A) to covalently immobilize proteins onto the BIND network, using a split-adhesin system in which a 13-amino acid peptide (SpyTag) forms an isopeptide bond with a 15-kDa protein (SpyCatcher) (31). Accordingly, biofilms displaying the CsgA-SpyTag chimera were grown on a glass substrate using PHL628 cells and formed a characteristic curli network when either wt-CsgA or CsgA-SpyTag were expressed (FIGS. 19B-19G). A SpyCatcber-Venus fusion protein was used to probe for the presence and functionality of the SpyTag domain. Treatment with either SpyCatcher-Venus or a non-functional mutant (SpyCatcherEQ-Venus) revealed that only biofilms expressing CsgA-SpyTag were able to bind SpyCatcber-Venus (FIG. 6F). These results confirm that the SpyTag peptide can be fused to CsgA and maintain its functionality after formation of the curli network. To further simplify the immobilization process, an unpurified cell lysate containing the SpyCatcher fusion protein was used in lieu of purified protein, and obtained similar results (data not shown), thus demonstrating the binding specificity between the CsgASpyTag curli network and its cognate SpyCatcher fusion protein, even in complex mixtures. This feature of BIND will be especially useful in the area of biocatalysis, for the development of an efficient immobilization process for the reuse of an enzyme.

Described herein is an elegant strategy using the BIND platform, whereby the fabrication of the nanofiber scaffold, biosynthesis of the enzyme, and immobilization reaction could all be accomplished by a single engineered bacterial strain without any purification steps.

A key aspect of BIND is that by virtue of the random extracellular self-assembly of curli fibers, the expression of different CsgA fusions will result in a multifunctional biofilm surface. Thus, a BIND structure can be programmed for any combination of adhesion, display, molecular templating, or protein immobilization. This characteristic is demonstrated berien by coculturing CsgA-FLAG and CsgA-SpyTag to produce a bifunctional BIND biofilm that can display the FLAG tag as well as immobilize GFP through the SpyTag-SpyCatcber system (data not shown).

Demonstrated herein is a strategy for the rational molecular design of a microbial extracellular matrix component with the purpose of introducing new function into a biofilm. These results demonstrate that the curli system in E. coli is capable of secreting and assembling a variety of chimeric CsgA-peptide constructs that can self-assemble into an amyloid-based extracellular matrix. The fused peptide domains are displayed in high density on the network surface and maintain their function even after assembly. It is demonstrated herein that three distinct non-natural functions (adhesion to steel surfaces, silver nanoparticle templating, and covalent protein immobilization) can be introduced modularly into E. coli biofilms based on the predetermined functions of various engineered peptide sequences. Importantly, each functional demonstration was accomplished without the need for system re-optimization, suggesting that other sequences can easily be incorporated into the present system to access materials with a range of non-natural functions, and even multiple new functions at once. BIND lends itself to the rapid development of interfacial nanomaterials with functions that can be drawn from the diverse repertoire of known peptides and proteins. These biofilm-based materials can be used in a wide range of environments that may or may not be conducive to cellular survival. In hospitable environments, the encapsulated cells of the biofilm may be induced to self-regenerate or heal the material over time, or alter the material in response to environmental cues. However, in harsher environments, the robust engineered matrix may function on its own without the need for maintenance. The methods and compositions described herein can be used to introduce new function to many other microbial biofilms with analogous functional amyloids (e.g. *Salmonella, Pseudomonas, Bacillus* spp.) to capitalize on the particular features of each wild-type strain. Given that the engineered bacteria proliferate rapidly and require no petroleum-derived raw building blocks in order to biosynthesize the external matrix, BIND may be useful as a scalable and "green" approach to fabricating customized interfacial materials across a wide range of size scales and environments.

Materials and Methods

Cell Strains and Plasmids. All cloning and protein expression was performed in Mach1™ (Invitrogen) and Rosetta™ cells (EMD), respectively. The csgA gene was isolated from *E. coli* K-12 genomic DNA and cloned into pBbE1a, a ColE1 plasmid under control of the Trc promoter. Peptide insert regions were either fully synthesized (Integrated DNA Technologies) or PCR-generated by overlap extension. All cloning was performed using isothermal Gibson Assembly and verified by DNA sequencing.

Curli Biofilm Formation. To produce curli, LSR10 cells or PHL628 cells were transformed with pBbE1a plasmids encoding for CsgA or CsgA-peptide fusions. As a negative control, cells were transformed with empty pBbE1a plasmid. The cells were then streaked or spotted onto YESCA-CR plates, containing 10 g/L of casamino acids, 1 g/L of yeast extract, and 20 g/L of agar. These plates were supplemented with 100 µg/mL of ampicillin, 0.5 mM of IPTG, 25 µg/mL of Congo Red and 5 µg/mL of Brilliant Blue G250. The plates were then incubated for 48 hours at 25° C. and then imaged to determine the extent of Congo Red binding. For the spotted plates, the transformants were grown in YESCA liquid media supplemented with 100 µg/mL of ampicillin and 0.2 mM of ITG for 48 hours at 25° C. before spotting 20 µL onto YESCA-CR plates.

TEM and SEM. Curliated wildtype or BIND cell samples were either directly taken from induced YESCA cultures or scraped from YESCA-CR plates and resuspended in Millipore H2O. For TEM analysis, 5 µL of the sample was spotted onto formvar-carbon grids (Electron Microscopy Sciences), washed with Millipore H2O, and stained with 1% uranyl formate before analysis on a JEOL 1200 TEM. For SEM analysis, samples were applied to Nucleopore filters under vacuum, washed with Millipore H2O and fixed with 2% glutaraldehyde+2% paraformaldehyde overnight at 4° C., followed by fixation in 1% osmium tetroxide. The samples were then washed in Millipore H2O, dehydrated with an increasing ethanol step gradient, followed by a hexamethyldisilazane step gradient before gold sputtering and analysis on a Zeiss Supra55VP™ FE-SEM.

Immunogold TEM. For anti-FLAG immunogold labeling of the BIND cells displaying the FLAG tag, the cells were first adhered to nickel TEM grids as described above. Then, the grids were washed 3× in blocking buffer (PBS+1% BSA), floated face-down on a drop containing a 1:1000 dilution of primary anti-FLAG murine antibody in PBS for 30 minutes, washed in blocking buffer again, and then floated on a drop of 1:1000 diluted anti-mouse 15 nm gold-conjugated antibody for 30 minutes. After a final 3× wash in PBS and then Millipore H2O, the grids were stained with 1% uranyl formate for 15 seconds and imaged on a JEOL 1200™ TEM.

MBD-BIND Binding to 304L Stainless Steel Coupons. Steel alloy 304L coupons (Alabama Specialty Products, Inc.) were cleaned with fine-grit sandpaper, acetone, Millipore water, sonicated in 1M NaOH for 1 hour at 80° C., washed again with Millipore water, and finally rinsed with acetone before air-drying. PHL628 csgA transformants were grown in YESCA media as described above and induced by adding 0.5 mM IPTG and 3% DMSO for 48 hours at 25° C., 150 rpm. Cell cultures were normalized to an OD600 of 1 and 20 µL was spotted onto a 304L coupon. The spotted coupon was placed in a sterile petri dish and placed in 4 C to allow attachment and minimize evaporation. After 48 hours, the coupons were rinsed briefly with PBS, placed in a tube filled with PBS, and vortexed 3× for 30 seconds at a vortex setting of 5. The coupons were then fixed and SEM imaged according to the protocols described above.

Silver Nanoparticle Templating. PHL628 csgA cells were transformed with wild-type CsgA or CsgA-A3 expressing plasmids and induced with 0.2 mM IPTG in YESCA broth containing 100 µg/mL carbenicillin for 48 hours. The cells and curli were isolated by pelleting and then resuspended in PBS+CM. Nickleformvar/carbon TEM grids were floated on drops of these resuspended samples, washed twice with PBS+CM, thrice with mpH2O, and then incubated on a drop containing 147 mM AgNO3 for 4 hours. The grids were then washed thrice with mpH2O and negatively stained and analyzed by TEM as described above.

Biofilm Fluorescence Microscopy Imaging. PHL628 csgA cells transformed with control, wild-type CsgA, and CsgA-SpyTag expressing plasmids were grown up in 20 mL YESCA broth containing 100 µg/mL ampicillin at 30° C. until an OD of 0.6. Plasma-activated and PLL-functionalized coverslips were placed into the cultures and curli expression and biofilm formation were induced by adding 0.5 mM IPTG and 3% DMSO. Cultures were grown at 25° C. and 150 rpm for 48 hours. Slides were removed from the cultures and washed 3×20 min in wash buffer (lx PBS+0.5% TWEEN® 20), shaking at 150 rpm. After the washes, 0.5 mL of 1 mg/mL Venus-SpyCatcher or Venus-SpyCatcher (E77Q) solution (in PBS+1% BSA+0.5% TWEEN®) was added to slides. The biofilms were incubated for 1 hour and then washed 2×20 min with wash buffer. The samples were then stained with SYTO-61 (10 µM) for 20 min and washed with wash buffer 2×15 min shaking at 150 rpm. Slides were then imaged in epifluorescence mode on a Leica Tirf DM16000BM at 60× and 100×. For the multifunctional BIND experiments, cells at an initial OD600 of 2.5 were cultured in MatTek glass-bottom dishes for 72 hours under inducing conditions (YESCA/0.5 mM IPTG/100 ng/mL carbenicillin/3% DMSO). The biofilms were then washed 3×10 min in PBST, blocked with 1% BSA in PBST for 1 hour, and incubated with Venus-SpyCatcher containing clarified cell lysate for 1 hour. The dishes were then extensively washed with 0.1% BSA+PBST under gentle shaking before incubation with an anti-FLAG DyLight® 680 antibody (Pierce) for 1 hour. The samples were washed as before with 0.1% BSA+PBST, fixed with 2% glutaraldehyde+2% paraformaldehyde in 0.1M sodium cacodylate buffer for 15 minutes, and then incubated in PBS+10 mM glycine overnight at 4° C. to eliminate autofluorescence. All multifunctional BIND samples were analyzed on Leica SP5 X MPM Inverted Confocal Microscope.

SpyCatcher-Venus Construction and Expression. Rosetta™ cell transformants containing pDEST14-SpyCatcher-Venus were used to inoculate 500 mL cultures supplemented with 100 g/mL ampicillin and grown for 6 hours at 37° C. until an OD of 0.6. SpyCatcher-Venus expression was induced with 0.5 mM IPTG and allowed to express overnight at 18° C. Cells were harvested and lysed and SpyCatcher-Venus was purified on a Ni-NTA column. Protein was collected, buffer exchanged into 50 mM phosphate buffer/50 mM NaCl, pH 7, concentrated and stored at −80° C. until further use. The E77Q mutant was purified in a similar manner.

References

1. M. R. Chapman, L S. Robinson, J. S. Pinkner, R. Roth, J. Heuser, M. Hammar, S. Normark, S. J. Hultgren, Role of *Escherichia coli* curli operons in directing amyloid fiber formation. *Science* 295, 851-855 (2002); published online EpubFeb (295/5556/851 [pii] 10.1126/science.1067484).
2. H.-C. Flemming, J. Wingender, The biofilm matrix. *Nature Reviews Microbiology*, (2010); published online EpubAug 02 (10.1038/nrmicro2415).
3. B. E. Logan, Exoelectrogenic bacteria that power microbial fuel cells. *Nature Reviews Microbiology* 7, 375-381 (2009).
4. R. Singh, D. Paul, R. K. Jain, Biofilms: implications in bioremediation. *Trends Microbiol* 14, 389-397 (2006); published online EpubSep (10.1016/j.tim.2006.07.001).
5. B. Halan, K. Buehler, A. Schmid, Biofilms as living catalysts in continuous chemical syntheses. *Trends Biotechnol* 30, 453-465 (2012); published online EpubSep (10.1016/j.tibtech.2012.05.003).
6. C. G. Ullman, L. Frigotto, R. N. Cooley, In vitro methods for peptide display and their applications. *Briefings in Functional Genomics* 10, 125-134 (2011); published online EpubJun 30 (10.1093/bfgp/elr010).
7. M. Hammar, A. Arnqvist, Z. Bian, A. Olsen, S. Normark, Expression of two csg operons is required for production of fibronectin- and congo red-binding curli polymers in *Escherichia coli* K-12. *Mol Microbiol* 18, 661-670 (1995); published online EpubNov (
8. J. F. Smith, T. P. Knowles, C. M. Dobson, C. E. Macphee, M. E. Welland, Characterization of the nanoscale properties of individual amyloid fibrils. *Proc Natl Acad Sci USA* 103, 15806-15811 (2006); published online EpubOct (10.1073/pnas.0604035103).
9. P. Larsen, J. L Nielsen, D. Otzen, P. H. Nielsen, Amyloid-like adhesins produced by floc-forming and filamentous bacteria in activated sludge. *Appl Environ Microbiol* 74, 1517-1526 (2008); published online EpubMar (10.1128/AEM.02274-07).
10. N. Van Gerven, P. Goyal, G. Vandenbussche, M. De Kerpel, W. Jonckheere, H. De Greve, H. Remaut, Secretion and functional display of fusion proteins through the curli biogenesis pathway. *Mol Microbiol*, (2014); published online EpubJan (10.1111/mmi.12515).
11. V. Sivanathan, A. Hochschild, Generating extracellular amyloid aggregates using *E. coli* cells. *Genes Dev* 26, 2659-2667 (2012); published online EpubDec (10.1101/gad.205310.112).
12. C. L Giltner, E. J. van Schaik, G. F. Audette, D. Kao, R. S. Hodges, D. J. Hassett, R. T. Irvin, The *Pseudomonas aeruginosa* type IV pilin receptor binding domain functions as an adhesin for both biotic and abiotic surfaces. *Molecular Microbiology* 59, 1083-1096 (2006); published online EpubMar (10.1111/j.1365-2958.2005.05002.x).
13. X. Wang, Y. Zhou, J. J. Ren, N. D. Hammer, M. R. Chapman, Gatekeeper residues in the major curlin subunit modulate bacterial amyloid fiber biogenesis. *Proceedings of the National Academy of Sciences* 107, 163-168 (2010); published online EpubFeb 05 (10.1073/pnas.0908714107).
14. M. J. Casadaban, Transposition and fusion of the lac genes to selected promoters in *Escherichia coli* using bacteriophage lambda and Mu. *J Mol Biol* 104, 541-555 (1976); published online EpubJul (
15. D. Liu, P. R. Reeves, *Escherichia coli* K12 regains its O antigen. *Microbiology* 140 (Pt 1), 49-57 (1994); published online EpubJan (
16. X. Zogaj, M. Nimtz, M. Rohde, W. Bokranz, U. Römling, The multicellular morphotypes of *Salmonella typhimurium* and *Escherichia coli* produce cellulose as the second component of the extracellular matrix. *Mol Microbiol* 39, 1452-1463 (2001); published online EpubMar (
17. E. Hochuli, W. Bannwarth, H. Dobeli, R. Gentz, D. Stuber, Genetic Approach to Facilitate Purification of Recombinant Proteins with a Novel Metal Chelate Adsorbent. 6, 1321-1325 (1988).
18. S. N. Kim, Z. Kuang, J. M. Slocik, S. E. Jones, Y. Cui, B. L Farmer, M. C. McAlpine, R. R. Naik, Preferential binding of peptides to graphene edges and planes. *J Am Chem Soc* 133, 14480-14483 (2011); published online EpubSep (10.1021/ja2042832).
19. T. P. Hopp, K. S. Prickett, V. L Price, R. T. Libby, C. J. March, D. Pat Cerretti, D. L. Urdal, P. J. Conlon, A Short Polypeptide Marker Sequence Useful for Recombinant Protein Identification and Purification. *Nat Biotech* 6, 1204-1210 (1988).
20. M. J. Pender, L. A. Sowards, J. D. Hartgerink, M. O. Stone, R. R. Naik, Peptide-mediated formation of single-wall carbon nanotube composites. *Nano Lett* 6, 40-44 (2006); published online EpubJan (10.1021/nl051899r).
21. J. M. Slocik, M. O. Stone, R. R. Naik, Synthesis of gold nanoparticles using multifunctional peptides. *Small* 1, 1048-1052 (2005); published online EpubNov (10.1002/smll.200500172).

22. W. J. Chung, K. Y. Kwon, J. Song, S. W. Lee, Evolutionary screening of collagen-like peptides that nucleate hydroxyapatite crystals. *Langmuir* 27, 7620-7628 (2011); published online EpubJun (10.1021/la104757 g).
23. E. E. Oren, C. Tamerler, D. Sahin, M. Hnilova, U. O. Seker, M. Sarikaya, R. Samudrala, A novel knowledge-based approach to design inorganic-binding peptides. *Bioinformatic* 23, 2816-2822 (2007); published online EpubNov (10.1093/bioinformatics/btm436).
24. B. Zakeri, J. O. Fierer, E. Celik, E. C. Chittock, U. Schwarz-Linek, V. T. Moy, M. Howarth, Peptide tag forming a rapid covalent bond to a protein, through engineering abacterial adhesin. *Proc Natl Acad Sci USA* 109, E690-697 (2012); published online EpubMar (1115485109 [pii]10.1073/pnas.1115485109).
25. C. L Giltner, E. J. van Schaik, G. F. Audette, D. Kao, R. S. Hodges, D. J. Hassett, R. T. Irvin, The *Pseudomonas aeruginosa* type IV pilin receptor binding domain functions as an adhesin for both biotic and abiotic surfaces. *Mol Microbiol* 59, 1083-1096 (2006); published online EpubFeb (MMI5002 [pii]10.111fj.1365-2958.2005.05002.x).
26. W. Zhou, D. T. Schwartz, F. Baneyx, Single-pot biofabrication of zinc sulfide immunoquantum dots. *J Am Chem Soc* 132, 4731-4738 (2010); published online EpubApr (10.1021/ja909406n).
27. M. E. Houston, H. Chao, R. S. Hodges, B. D. Sykes, C. M. Kay, F. D. Sönnichsen, M. C. Loewen, P. L Davies, Binding of an oligopeptide to a specific plane of ice. *J Biol Chem* 273, 11714-11718 (1998); published online EpubMay (
28. A. Arakaki, J. Webb, T. Matsunaga, A novel protein tightly bound to bacterial magnetic particles in Magnetospirillum magneticum strain AMB-1. *J Biol Chem* 278, 8745-8750 (2003); published online EpubMar (10.1074/jbc.M211729200).
29. J. D. Taylor, Y. Zhou, P. S. Salgado, A. Patwardhan, M. Mcguffie, T. Pape, G. Grabe, E. Ashman, S. C. Constable, P. J. Simpson, W.-C. Lee, E. Cota, M. R. Chapman, S. J. Matthews, Atomic Resolution Insights into Curli Fiber Biogenesis. *Structure* 19, 1307-1316 (2011); published online EpubSep 01 (10.1016/j.str.2011.05.015).
30. O. Vidal, R. Longin, C. Prigent-Combaret, C. Dorel, M. Hooreman, P. Lejeune, Isolation of an *Escherichia coli* K-12 mutant strain able to form biofilms on inert surfaces: involvement of a new ompR allele that increases curli expression. *J Bacteriol* 180, 2442-2449 (1998); published online EpubMay (
31. B. Zakeri, J. O. Fierer, E. Celik, E. C. Chittock, U. Schwarz-Linek, V. T. Moy, M. Howarth, Peptide tag forming a rapid covalent bond to a protein, through engineering a bacterial adhesin. *Proceedings of the National Academy of Sciences* 109, E690-697 (2012); published online EpubApr 20 (10.1073/pnas.1115485109).

```
CsgA polypeptide NCBI Ref Seq: NP_415560
                                                           SEQ ID NO: 1
    1   mkllkvaaia aivfsgsala gvvpqygggg nhggggnnsg pnselniyqy gggnsalalq 61   tdarnsdlti tqhgggngad vgqgsddssi dltqrgfgns atldqwngkn semtvkqfgg 121   gngaavdqta snssvnvtqv gfgnnatahq y nucleic acid sequence of CsgA-SpyTag
                                                           SEQ ID NO: 2
ATGAAACTTTTAAAAGTAGCAGCAATTGCAGCAATCGTATTCTCCGGTAGCGCTCTGGCA

GGTGTTGTTCCTCAGTACGGCGGCGGCGGTAACCACGGTGGTGGCGGTAATAATAGCGG

CCCCAAATTCTGAGCTGAACATTTACCAGTACGGTGGCGGTAACTCTGCACTTGCTCTGCA

AACTGATGCCCGTAACTCTGACTTGACTATTACCCAGCATGGCGGCGGTAATGGTGCAGA

TGTTGGTCAGGGCTCAGATGACAGCTCAATCGATCTGACCCAACGTGGCTTCGGTAACAG

CGCTACTCTTGATCAGTGGAACGGCAAAAATTCTGAAATGACGGTTAAACAGTTCGGTG

GTGGCAACGGTGCTGCAGTTGACCAGACTGCATCTAACTCCTCCGTCAACGTGACTCAGG

TTGGCTTTGGTAACAACGCGACCGCTCATCAGTACGGCAGCGGTGGTTCTGGCGCGCACA

TCGTTATGGTTGACGCGTACAAACCGACCAAATGA amino acid sequence of CsgA-SpyTag
                                                           SEQ ID NO: 3
MKLLKVAAIAAIVFSGSALAGVVPQYGGGGNHGGGGNNSGPNSELNIYQYGGGNSALALQT

DARNSDLTITQHGGGNGADVGQGSDDSSIDLTQRGFGNSATLDQWNGKNSEMTVKQFGG

GNGAAVDQTASNSSVNVTQVGFGNNATAHQYGSGGSGAHIVMVDAYKPTK nucleic acid sequence of Amylase-SpyCatcher
                                                           SEQ ID NO: 4
ATGGGCAGCAGCCATCATCATCATCATCACAGCAGCGGCCTGGTGCCGCGCGGCAGCCA

TATGGCAAATCTTAATGGGACGCTGATGCAGTATTTTGAATGGTACATGCCCAATGACGG

CCAACATTGGAAGCGCTTGCAAAACGACTCGGCATATTTGGCTGAACACGGTATTACTGC

CGTCTGGATTCCCCCGGCATATAAGGGAACGAGCCAAGCGGATGTGGGCTACGGTGCTT
```

-continued

```
ACGACCTTTATGATTTAGGGGAGTTTCATCAAAAAGGGACGGTTCGGACAAAGTACGGC
ACAAAAGGAGAGCTGCAATCTGCGATCAAAAGTCTTCATTCCCGCGACATTAACGTTTAC
GGGGATGTGGTCATCAACCACAAAGGCGGCGCTGATGCGACCGAAGATGTAACCGCGGT
TGAAGTCGATCCCGCTGACCGCAACCGCGTAATTTCAGGAGAACACCCAATTAAAGCCT
GGACACATTTTCATTTTCCGGGGCGCGGCAGCACATACAGCGATTTTAAATGGCATTGGT
ACCATTTTGACGGAACCGATTGGGACGAGTCCCGAAAGCTGAACCGCATCTATAAGTTTC
AAGGAAAGGCTTGGGATTGGGAAGTTTCCAATGAAAACGGCAACTATGATTATTTGATG
TATGCCGACATCGATTATGACCATCCTGATGTCGCAGCAGAAATTAAGAGATGGGGCAC
TTGGTATGCCAATGAACTGCAATTGGACGGTTTCCGTCTTGATGCTGTCAAACACATTAA
ATTTTCTTTTTTGCGGGATTGGGTTAATCATGTCAGGGAAAAAACGGGGAAGGAAATGTT
TACGGTAGCTGAATATTGGCAGAATGACTTGGGCGCGCTGGAAAACTATTTGAACAAAA
CAAATTTTAATCATTCAGTGTTTGACGTGCCGCTTCATTATCAGTTCCATGCTGCATCGAC
ACAGGGAGGCGGCTATGATATGAGGAAATTGCTGAACGGTACGGTCGTTTCCAAGCATC
CGTTGAAATCGGTTACATTTGTCGATAACCATGATACACAGCCGGGGCAATCGCTTGAGT
CGACTGTCCAAACATGGTTTAAGCCGCTTGCTTACGCTTTTATTCTCACAAGGGAATCTG
GATACCCTCAGGTTTTCTACGGGGATATGTACGGGACGAAAGGAGACTCCCAGCGCGAA
ATTCCTGCCTTGAAACACAAAATTGAACCGATCTTAAAAGCGAGAAAACAGTATGCGTA
CGGAGCACAGCATGATTATTTCGACCACCATGACATTGTCGGCTGGACAAGGGAAGGCG
ACAGCTCGGTTGCAAATTCAGGTTTGGCGGCATTAATAACAGACGGACCCGGTGGGGCA
AAGCGAATGTATGTCGGCCGGCAAAACGCCGGTGAGACATGGCATGACATTACCGGAAA
CCGTTCGGAGCCGGTTGTCATCAATTCGGAAGGCTGGGGAGAGTTTCACGTAAACGGCG
GGTCGGTTTCAATTTATGTTCAAAGAGGCGGCGGTTCTGATTACGACATCCCAACGACCG
AAAACCTGTATTTTCAGGGCGCCATGGTTGATACCTTATCAGGTTTATCAAGTGAGCAAG
GTCAGTCCGGTGATATGACAATTGAAGAAGATAGTGCTACCCATATTAAATTCTCAAAAC
GTGATGAGGACGGCAAAGAGTTAGCTGGTGCAACTATGGAGTTGCGTGATTCATCTGGT
AAAACTATTAGTACATGGATTTCAGATGGACAAGTGAAAGATTTCTACCTGTATCCAGGA
AAATATACATTTGTCGAAACCGCAGCACCAGACGGTTATGAGGTAGCAACTGCTATTAC
CTTTACAGTTAATGAGCAAGGTCAGGTTACTGTAAATGGCAAAGCAACTAAAGGTGACG
CTCATATTTAA
``` amino acid sequence of Amylase-SpyCatcher

SEQ ID NO: 5

MGSSHHHHHHSSGLVPRGSHMANLNGTLMQYFEWYMPNDGQHWKRLQNDSAYLAEHGIT
AVWIPPAYKGTSQADVGYGAYDLYDLGEFHQKGTVRTKYGTKGELQSAIKSLHSRDINVYG
DVVINHKGGADATEDVTAVEVDPADRNRVISGEHPIKAWTHFHFPGRGSTYSDFKWHWYHF
DGTDWDESRKLNRIYKFQGKAWDWEVSNENGNYDYLMYADIDYDHPDVAAEIKRWGTWY
ANELQLDGFRLDAVKHIKFSFLRDWVNHVREKTGKEMFTVAEYWQNDLGALENYLNKTNF
NHSVFDVPLHYQFHAASTQGGGYDMRKLLNGTVVSKHPLKSVTFVDNHDTQPGQSLESTVQ
TWFKPLAYAFILTRESGYPQVFYGDMYGTKGDSQREIPALKHKIEPILKARKQYAYGAQHDY
FDHHDIVGWTREGDSSVANSGLAALITDGPGGAKRMYVGRQNAGETWHDITGNRSEPVVIN
SEGWGEFHVNGGSVSIYVQRGGGSDYDIPTTENLYFQGAMVDTLSGLSSEQGQSGDMTIEED
SATHIKFSKRDEDGKELAGATMELRDSSGKTISTWISDGQVKDFYLYPGKYTFVETAAPDGY
EVATAITFTVNEQGQVTVNGKATKGDAHI

What is claimed herein is:

1. An engineered CsgA polypeptide comprising a wild-type *Escherichia coli* (*E. coli*) CsgA polypeptide with a C-terminal display tag flanking the CsgA, wherein the display tag comprises an activity polypeptide and a flexible polypeptide linker sequence, wherein the linker sequence is located N-terminal to the display tag, wherein the activity polypeptide comprises a binding domain selected from the group consisting of SpyTag peptide, metal binding domain (MBD) peptide, graphene binding peptide (GBP), carbon nanotube binding peptide (CBP), gold binding A3 peptide, ZnS quantum dot templating CT43 peptide, FLAG affinity tag peptide, ZnS quantum dot templating Z8 peptide, CdS quantum dot templating E14 peptide, quartz/glass binding QBP1 peptide, hydroxyapatite templating CLP12 peptide, ice crystal binding AFP8 peptide, biotin acceptor peptide (BAP), biotin carboxyl carrier protein (BCCP), and a peptide comprising a LPXTG (SEQ ID NO: 23) motif.

2. The CsgA polypeptide of claim 1, wherein the linker sequence consists of glycine and serine residues.

3. A composition comprising the engineered CsgA polypeptide of claim 1.

4. The composition of claim 3, wherein the composition comprises filaments comprising the engineered CsgA polypeptide of claim 1.

5. The composition of claim 3, wherein the composition comprises a proteinaceous network.

6. The composition of claim 3, wherein the composition further comprises proteinaceous biofilm components.

7. The composition of claim 3, wherein the composition further comprises an engineered microbial cell comprising a vector or nucleic acid sequence encoding the engineered CsgA polypeptide.

8. The composition of claim 3, wherein the composition further comprises a functionalizing polypeptide comprising an interacting domain.

* * * * *

SEQUENCE LISTING

<160> NUMBER OF SEQ ID NOS: 23

<210> SEQ ID NO 1
<211> LENGTH: 151
<212> TYPE: PRT
<213> ORGANISM: Artificial
<220> FEATURE:
<223> OTHER INFORMATION: Engineered CsgA polypeptide

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 2
<211> LENGTH: 513
<212> TYPE: DNA
<213> ORGANISM: Artificial
<220> FEATURE:
<223> OTHER INFORMATION: Nucleic acid sequence of CsgA-SpyTag

<400> SEQUENCE: 2
atgaaacttt taaaagtagc agcaattgca gcaatcgtat tctccggtag cgctctggca      60
ggtgttgttc ctcagtacgg cggcggcggt aaccacggtg gtggcggtaa taatagcggc     120
ccaaattctg agctgaacat ttaccagtac ggtggcggta actctgcact tgctctgcaa     180
actgatgccc gtaactctga cttgactatt acccagcatg gcggcggtaa tggtgcagat     240
gttggtcagg gctcagatga cagctcaatc gatctgaccc aacgtggctt cggtaacagc     300
gctactcttg atcagtggaa cggcaaaaat tctgaaatga cggttaaaca gttcggtggt     360
ggcaacggtg ctgcagttga ccagactgca tctaactcct ccgtcaacgt gactcaggtt     420
ggctttggta caacgcgac cgctcatcag tacggcagcg tggttctgg cgcgcacatc       480 gttatggttg acgcgtacaa accgaccaaa tga                                   513

<210> SEQ ID NO 3
<211> LENGTH: 170
<212> TYPE: PRT
<213> ORGANISM: Artificial
<220> FEATURE:
<223> OTHER INFORMATION: Amino acid sequence of CsgA-SpyTag

<400> SEQUENCE: 3

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Asn Gly Ala Asp
65              70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr Gly Ser Gly Gly Ser Gly Ala His Ile
145                 150                 155                 160

Val Met Val Asp Ala Tyr Lys Pro Thr Lys
                165                 170
```

<210> SEQ ID NO 4
<211> LENGTH: 1914
<212> TYPE: DNA
<213> ORGANISM: Artificial
<220> FEATURE:
<223> OTHER INFORMATION: Nucleic acid sequence of Amylase-SpyCatcher

<400> SEQUENCE: 4

```
atgggcagca gccatcatca tcatcatcac agcagcggcc tggtgccgcg cggcagccat      60
atggcaaatc ttaatgggac gctgatgcag tattttgaat ggtacatgcc caatgacggc     120
caacattgga gcgcttgca aaacgactcg gcatatttgg ctgaacacgg tattactgcc      180
gtctggattc ccccggcata agggaacg agccaagcgg atgtgggcta cggtgcttac       240
gacctttatg atttagggga gtttcatcaa aaagggacgg ttcggacaaa gtacggcaca     300
aaaggagagc tgcaatctgc gatcaaaagt cttcattccc gcgacattaa cgtttacggg     360
gatgtggtca tcaaccacaa aggcggcgct gatgcgaccg aagatgtaac cgcggttgaa     420
gtcgatcccg ctgaccgcaa ccgcgtaatt tcaggagaac acccaattaa agcctggaca     480
cattttcatt ttccggggcg cggcagcaca tacagcgatt ttaaatggca ttggtaccat     540
tttgacggaa ccgattggga cgagtcccga aagctgaacc gcatctataa gtttcaagga     600
aaggcttggg attgggaagt ttccaatgaa acggcaact atgattattt gatgtatgcc      660
gacatcgatt atgaccatcc tgatgtcgca gcagaaatta agagatgggg cacttggtat     720
gccaatgaac tgcaattgga cggtttccgt cttgatgctg tcaaacacat taaattttct     780
tttttgcggg attgggttaa tcatgtcagg gaaaaacgg ggaaggaat gtttacggta      840
gctgaatatt ggcagaatga cttgggcgcg ctggaaaact atttgaacaa aacaaatttt    900
aatcattcag tgtttgacgt gccgcttcat tatcagttcc atgctgcatc gacacaggga    960
ggcggctatg atatgaggaa attgctgaac ggtacggtcg tttccaagca tccgttgaaa   1020
```

```
tcggttacat tgtcgataa ccatgataca cagccggggc aatcgcttga gtcgactgtc   1080
caaacatggt ttaagccgct tgcttacgct tttattctca caagggaatc tggatacccct  1140 caggttttct acggggatat gtacgggacg aaaggagact cccagcgcga aattcctgcc   1200
ttgaaacaca aaattgaacc gatcttaaaa gcgagaaaac agtatgcgta cggagcacag   1260
catgattatt tcgaccacca tgacattgtc ggctggacaa gggaaggcga cagctcggtt   1320
gcaaattcag gtttggcggc attaataaca gacggacccg gtggggcaaa gcgaatgtat   1380
gtcggccggc aaaacgccgg tgagacatgg catgacatta ccggaaaccg ttcggagccg   1440
gttgtcatca attcggaagg ctggggagag tttcacgtaa acggcgggtc ggtttcaatt   1500
tatgttcaaa gaggcggcgg ttctgattac gacatcccaa cgaccgaaaa cctgtatttt   1560
cagggcgcca tggttgatac cttatcaggt ttatcaagtg agcaaggtca gtccggtgat   1620
atgacaattg aagaagatag tgctacccat attaaattct caaaacgtga tgaggacggc   1680
aaagagttag ctggtgcaac tatggagttg cgtgattcat ctggtaaaac tattagtaca   1740
tggatttcag atggacaagt gaaagatttc tacctgtatc caggaaaata tacatttgtc   1800
gaaaccgcag caccagacgg ttatgaggta gcaactgcta ttacctttac agttaatgag   1860
caaggtcagg ttactgtaaa tggcaaagca actaaaggtg acgctcatat ttaa         1914
```

<210> SEQ ID NO 5
<211> LENGTH: 637
<212> TYPE: PRT
<213> ORGANISM: Artificial
<220> FEATURE:
<223> OTHER INFORMATION: Amino acid sequence of Amylase-SpyCatcher

<400> SEQUENCE: 5

Met Gly Ser Ser His His His His His His Ser Ser Gly Leu Val Pro
1               5                   10                  15

Arg Gly Ser His Met Ala Asn Leu Asn Gly Thr Leu Met Gln Tyr Phe
            20                  25                  30

Glu Trp Tyr Met Pro Asn Asp Gly Gln His Trp Lys Arg Leu Gln Asn
        35                  40                  45

Asp Ser Ala Tyr Leu Ala Glu His Gly Ile Thr Ala Val Trp Ile Pro
    50                  55                  60

Pro Ala Tyr Lys Gly Thr Ser Gln Ala Asp Val Gly Tyr Gly Ala Tyr
65                  70                  75                  80

Asp Leu Tyr Asp Leu Gly Glu Phe His Gln Lys Gly Thr Val Arg Thr
                85                  90                  95

Lys Tyr Gly Thr Lys Gly Glu Leu Gln Ser Ala Ile Lys Ser Leu His
            100                 105                 110

Ser Arg Asp Ile Asn Val Tyr Gly Asp Val Val Ile Asn His Lys Gly
        115                 120                 125

Gly Ala Asp Ala Thr Glu Asp Val Thr Ala Val Glu Val Asp Pro Ala
    130                 135                 140

Asp Arg Asn Arg Val Ile Ser Gly Glu His Pro Ile Lys Ala Trp Thr
145                 150                 155                 160

His Phe His Phe Pro Gly Arg Gly Ser Thr Tyr Ser Asp Phe Lys Trp
                165                 170                 175

His Trp Tyr His Phe Asp Gly Thr Asp Trp Asp Glu Ser Arg Lys Leu
            180                 185                 190

Asn Arg Ile Tyr Lys Phe Gln Gly Lys Ala Trp Asp Trp Glu Val Ser
        195                 200                 205

-continued

Asn Glu Asn Gly Asn Tyr Asp Tyr Leu Met Tyr Ala Asp Ile Asp Tyr
210                 215                 220

Asp His Pro Asp Val Ala Ala Glu Ile Lys Arg Trp Gly Thr Trp Tyr
225                 230                 235                 240

Ala Asn Glu Leu Gln Leu Asp Gly Phe Arg Leu Asp Ala Val Lys His
                245                 250                 255

Ile Lys Phe Ser Phe Leu Arg Asp Trp Val Asn His Val Arg Glu Lys
            260                 265                 270

Thr Gly Lys Glu Met Phe Thr Val Ala Glu Tyr Trp Gln Asn Asp Leu
        275                 280                 285

Gly Ala Leu Glu Asn Tyr Leu Asn Lys Thr Asn Phe Asn His Ser Val
290                 295                 300

Phe Asp Val Pro Leu His Tyr Gln Phe His Ala Ala Ser Thr Gln Gly
305                 310                 315                 320

Gly Gly Tyr Asp Met Arg Lys Leu Leu Asn Gly Thr Val Val Ser Lys
                325                 330                 335

His Pro Leu Lys Ser Val Thr Phe Val Asp Asn His Asp Thr Gln Pro
            340                 345                 350

Gly Gln Ser Leu Glu Ser Thr Val Gln Thr Trp Phe Lys Pro Leu Ala
        355                 360                 365

Tyr Ala Phe Ile Leu Thr Arg Glu Ser Gly Tyr Pro Gln Val Phe Tyr
370                 375                 380

Gly Asp Met Tyr Gly Thr Lys Gly Asp Ser Gln Arg Glu Ile Pro Ala
385                 390                 395                 400

Leu Lys His Lys Ile Glu Pro Ile Leu Lys Ala Arg Lys Gln Tyr Ala
                405                 410                 415

Tyr Gly Ala Gln His Asp Tyr Phe Asp His His Asp Ile Val Gly Trp
            420                 425                 430

Thr Arg Glu Gly Asp Ser Ser Val Ala Asn Ser Gly Leu Ala Ala Leu
        435                 440                 445

Ile Thr Asp Gly Pro Gly Gly Ala Lys Arg Met Tyr Val Gly Arg Gln
450                 455                 460

Asn Ala Gly Glu Thr Trp His Asp Ile Thr Gly Asn Arg Ser Glu Pro
465                 470                 475                 480

Val Val Ile Asn Ser Glu Gly Trp Gly Glu Phe His Val Asn Gly Gly
                485                 490                 495

Ser Val Ser Ile Tyr Val Gln Arg Gly Gly Gly Ser Asp Tyr Asp Ile
            500                 505                 510

Pro Thr Thr Glu Asn Leu Tyr Phe Gln Gly Ala Met Val Asp Thr Leu
        515                 520                 525

Ser Gly Leu Ser Ser Glu Gln Gly Gln Ser Gly Asp Met Thr Ile Glu
530                 535                 540

Glu Asp Ser Ala Thr His Ile Lys Phe Ser Lys Arg Asp Glu Asp Gly
545                 550                 555                 560

Lys Glu Leu Ala Gly Ala Thr Met Glu Leu Arg Asp Ser Ser Gly Lys
                565                 570                 575

Thr Ile Ser Thr Trp Ile Ser Asp Gly Gln Val Lys Asp Phe Tyr Leu
            580                 585                 590

Tyr Pro Gly Lys Tyr Thr Phe Val Glu Thr Ala Ala Pro Asp Gly Tyr
        595                 600                 605

```
Glu Val Ala Thr Ala Ile Thr Phe Thr Val Asn Glu Gln Gly Gln Val
    610                 615                 620
Thr Val Asn Gly Lys Ala Thr Lys Gly Asp Ala His Ile
625                 630                 635

<210> SEQ ID NO 6
<211> LENGTH: 7
<212> TYPE: PRT
<213> ORGANISM: Artificial
<220> FEATURE:
<223> OTHER INFORMATION: Fig. 1C polypeptide insertion into the C3
      site - GBP

<400> SEQUENCE: 6

Glu Pro Leu Gln Leu Lys Met
1               5

<210> SEQ ID NO 7
<211> LENGTH: 12
<212> TYPE: PRT
<213> ORGANISM: Artificial
<220> FEATURE:
<223> OTHER INFORMATION: Fig. 1C polypeptide insertion into the C3
      site - CBP

<400> SEQUENCE: 7

His Ser Ser Tyr Trp Tyr Ala Phe Asn Asn Lys Thr
1               5                   10

<210> SEQ ID NO 8
<211> LENGTH: 12
<212> TYPE: PRT
<213> ORGANISM: Artificial
<220> FEATURE:
<223> OTHER INFORMATION: Fig. 1C polypeptide insertion into the C3
      site - A3

<400> SEQUENCE: 8

Ala Tyr Ser Ser Gly Ala Pro Pro Met Pro Pro Phe
1               5                   10

<210> SEQ ID NO 9
<211> LENGTH: 13
<212> TYPE: PRT
<213> ORGANISM: Artificial
<220> FEATURE:
<223> OTHER INFORMATION: Fig. 1C polypeptide insertion into the C3
      site - SpyTag

<400> SEQUENCE: 9

Ala His Ile Val Met Val Asp Ala Tyr Lys Pro Thr Lys
1               5                   10

<210> SEQ ID NO 10
<211> LENGTH: 17
<212> TYPE: PRT
<213> ORGANISM: Artificial
<220> FEATURE:
<223> OTHER INFORMATION: Fig. 1C polypeptide insertion into the C3
      site - MBD

<400> SEQUENCE: 10

Lys Cys Thr Ser Asp Gln Asp Glu Gln Phe Ile Pro Lys Gly Cys Ser
1               5                   10                  15
Lys
```

```
<210> SEQ ID NO 11
<211> LENGTH: 18
<212> TYPE: PRT
<213> ORGANISM: Artificial
<220> FEATURE:
<223> OTHER INFORMATION: Fig. 1C polypeptide insertion into the C3
      site - CT43

<400> SEQUENCE: 11

Cys Gly Pro Ala Gly Asp Ser Ser Gly Val Asp Ser Arg Ser Val Gly
1               5                   10                  15

Pro Cys

<210> SEQ ID NO 12
<211> LENGTH: 59
<212> TYPE: PRT
<213> ORGANISM: Artificial
<220> FEATURE:
<223> OTHER INFORMATION: Fig. 1C polypeptide insertion into the C3
      site - Mms6

<400> SEQUENCE: 12

Gly Gly Thr Ile Trp Thr Gly Lys Gly Leu Gly Leu Gly Leu Gly Leu
1               5                   10                  15

Gly Leu Gly Ala Trp Gly Pro Ile Ile Leu Gly Val Val Gly Ala Gly
                20                  25                  30

Ala Val Tyr Ala Tyr Met Lys Ser Arg Asp

```
<210> SEQ ID NO 16
<211> LENGTH: 8
<212> TYPE: PRT
<213> ORGANISM: Artificial
<220> FEATURE:
<223> OTHER INFORMATION: FLAG

<400> SEQUENCE: 16

Asp Tyr Lys Asp Asp Asp Asp Lys
1               5

<210> SEQ ID NO 17
<211> LENGTH: 12
<212> TYPE: PRT
<213> ORGANISM: Artificial
<220> FEATURE:
<223> OTHER INFORMATION: Z8

<400> SEQUENCE: 17

Leu Arg Arg Ser Ser Glu Ala His Asn Ser Ile Val
1               5                   10

<210> SEQ ID NO 18
<211> LENGTH: 12
<212> TYPE: PRT
<213> ORGANISM: Artificial
<220> FEATURE:
<223> OTHER INFORMATION: E14

<400> SEQUENCE: 18

Pro Trp Ile Pro Thr Pro Arg Pro Thr Phe Thr Gly
1               5                   10

<210> SEQ ID NO 19
<211> LENGTH: 12
<212> TYPE: PRT
<213> ORGANISM: Artificial
<220> FEATURE:
<223> OTHER INFORMATION: QBP1

<400> SEQUENCE: 19

Pro Pro Pro Trp Leu Pro Tyr Met Pro Pro Trp Ser
1               5                   10

<210> SEQ ID NO 20
<211> LENGTH: 13
<212> TYPE: PRT
<213> ORGANISM: Artificial
<220> FEATURE:
<223> OTHER INFORMATION: CLP12

<400> SEQUENCE: 20

Asn Pro Tyr His Pro Thr Ile Pro Ala Gln Ser Val His
1               5                   10

<210> SEQ ID NO 21
<211> LENGTH: 23
<212> TYPE: PRT
<213> ORGANISM: Artificial
<220> FEATURE:
<223> OTHER INFORMATION: MBD

<400> SEQUENCE: 21

Lys Cys Thr Ser Asp Gln Asp Glu Gln Phe Ile Pro Lys Gly Cys Ser
1               5                   10                  15

Lys Gly Ser Gly Gly Ser Gly
            20
```

```
<210> SEQ ID NO 22
<211> LENGTH: 36
<212> TYPE: PRT
<213> ORGANISM: Artificial
<220> FEATURE:
<223> OTHER INFORMATION: AFP8

<400> SEQUENCE: 22

Asp Thr Ala Ser Asp Ala Ala Ala Ala Ala Leu Thr Ala Ala Asn
1               5                   10                  15

Ala Lys Ala Ala Ala Glu Leu Thr Ala Ala Asn Ala Ala Ala Ala Ala
            20                  25                  30

Ala Thr Ala Arg
        35

<210> SEQ ID NO 23
<211> LENGTH: 5
<212> TYPE: PRT
<213> ORGANISM: Artificial Sequence
<220> FEATURE:
<223> OTHER INFORMATION: LPXTG Motif
<220> FEATURE:
<221> NAME/KEY: MISC_FEATURE
<222> LOCATION: (3)..(3)
<223> OTHER INFORMATION: Xaa can be any amino acid

<400> SEQUENCE: 23

Leu Pro Xaa Thr Gly
1               5
```